United States Patent [19]

Heim et al.

[11] Patent Number: 5,409,700
[45] Date of Patent: Apr. 25, 1995

US005409700A

[54] PHARMACEUTICAL COMPOSITIONS COMPRISING MODIFIED AND UNMODIFIED PLASMINOGEN ACTIVATORS

[75] Inventors: Jutta Heim, Ramlinsburg; Fredericus A. M. Asselbergs, Riehen; Rolf Bürgi, Basel, all of Switzerland

[73] Assignee: Ciba-Geigy Corporation, Ardsley, N.Y.

[21] Appl. No.: 44,563

[22] Filed: Apr. 7, 1993

Related U.S. Application Data

[63] Continuation of Ser. No. 573,434, Aug. 27, 1990, abandoned.

[30] Foreign Application Priority Data

Sep. 1, 1989 [GB] United Kingdom ............... 8919803

[51] Int. Cl.$^6$ .................. A61K 37/54; A61K 37/547; C12N 9/48; C12N 9/72
[52] U.S. Cl. .............................. 424/94.64; 424/94.63; 514/2; 435/212; 435/215
[58] Field of Search .............................. 435/212, 215; 424/94.63, 94.64

[56] References Cited

FOREIGN PATENT DOCUMENTS

0223192 6/1987 European Pat. Off. .
0247674 12/1987 European Pat. Off. .

OTHER PUBLICATIONS

Collen et al. (1987) Amer. J. Cardiol. 60, 431–434.
Pierard et al. (1987) J. Biol. Chem. 262, 11771–11778.
Lee et al. (1988) J. Biol. Chem. 263, 2917–2924.
Pennica et al. (1983) Nature 301, 214–221.
Holmes et al. (1985) Bio/Technology 3, 923–929.
Collen et al., Circulation, 74:838 ∝ 842 (1986).
Collen, *Circulation*, 77:731–735 (1989).
Verstraete, *Klin. Wochenschr.*, 66:5–14 (1988), Abstract.

*Primary Examiner*—Elizabeth C. Weimar
*Assistant Examiner*—Deborah Crouch
*Attorney, Agent, or Firm*—W. Murray Spruill

[57] ABSTRACT

The present invention relates to pharmaceutical compositions comprising a combination of two different plasminogen activators which are used for the prophylaxis and therapie of thrombosis.

6 Claims, 40 Drawing Sheets

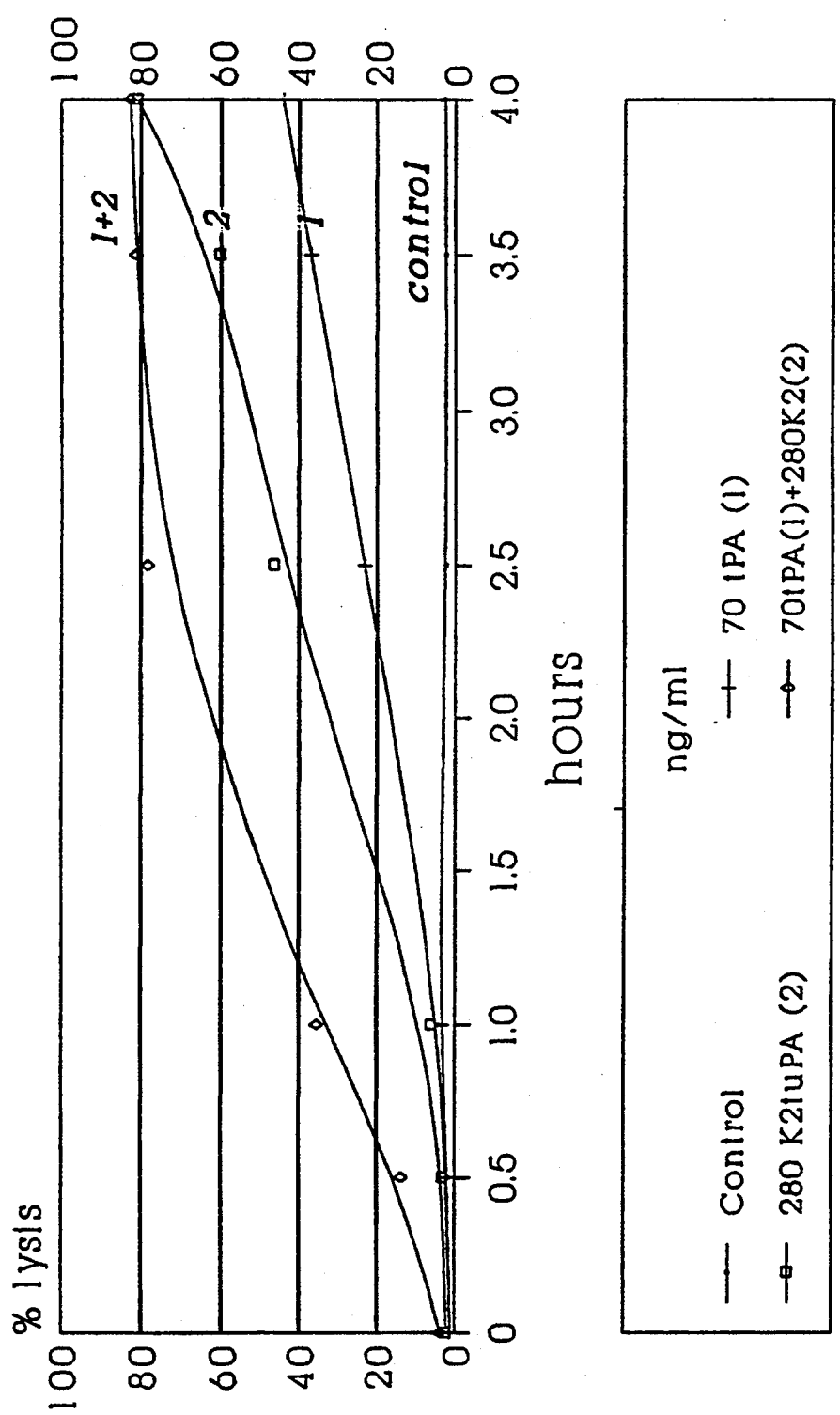
FIG. 1: Comb. of tPA (1) with K2tuPA (2)

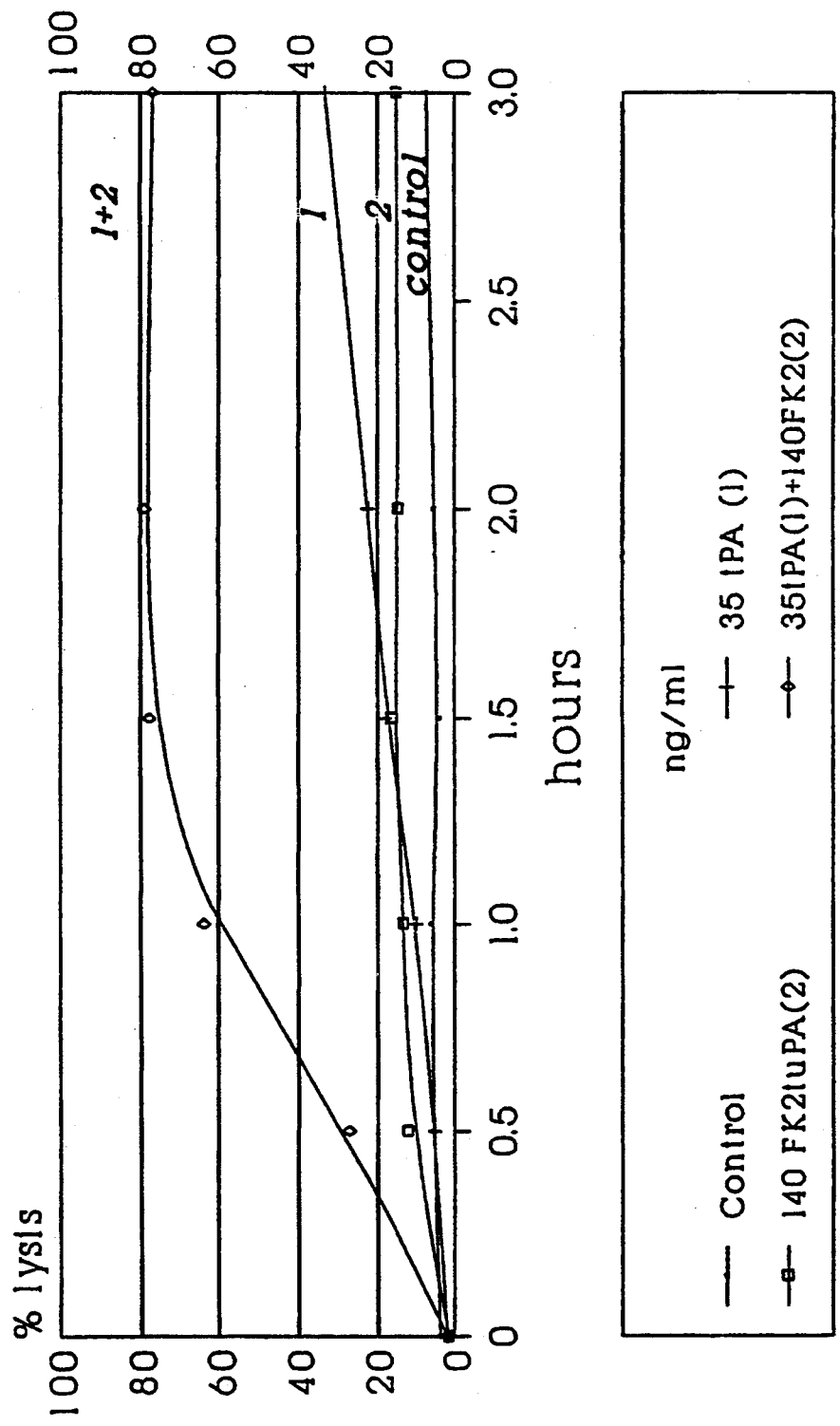
FIG. 2: Comb. of tPA (1) with FK2tuPA (2)

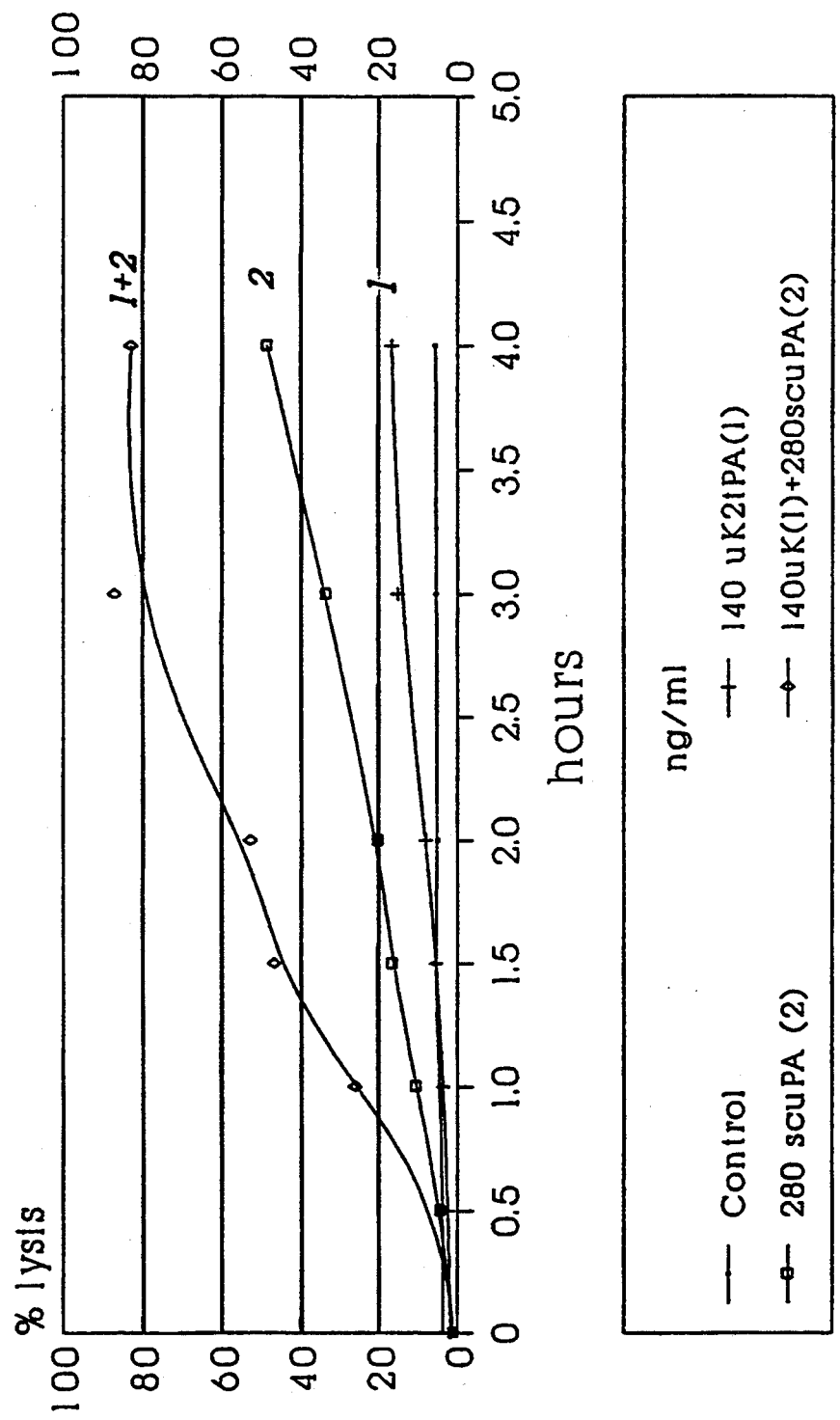
FIG. 3: Comb. of uK2tPA (1) with scuPA (2)

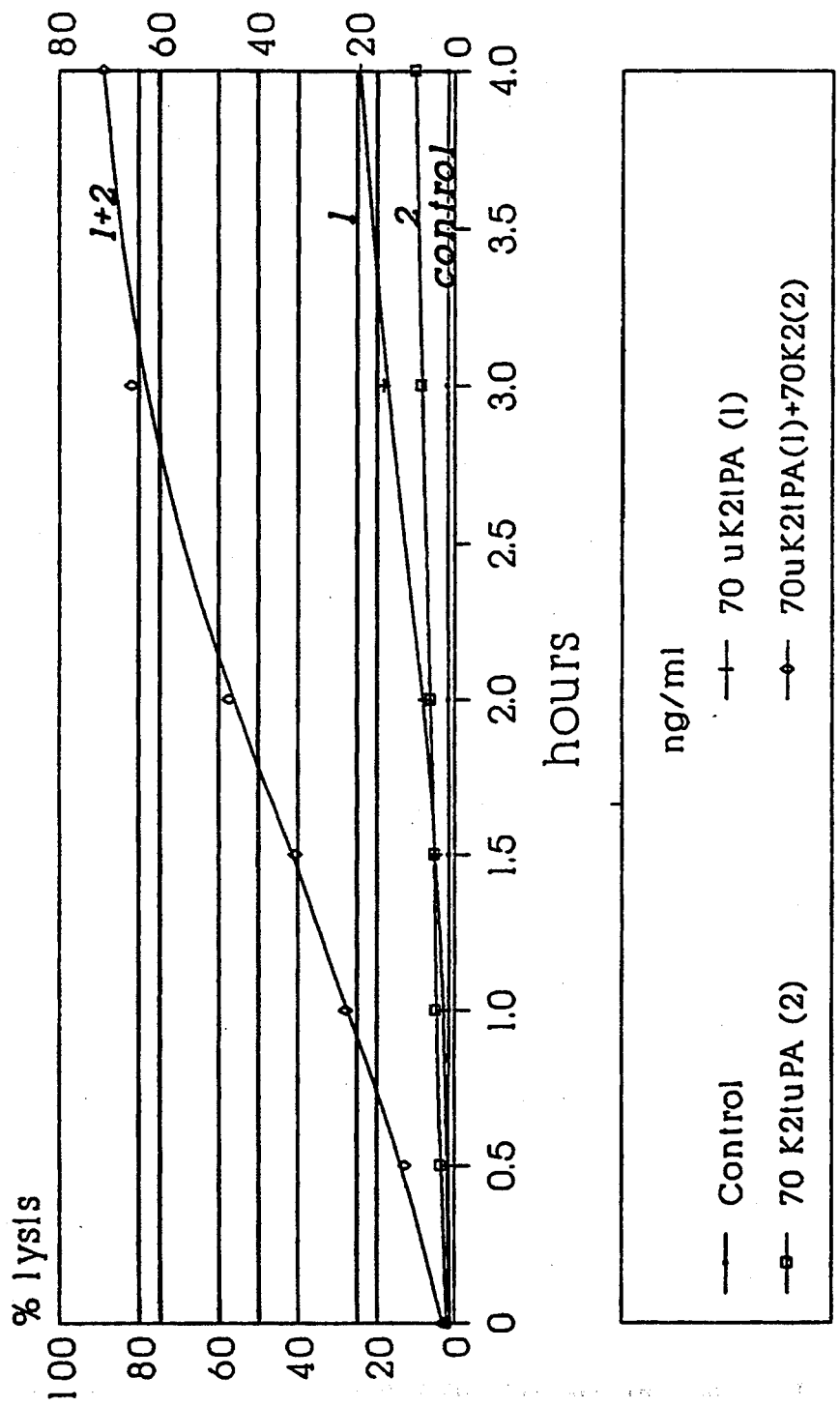
FIG. 4: Comb. of uK2tPA (1) with K2tuPA (2)

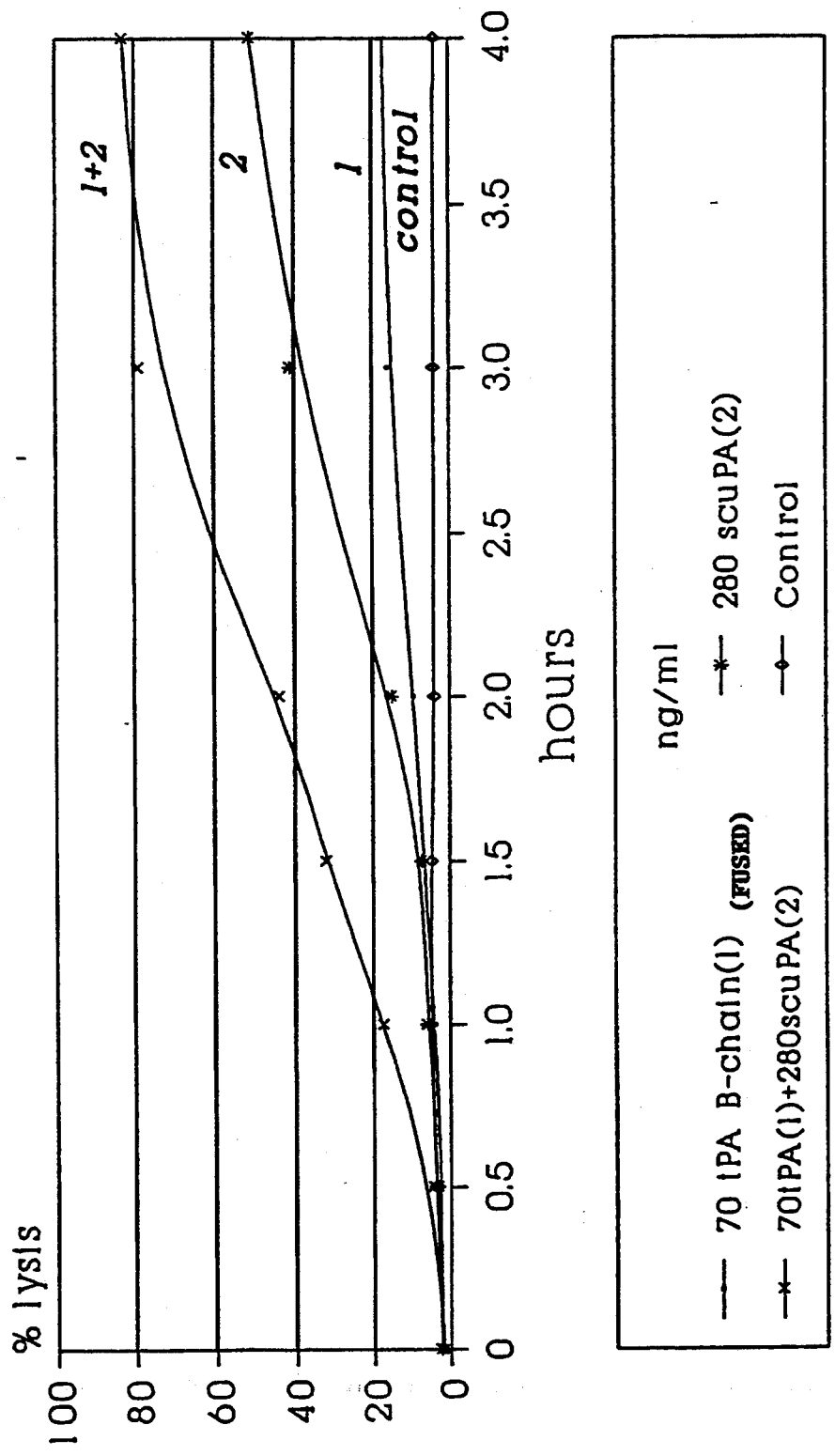
FIG. 5: Comb. of tPA B-chain(1) (FUSED) with scuPA(2)

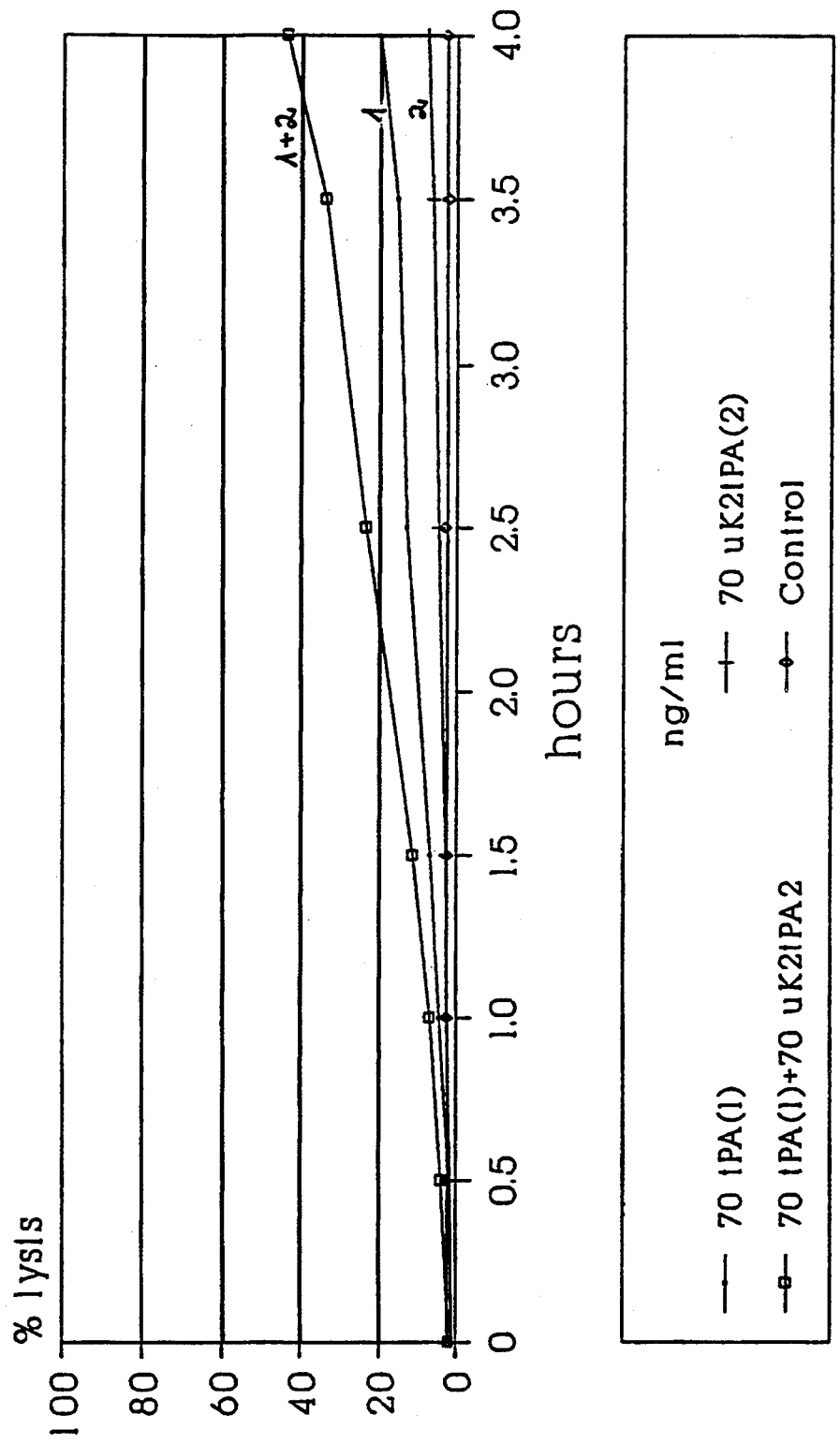
FIG. 6: Comb.of tPA (1) with uK2tPA (2)

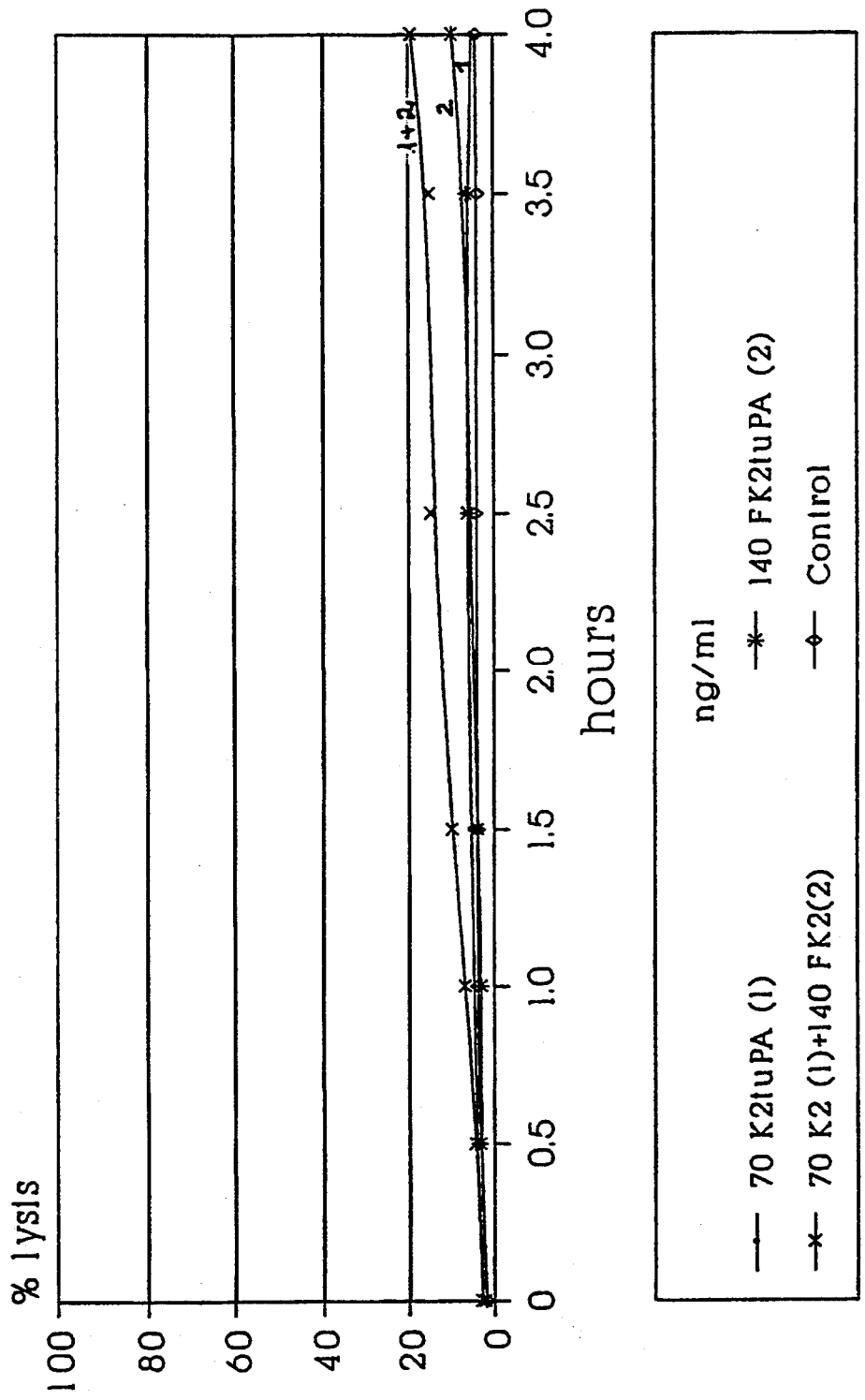
FIG. 7: Comb. of K2tuPA (1) with FK2tuPA (2)

FIG. 8 NUCLEOTIDE SEQUENCE AND DEDUCED AMINO ACID SEQUENCE OF t-PA cDNA INSERT PREPARED FROM HeLaS3 CELLS

```
  1 AGGGCTGGAGAGAAAACCTCTGCGAGGAAAGGGAAGGAGCAAGCCGTGAATTTAAGGGA

MET ASP ALA MET LYS ARG GLY LEU CYS CYS VAL    -25
 60 CGCTGTGAAGCAATC ATG GAT GCA ATG AAG AGA GGG CTC TGC TGT GTG

LEU LEU LEU CYS GLY ALA VAL PHE VAL SER PRO SER GLN GLU ILE   -10
108 CTG CTA CTG TGT GGA GCA GTC TTC GTT TCG CCC AGC CAG GAA ATC

HIS ALA ARG PHE ARG ARG GLY ALA ARG SER TYR GLN VAL ILE CYS     6
153 CAT GCC CGA TTC AGA AGA GGA GCC AGA TCT TAC CAA GTG ATC TGC

ARG ASP GLU LYS THR GLN MET ILE TYR GLN GLN HIS GLN SER TRP    21
198 AGA GAT GAA AAA ACG CAG ATG ATA TAC CAG CAA CAT CAG TCA TGG

LEU ARG PRO VAL LEU ARG SER ASN ARG VAL GLU TYR CYS TRP CYS    36
243 CTG CGC CCT GTG CTC AGA AGC AAC CGG GTG GAA TAT TGC TGG TGC

ASN SER GLY ARG ALA GLN CYS HIS SER VAL PRO VAL LYS SER CYS    51
288 AAC AGT GGC AGG GCA CAG TGC CAC TCA GTG CCT GTC AAA AGT TGC

SER GLU PRO ARG CYS PHE ASN GLY GLY THR CYS GLN GLN ALA LEU    66
333 AGC GAG CCA AGG TGT TTC AAC GGG GGC ACC TGC CAG CAG GCC CTG

TYR PHE SER ASP PHE VAL CYS GLN CYS PRO GLU GLY PHE ALA GLY    81
378 TAC TTC TCA GAT TTC GTG TGC CAG TGC CCC GAA GGA TTT GCT GGG

LYS CYS CYS GLU ILE ASP THR ARG ALA THR CYS TYR GLU ASP GLN    96
423 AAG TGC TGT GAA ATA GAT ACC AGG GCC ACG TGC TAC GAG GAC CAG

GLY ILE SER TYR ARG GLY THR TRP SER THR ALA GLU SER GLY ALA   111
468 GGC ATC AGC TAC AGG GGC ACG TGG AGC ACA GCG GAG AGT GGC GCC

GLU CYS THR ASN TRP ASN SER SER ALA LEU ALA GLN LYS PRO TYR   126
513 GAG TGC ACC AAC TGG AAC AGC AGC GCG TTG GCC CAG AAG CCC TAC

SER GLY ARG ARG PRO ASP ALA ILE ARG LEU GLY LEU GLY ASN HIS   141
558 AGC GGG CGG AGG CCA GAC GCC ATC AGG CTG GGC CTG GGG AAC CAC

ASN TYR CYS ARG ASN PRO ASP ARG ASP SER LYS PRO TRP CYS TYR   156
603 AAC TAC TGC AGA AAC CCA GAT CGA GAC TCA AAG CCC TGG TGC TAC

VAL PHE LYS ALA GLY LYS TYR SER SER GLU PHE CYS SER THR PRO   171
648 GTC TTT AAG GCG GGG AAG TAC AGC TCA GAG TTC TGC AGC ACC CCT

ALA CYS SER GLU GLY ASN SER ASP CYS TYR PHE GLY ASN GLY SER   186
693 GCC TGC TCT GAG GGA AAC AGT GAC TGC TAC TTT GGG AAT GGG TCA
```

FIG. 8 (CONTINUED)

```
          ALA TYR ARG GLY THR HIS SER LEU THR GLU SER GLY ALA SER CYS    201
      738 GCC TAC CGT GGC ACG CAC AGC CTC ACC GAG TCG GGT GCC TCC TGC

LEU PRO TRP ASN SER MET ILE LEU ILE GLY LYS VAL TYR THR ALA    216
      783 CTC CCG TGG AAT TCC ATG ATC CTG ATA GGC AAG GTT TAC ACA GCA

GLN ASN PRO SER ALA GLN ALA LEU GLY LEU GLY LYS HIS ASN TYR    231
      828 CAG AAC CCC AGT GCC CAG GCA CTG GGC CTG GGC AAA CAT AAT TAC

CYS ARG ASN PRO ASP GLY ASP ALA LYS PRO TRP CYS HIS VAL LEU    246
      873 TGC CGG AAT CCT GAT GGG GAT GCC AAG CCC TGG TGC CAC GTG CTG

LYS ASN ARG ARG LEU THR TRP GLU TYR CYS ASP VAL PRO SER CYS    261
      918 AAG AAC CGC AGG CTG ACG TGG GAG TAC TGT GAT GTG CCC TCC TGC

SER THR CYS GLY LEU ARG GLN TYR SER GLN PRO GLN PHE ARG ILE    276
      963 TCC ACC TGC GGC CTG AGA CAG TAC AGC CAG CCT CAG TTT CGC ATC

LYS GLY GLY LEU PHE ALA ASP ILE ALA SER HIS PRO TRP GLN ALA    291
     1008 AAA GGA GGG CTC TTC GCC GAC ATC GCC TCC CAC CCC TGG CAG GCT

ALA ILE PHE ALA LYS HIS ARG ARG SER PRO GLY GLU ARG PHE LEU    306
     1053 GCC ATC TTT GCC AAG CAC AGG AGG TCG CCC GGA GAG CGG TTC CTG

CYS GLY GLY ILE LEU ILE SER SER CYS TRP ILE LEU SER ALA ALA    321
     1098 TGC GGG GGC ATA CTC ATC AGC TCC TGC TGG ATT CTC TCT GCC GCC

HIS CYS PHE GLN GLU ARG PHE PRO PRO HIS HIS LEU THR VAL ILE    336
     1143 CAC TGC TTC CAG GAG AGG TTT CCG CCC CAC CAC CTG ACG GTG ATC

LEU GLY ARG THR TYR ARG VAL VAL PRO GLY GLU GLU GLU GLN LYS    351
     1188 TTG GGC AGA ACA TAC CGG GTG GTC CCT GGC GAG GAG GAG CAG AAA

PHE GLU VAL GLU LYS TYR ILE VAL HIS LYS GLU PHE ASP ASP ASP    366
     1233 TTT GAA GTC GAA AAA TAC ATT GTC CAT AAG GAA TTC GAT GAT GAC

THR TYR ASP ASN ASP ILE ALA LEU LEU GLN LEU LYS SER ASP SER    381
     1278 ACT TAC GAC AAT GAC ATT GCG CTG CTG CAG CTG AAA TCG GAT TCG

SER ARG CYS ALA GLN GLU SER SER VAL VAL ARG THR VAL CYS LEU    396
     1323 TCC CGC TGT GCC CAG GAG AGC AGC GTG GTC CGC ACT GTG TGC CTT

PRO PRO ALA ASP LEU GLN LEU PRO ASP TRP THR GLU CYS GLU LEU    411
     1368 CCC CCG GCG GAC CTG CAG CTG CCG GAC TGG ACG GAG TGT GAG CTC

SER GLY TYR GLY LYS HIS GLU ALA LEU SER PRO PHE TYR SER GLU    426
     1413 TCC GGC TAC GGC AAG CAT GAG GCC TTG TCT CCT TTC TAT TCG GAG

ARG LEU LYS GLU ALA HIS VAL ARG LEU TYR PRO SER SER ARG CYS    441
     1458 CGG CTG AAG GAG GCT CAT GTC AGA CTG TAC CCA TCC AGC CGC TGC
```

FIG. 8 (CONTINUED)

```
        THR SER GLN HIS LEU LEU ASN ARG THR VAL THR ASP ASN MET LEU    456
1503    ACA TCA CAA CAT TTA CTT AAC AGA ACA GTC ACC GAC AAC ATG CTG

CYS ALA GLY ASP THR ARG SER GLY GLY PRO GLN ALA ASN LEU HIS    471
1548    TGT GCT GGA GAC ACT CGG AGC GGC GGG CCC CAG GCA AAC TTG CAC

ASP ALA CYS GLN GLY ASP SER GLY GLY PRO LEU VAL CYS LEU ASN    486
1593    GAC GCC TGC CAG GGC GAT TCG GGA GGC CCC CTG GTG TGT CTG AAC

ASP GLY ARG MET THR LEU VAL GLY ILE ILE SER TRP GLY LEU GLY    501
1638    GAT GGC CGC ATG ACT TTG GTG GGC ATC ATC AGC TGG GGC CTG GGC

CYS GLY GLN LYS ASP VAL PRO GLY VAL TYR THR LYS VAL THR ASN    516
1683    TGT GGA CAG AAG GAT GTC CCG GGT GTG TAC ACT AAG GTT ACC AAC

TYR LEU ASP TRP ILE ARG ASP ASN MET ARG PRO                    527
1728    TAC CTA GAC TGG ATT CGT GAC AAC ATG CGA CCG TGA CCAGGAACACC

1775    CGACTCCTCAAAAGCAAATGAGATCCCGCCTCTTCTTCTTCAGAAGACACTGCAAAGGC

1834    GCAGTGCTTCTCTACAGACTTCTCCAGACCCACCACACCGCAGAAGCGGGACGAGACCC

1893    TACAGGAGAGGGAAGAGTGCATTTTCCCAGATACTTCCCATTTTGGAAGTTTTCAGGAC

1952    TTGGTCTGATTTCAGGATACTCTGTCAGATGGGAAGACATGAATGCACACTAGCCTCTC

2011    CAGGAATGCCTCCTCCCTGGGCAGAAAGTGGCCATGCCACCCTGTTTTACGCTAAAGCC

2070    CAACCTCCTGACCTGTCACCGTGAGCAGCTTTGGAAACAGGACCACAAAAATGAAAGCA

2129    TGTCTCAATAGTAAAAGATACAAGA
```

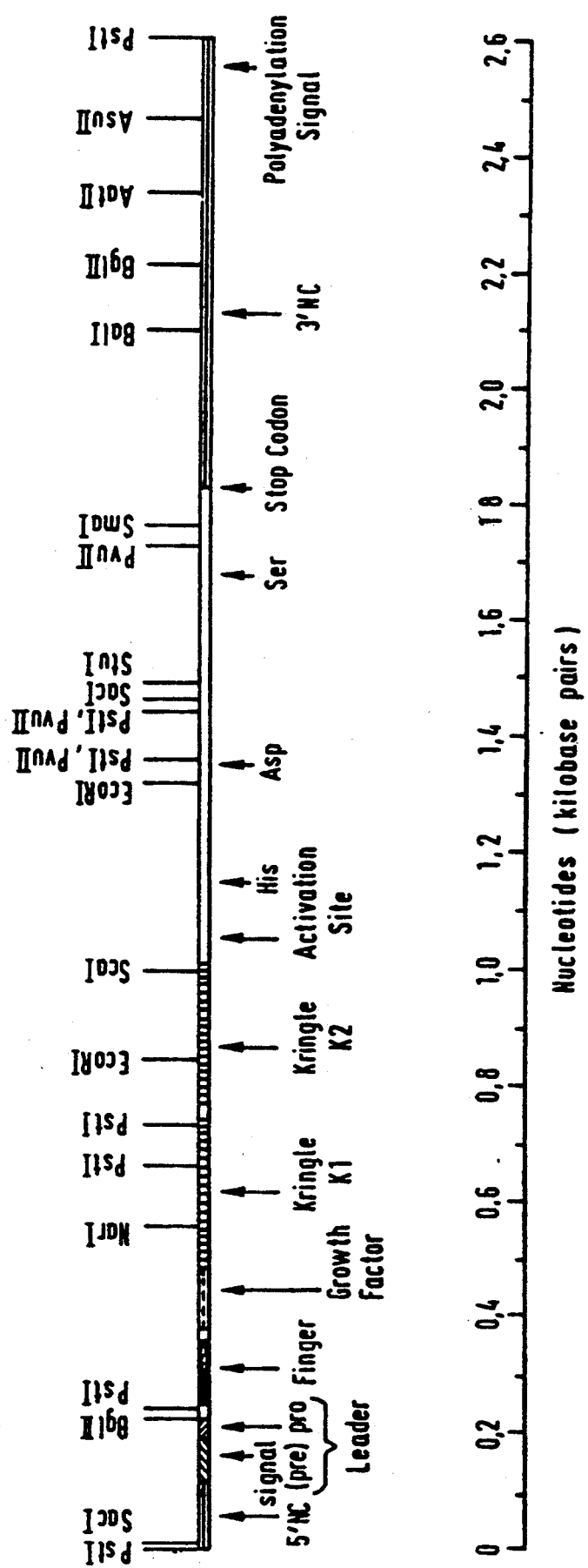
FIG. 9: RESTRICTION ENDONUCLEASE MAP OF HUMAN t-PA cDNA DERIVED FROM mRNA ISOLATED FROM HeLaS3 CELLS

FIG. 10  NUCLEOTIDE SEQUENCE AND DEDUCED AMINO ACID SEQUENCE OF u-PA cDNA INSERT PREPARED FROM Hep3 CELLS

```
  1 CCCGGGCTCCGGGCTGCGGTCTCCTGCCGCAGCCACCGAGCCGCCGTCTAGCGCCCCGA

MET ARG ALA LEU LEU ALA ARG LEU LEU LEU CYS VAL       -9
 60 CCTCGCCACC ATG AGA GCC CTG CTG GCG CGC CTG CTT CTC TGC GTC

LEU VAL VAL SER ASP SER LYS GLY SER ASN GLU LEU HIS GLN VAL    7
106 CTG GTC GTG AGC GAC TCC AAA GGC AGC AAT GAA CTT CAT CAA GTT

PRO SER ASN CYS ASP CYS LEU ASN GLY GLY THR CYS VAL SER ASN   22
151 CCA TCG AAC TGT GAC TGT CTA AAT GGA GGA ACA TGT GTG TCC AAC

LYS TYR PHE SER ASN ILE HIS TRP CYS ASN CYS PRO LYS LYS PHE   37
196 AAG TAC TTC TCC AAC ATT CAC TGG TGC AAC TGC CCA AAG AAA TTC

GLY GLY GLN HIS CYS GLU ILE ASP LYS SER LYS THR CYS TYR GLU   52
241 GGA GGG CAG CAC TGT GAA ATA GAT AAG TCA AAA ACC TGC TAT GAG

GLY ASN GLY HIS PHE TYR ARG GLY LYS ALA SER THR ASP THR MET   67
286 GGG AAT GGT CAC TTT TAC CGA GGA AAG GCC AGC ACT GAC ACC ATG

GLY ARG PRO CYS LEU PRO TRP ASN SER ALA THR VAL LEU GLN GLN   82
331 GGC CGG CCC TGC CTG CCC TGG AAC TCT GCC ACT GTC CTT CAG CAA

THR TYR HIS ALA HIS ARG SER ASP ALA LEU GLN LEU GLY LEU GLY   97
376 ACG TAC CAT GCC CAC AGA TCT GAT GCT CTT CAG CTG GGC CTG GGG

LYS HIS ASN TYR CYS ARG ASN PRO ASP ASN ARG ARG ARG PRO TRP  112
421 AAA CAT AAT TAC TGC AGG AAC CCA GAC AAC CGG AGG CGA CCC TGG

CYS TYR VAL GLN VAL GLY LEU LYS PRO LEU VAL GLN GLU CYS MET  127
466 TGC TAT GTG CAG GTG GGC CTA AAG CCG CTT GTC CAA GAG TGC ATG

VAL HIS ASP CYS ALA ASP GLY LYS LYS PRO SER SER PRO PRO GLU  142
511 GTG CAT GAC TGC GCA GAT GGA AAA AAG CCC TCC TCT CCT CCA GAA

GLU LEU LYS PHE GLN CYS GLY GLN LYS THR LEU ARG PRO ARG PHE  157
556 GAA TTA AAA TTT CAG TGT GGC CAA AAG ACT CTG AGG CCC CGC TTT

LYS ILE ILE GLY GLY GLU PHE THR THR ILE GLU ASN GLN PRO TRP  172
601 AAG ATT ATT GGG GGA GAA TTC ACC ACC ATC GAG AAC CAG CCC TGG

PHE ALA ALA ILE TYR ARG ARG HIS ARG GLY GLY SER VAL THR TYR  187
646 TTT GCG GCC ATC TAC AGG AGG CAC CGG GGG GGC TCT GTC ACC TAC

VAL CYS GLY GLY SER LEU ILE SER PRO CYS TRP VAL ILE SER ALA  202
691 GTG TGT GGA GGC AGC CTC ATC AGC CCT TGC TGG GTG ATC AGC GCC

THR HIS CYS PHE ILE ASP TYR PRO LYS LYS GLU ASP TYR ILE VAL  217
736 ACA CAC TGC TTC ATT GAT TAC CCA AAG AAG GAG GAC TAC ATC GTC
```

FIG. 10 (CONTINUATION)

```
         TYR LEU GLY ARG SFR ARG LEU ASN SER ASN THR GLN GLY GLU MET    232
    781  TAC CTG GGT CGC TCA AGG CTT AAC TCC AAC ACG CAA GGG GAG ATG

LYS PHE GLU VAL GLU ASN LEU ILE LEU HIS LYS ASP TYR SER ALA    247
    826  AAG TTT GAG GTG GAA AAC CTC ATC CTA CAC AAG GAC TAC AGC GCT

ASP THR LEU ALA HIS HIS ASN ASP ILE ALA LEU LEU LYS ILE ARG    262
    871  GAC ACG CTT GCT CAC CAC AAC GAC ATT GCC TTG CTG AAG ATC CGT

SER LYS GLU GLY ARG CYS ALA GLN PRO SER ARG THR ILE GLN THR    277
    916  TCC AAG GAG GGC AGG TGT GCG CAG CCA TCC CGG ACT ATA CAG ACC

ILE CYS LEU PRO SER MET TYR ASN ASP PRO GLN PHE GLY THR SER    292
    961  ATC TGC CTG CCC TCG ATG TAT AAC GAT CCC CAG TTT GGC ACA AGC

CYS GLU ILE THR GLY PHE GLY LYS GLU ASN SER THR ASP TYR LEU    307
   1006  TGT GAG ATC ACT GGC TTT GGA AAA GAG AAT TCT ACC GAC TAT CTC

TYR PRO GLU GLN LEU LYS MET THR VAL VAL LYS LEU ILE SER HIS    322
   1051  TAT CCG GAG CAG CTG AAA ATG ACT GTT GTG AAG CTG ATT TCC CAC

ARG GLU CYS GLN GLN PRO HIS TYR TYR GLY SER GLU VAL THR THR    337
   1096  CGG GAG TGT CAG CAG CCC CAC TAC TAC GGC TCT GAA GTC ACC ACC

LYS MET LEU CYS ALA ALA ASP PRO GLN TRP LYS THR ASP SER CYS    352
   1141  AAA ATG CTA TGT GCT GCT GAC CCA CAA TGG AAA ACA GAT TCC TGC

GLN GLY ASP SER GLY GLY PRO LEU VAL CYS SER LEU GLN GLY ARG    367
   1186  CAG GGA GAC TCA GGG GGA CCC CTC GTC TGT TCC CTC CAA GGC CGC

MET THR LEU THR GLY ILE VAL SER TRP GLY ARG GLY CYS ALA LEU    382
   1231  ATG ACT TTG ACT GGA ATT GTG AGC TGG GGC CGT GGA TGT GCC CTG

LYS ASP LYS PRO GLY VAL TYR THR ARG VAL SER HIS PHE LEU PRO    397
   1276  AAG GAC AAG CCA GGC GTC TAC ACG AGA GTC TCA CAC TTC TTA CCC

TRP ILE ARG SER HIS THR LYS GLU GLU ASN GLY LEU ALA LEU        411
   1321  TGG ATC CGC AGT CAC ACC AAG GAA GAG AAT GGC CTG GCC CTC TGA

1366  GGGTCCCCAGGGAGGAAACGGGCACCACCCGCTTTCTTGCTGGTTGTCATTTTTGCAGTA

1426  GAGTCATCTCCATCAGCTGTAAGAAGAGACTGGGAAGATAGGCTCTGCACAGATGGATTT

1486  GCCTGTGCCACCCACCAGGGTGAACGACAATAGCTTTACCCTCAGGCATAGGCCTGGGTG

1546  CTGGCTGCCCAGACCCCTCTGGCCAGGATGGAGGGGTGGTCCTGACTCAACATGTTACTG

1606  ACCAGCAACTTGTCTTTTTCTGGACTGAAGCCTGCAGGAGTTAAAAAGGGCAGGGCATCT

1666  CCTGTGCATGGGTGAAGGGAGAGCCAGCTCCCCCGACGGTGGGCATTTGTGAGGCCCATG

1726  GTTGAGAAATGAATAATTTCCCAATTAGGAAGTGTAACAGCTGAGGTCTCTTGAGGGAGC
```

FIG. 10 (CONTINUATION)

```
1786 TTAGCCAATGTGGGAGCAGCGGTTTGGGGAGCAGAGACACTAACGACTTCAGGGCAGGGC

1846 TCTGATATTCCATGAATGTATCAGGAAATATATATGTGTGTGTATGTTTGCACACTTGTG

1906 TGTGGGCTGTGAGTGTAAGTGTGAGTAAGAGCTGGTGTCTGATTGTTAAGTCTAAATATT

1966 TCCTTAAACTGTGTGGACTGTGATGCCACACAGAGTGGTCTTTCTGGAGAGGTTATAGGT

2026 CACTCCTGGGGCCTCTTGGGTCCCCCACGTGACAGTGCCTGGGAATGTATTATTCTGCAG

2086 CATGACCTGTGACCAGCACTGTCTCAGTTTCACTTTCACATAGATGTCCCTTTCTTGGCC

2146 AGTTATCCCTTCCTTTTAGCCTAGTTCATCCAATCCTCACTGGGTGGGGTGAGGACCACT

2206 CCTTACACTGAATATTTATATTTCACTATTTTTATTTATATTTTTGTAATTTTAAATAAA

2266 AGTGATCAATAAAATGTGATTTTCTG(A)n
```

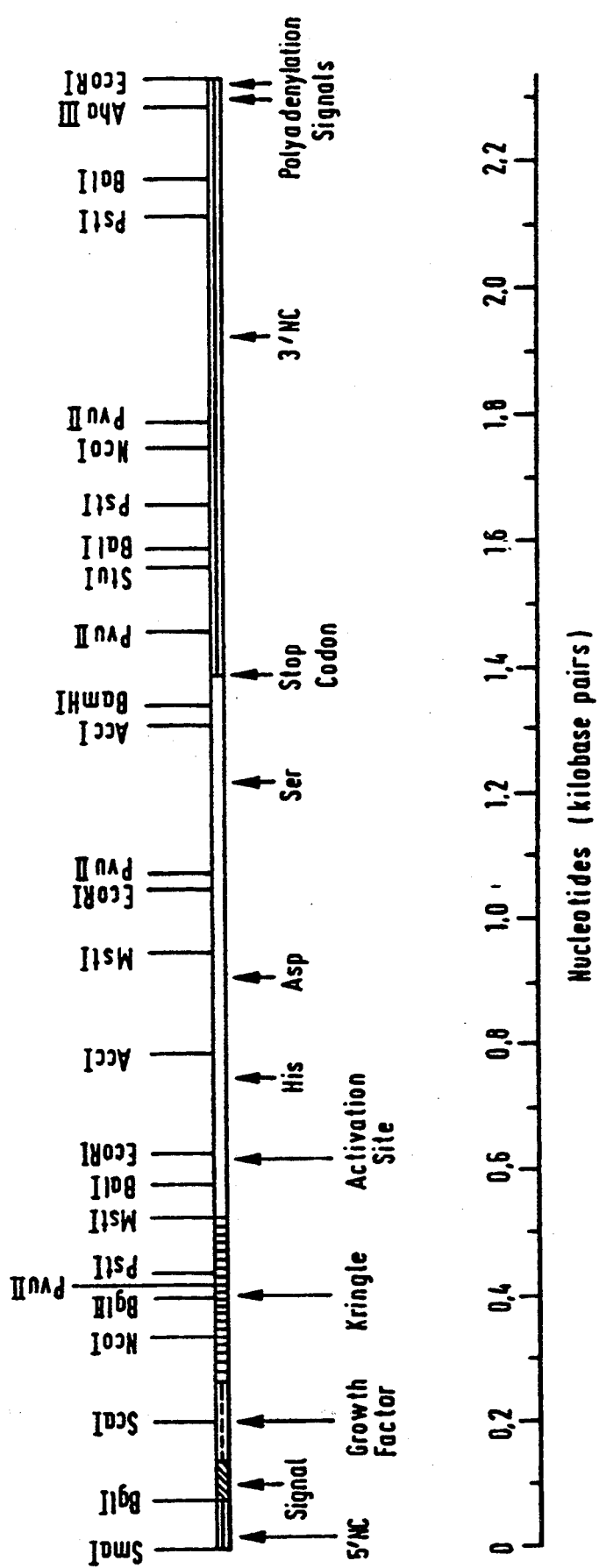
FIG.11: RESTRICTION ENDONUCLEASE MAP OF HUMAN u-PA cDNA DERIVED FROM mRNA ISOLATED FROM Hep3 CELLS

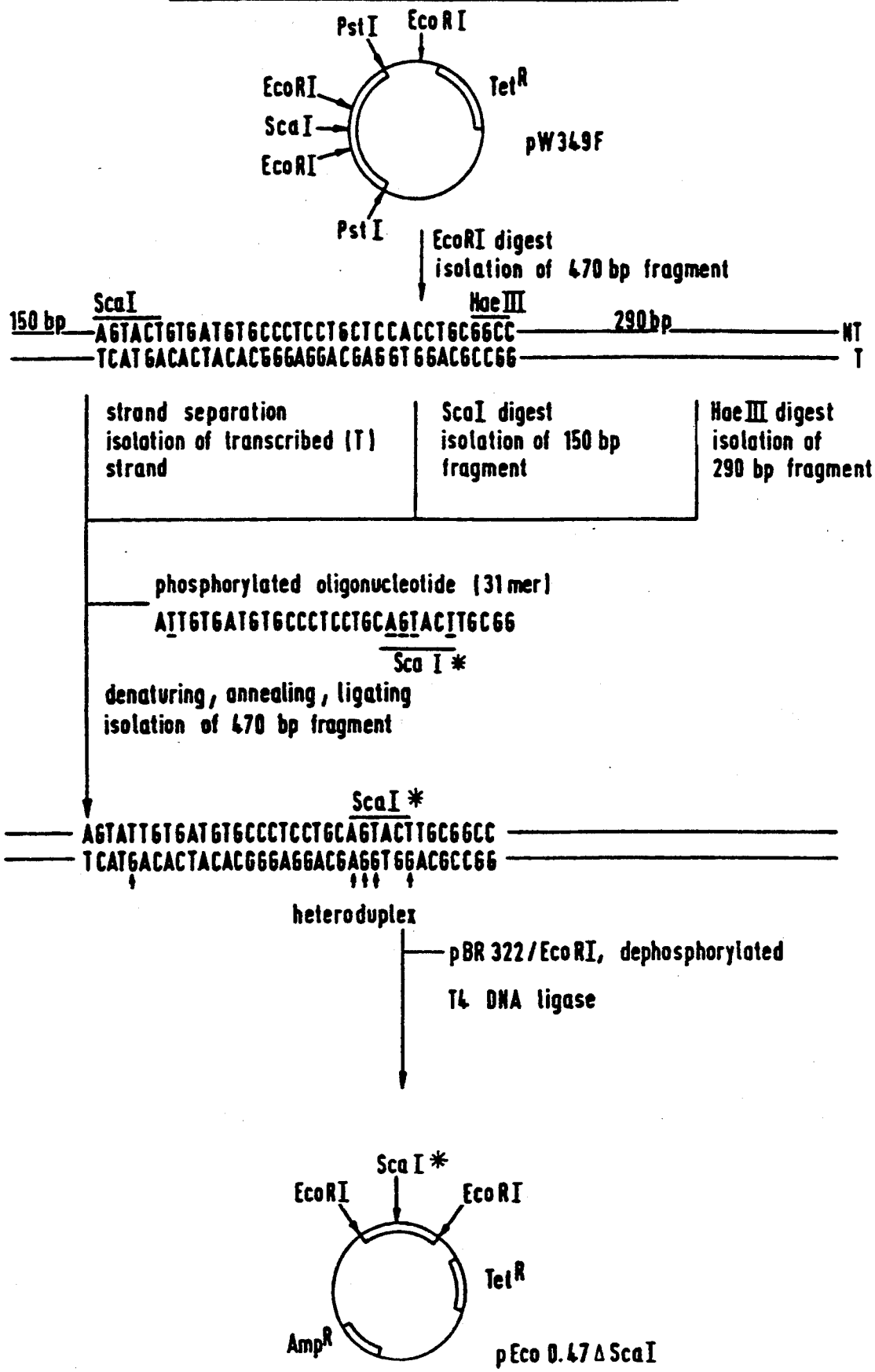
FIG. 12: PREPARATION OF PLASMID pEco 0.47△ScaI

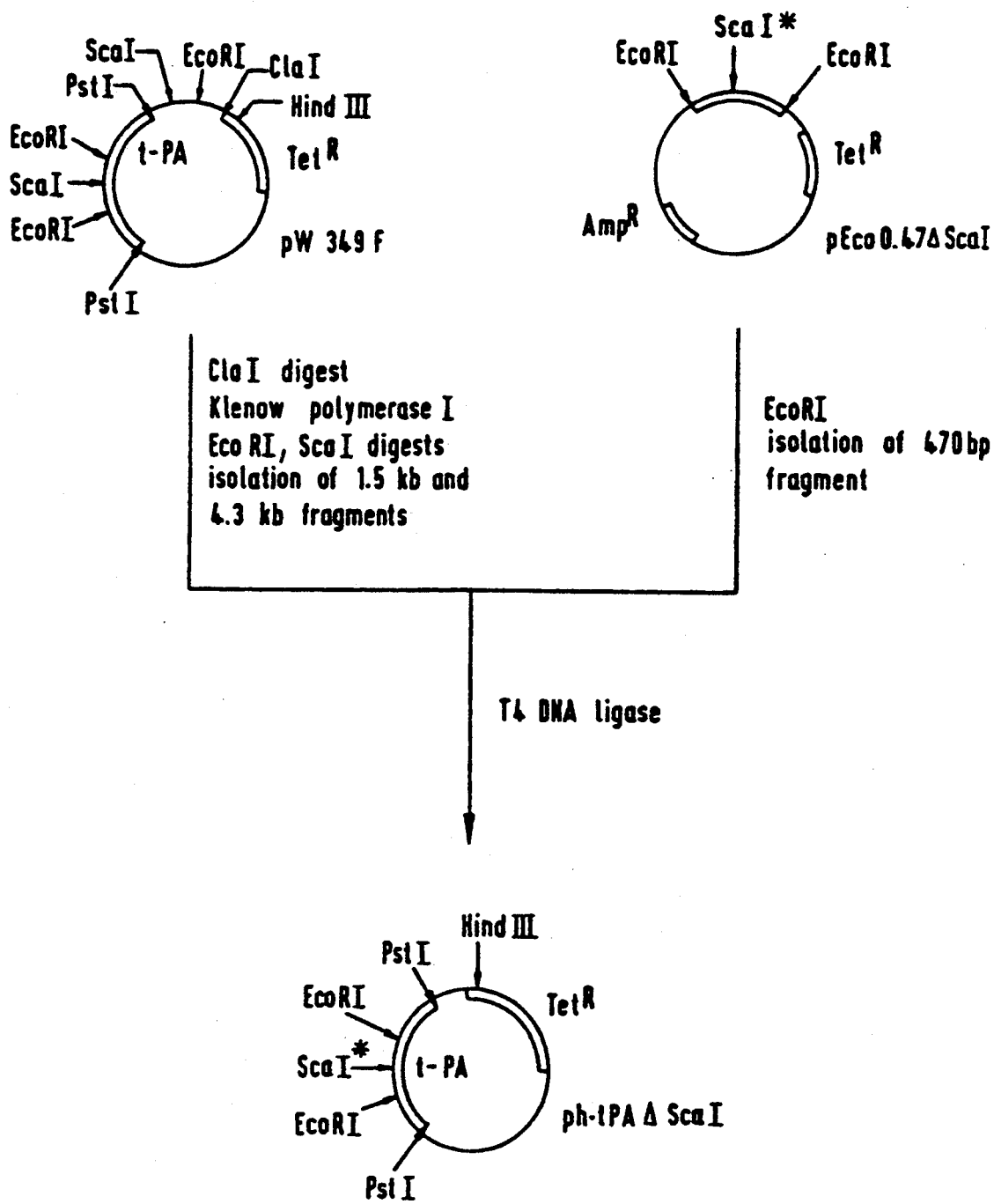

FIG. 14: CONSTRUCTION OF PLASMID pUNC·tc
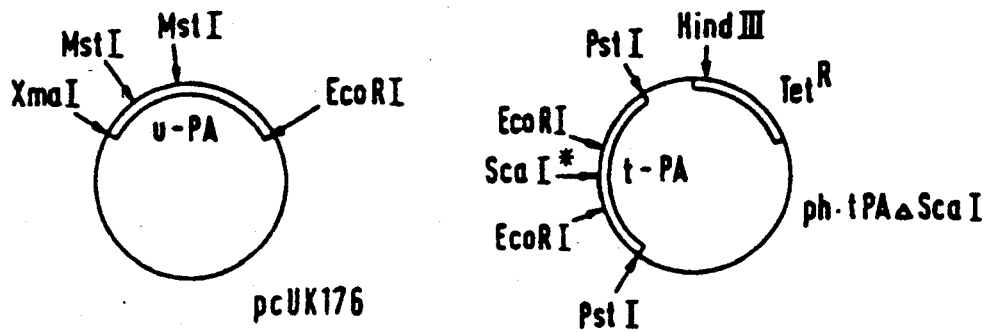
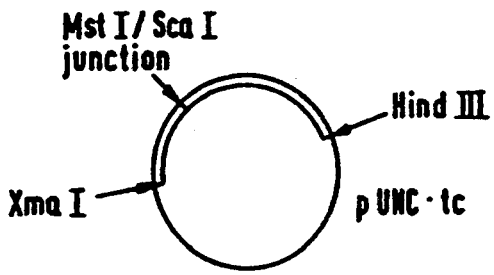
Sequence at the junction of u-PA and t-PA DNAs:
```
aa    126               131 263              268
      CYS MET VAL HIS ASP CYS THR CYS GLY LEU ARG GLN
      TGC ATG GTG CAT GAC TGC ACT TGC GGC CTG AGA CAG
      ←──────── u-PA ────────┼──────── t-PA ────────→
```

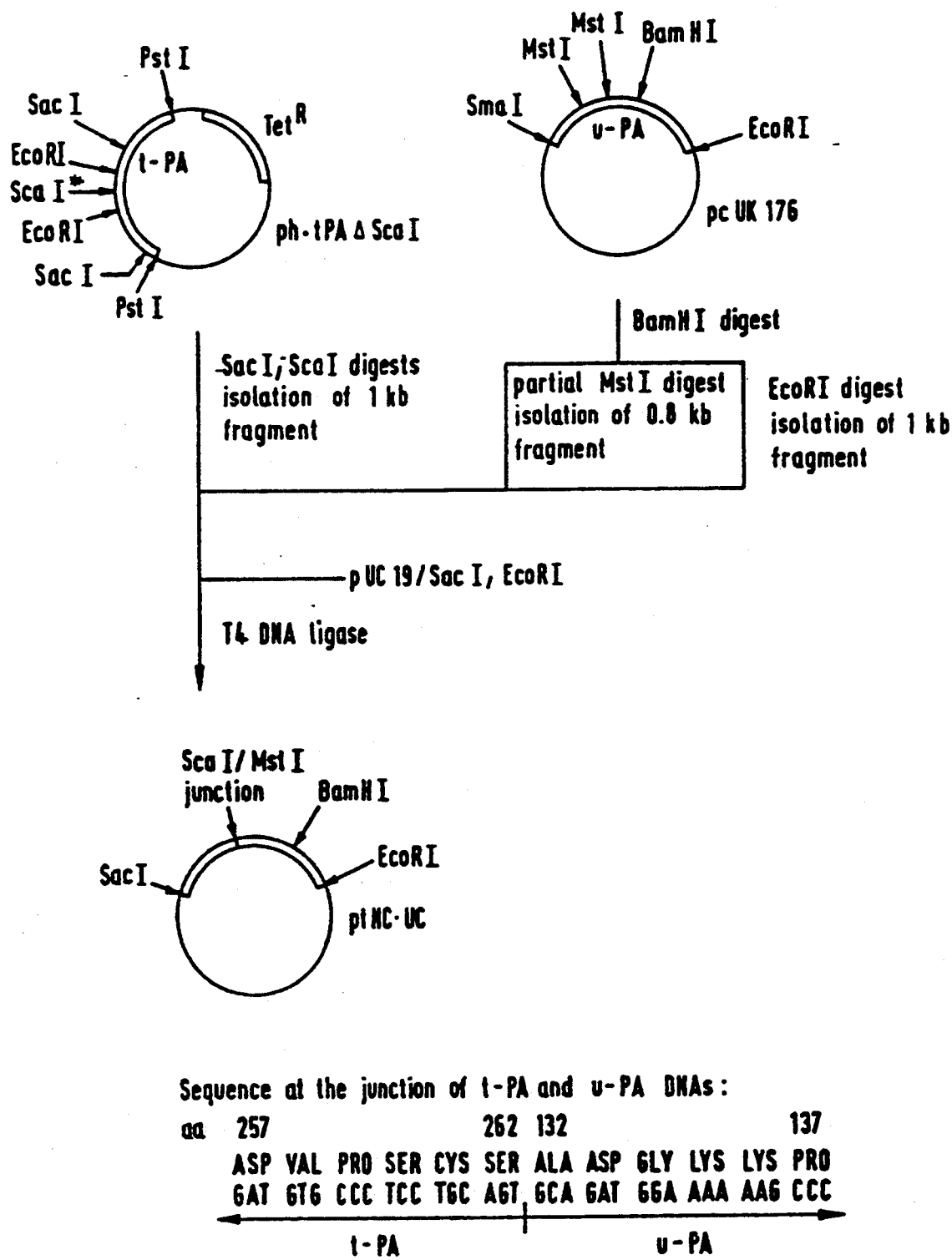
FIG.15: CONSTRUCTION OF PLASMID ptNC-UC

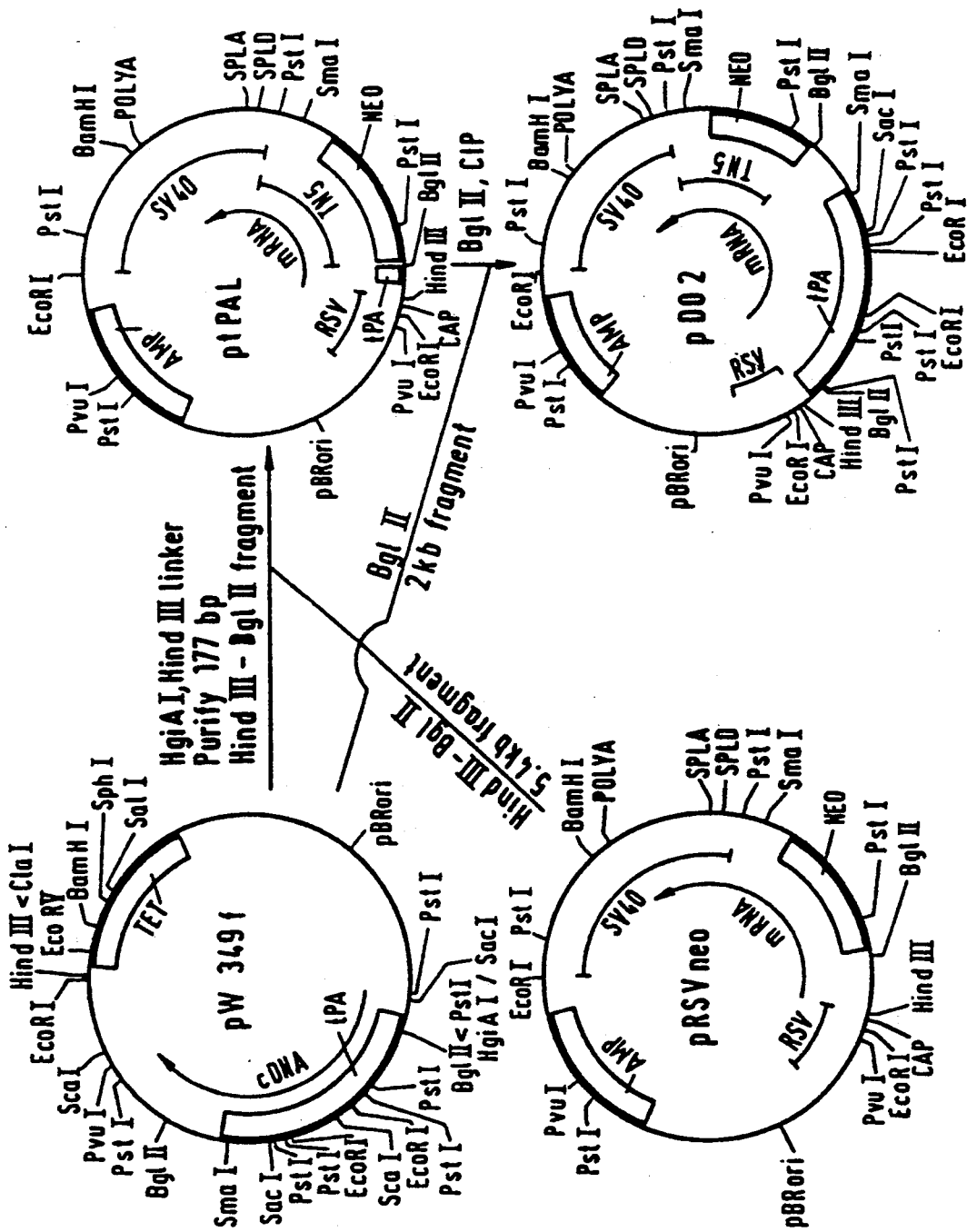

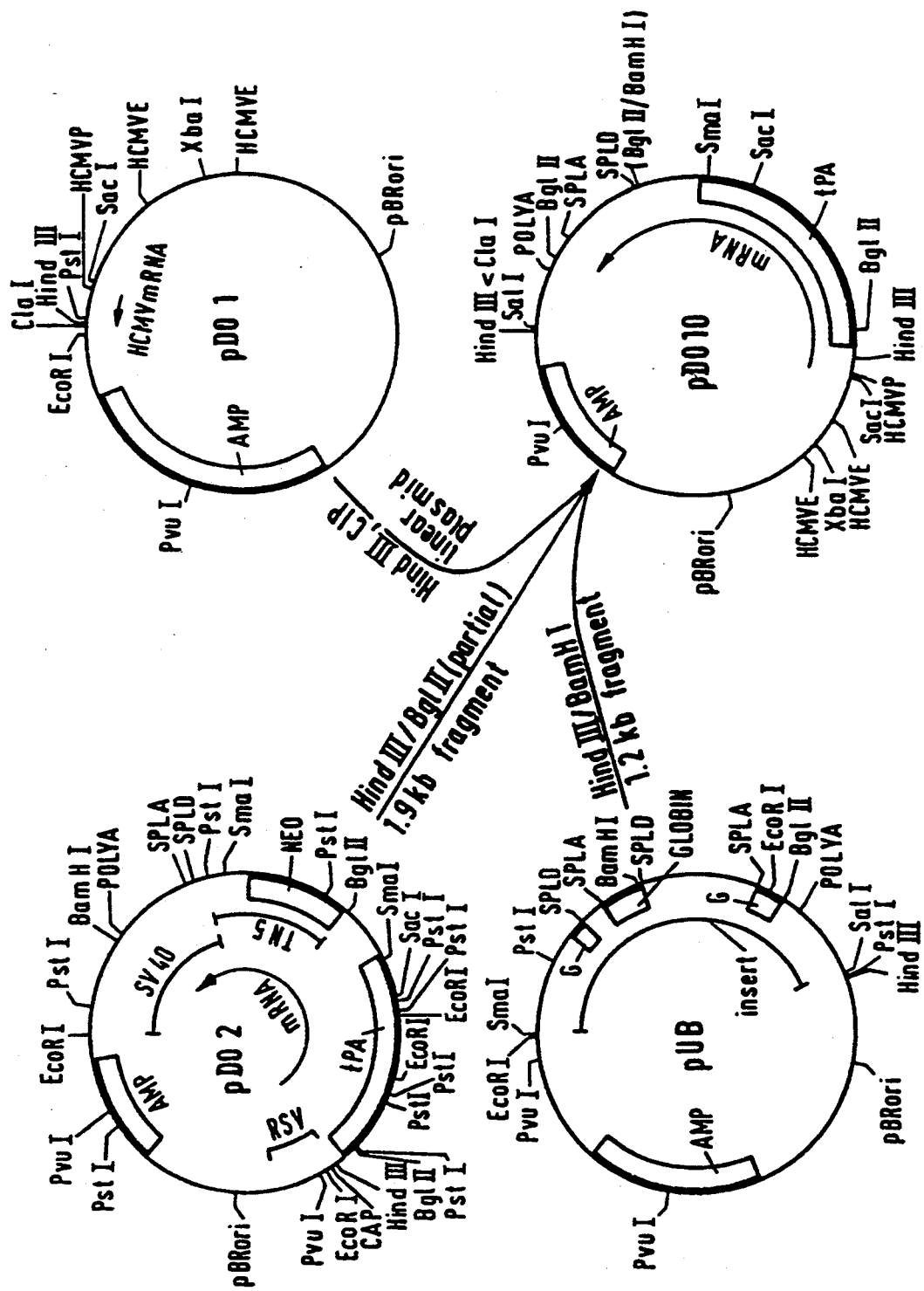
FIG.17: CONSTRUCTION OF PLASMID pDO10

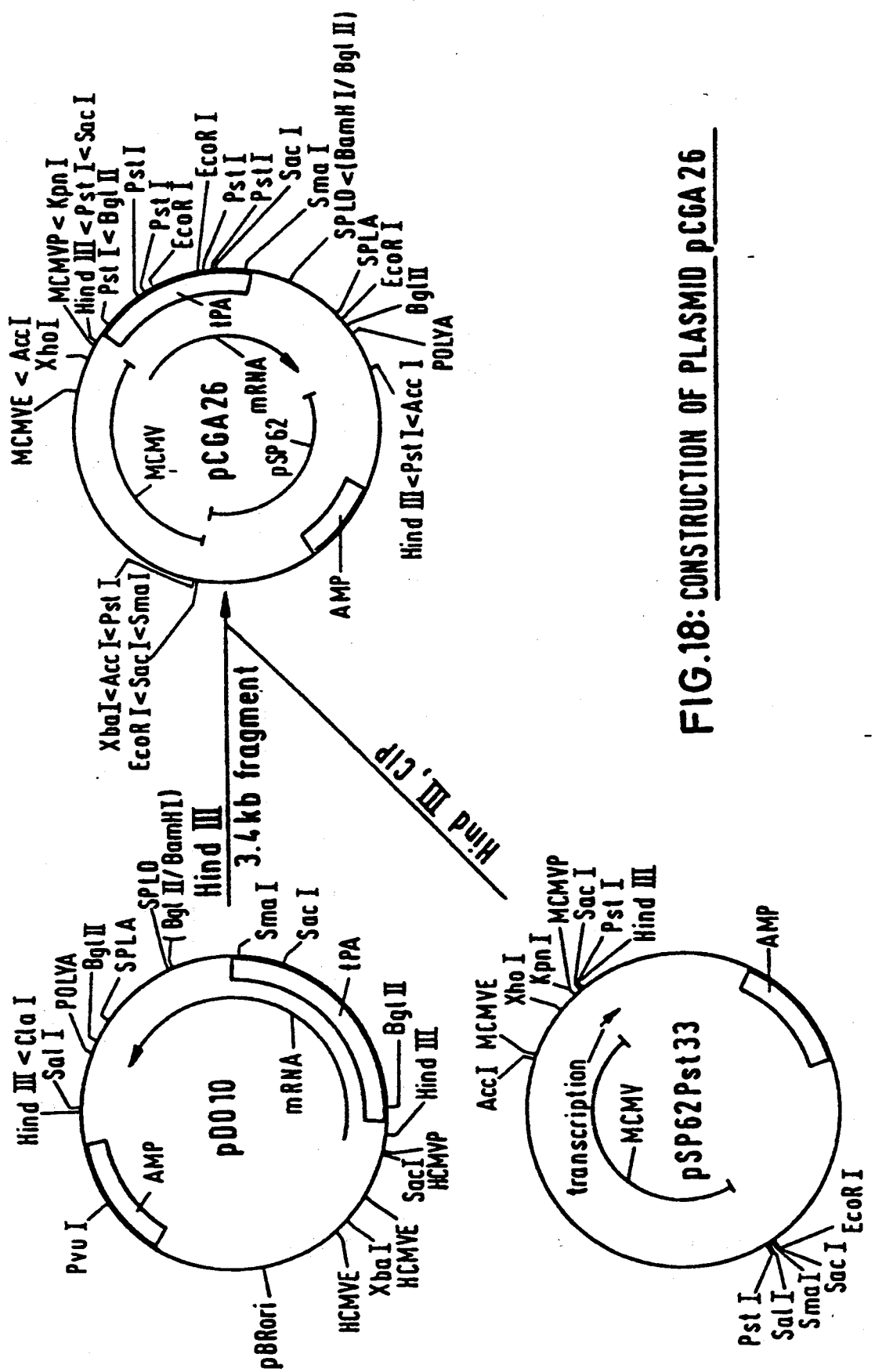
FIG. 18: CONSTRUCTION OF PLASMID pCGA26

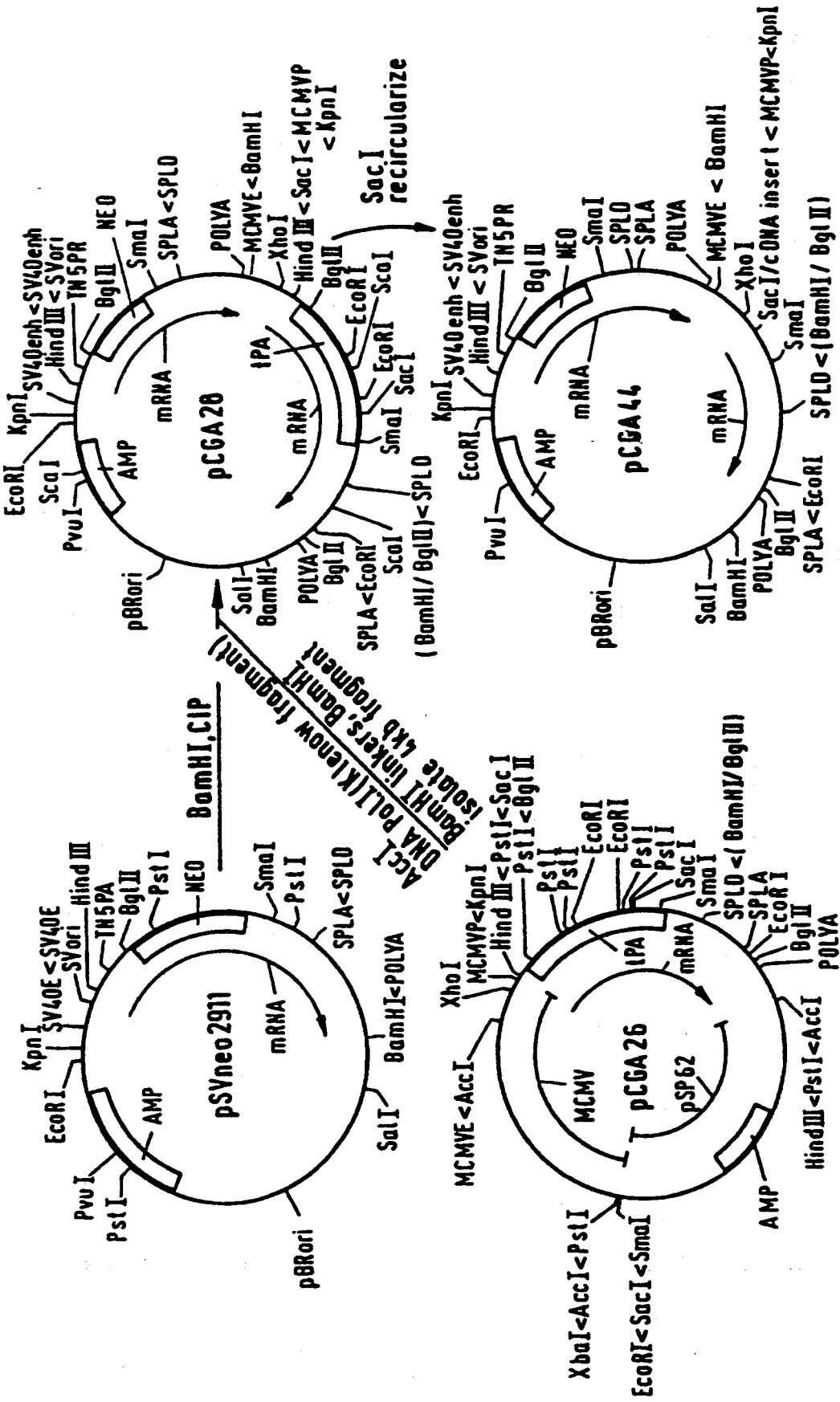
FIG. 19: CONSTRUCTION OF PLASMIDS pCGA28 AND pCGA44.

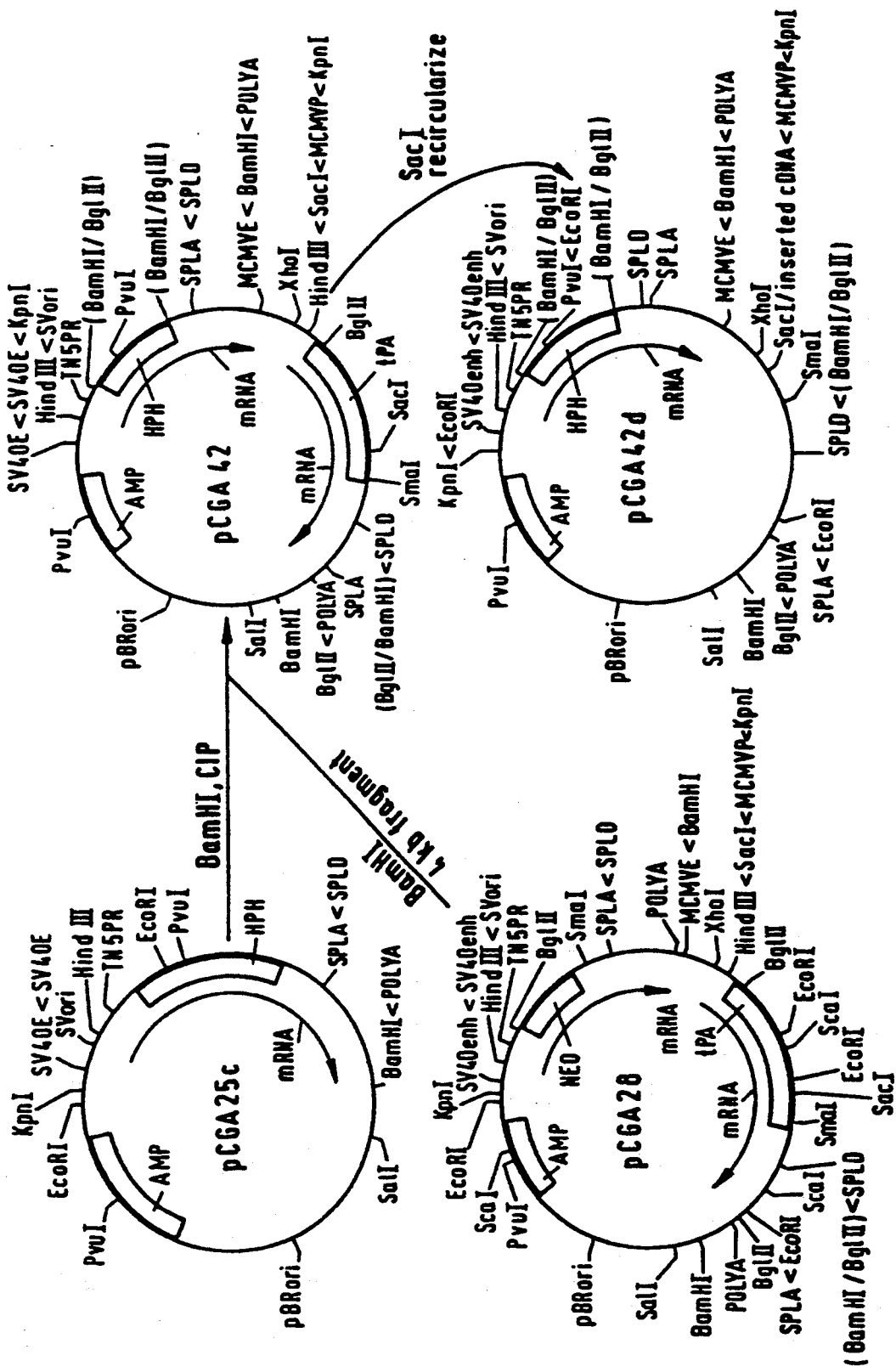
FIG. 20: CONSTRUCTION OF PLASMIDS pCGA42 AND pCGA42d

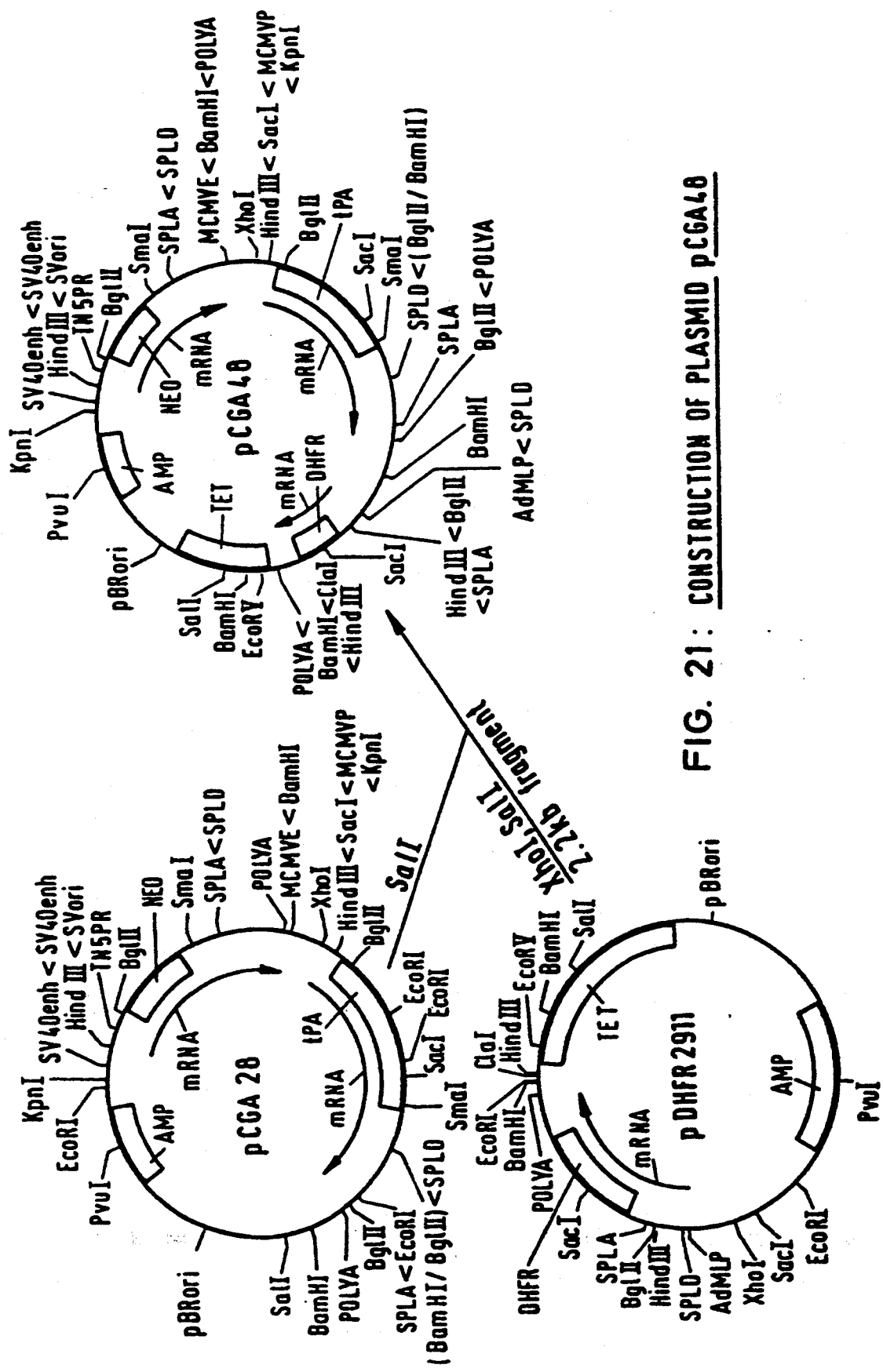
FIG. 21: CONSTRUCTION OF PLASMID pCGA48

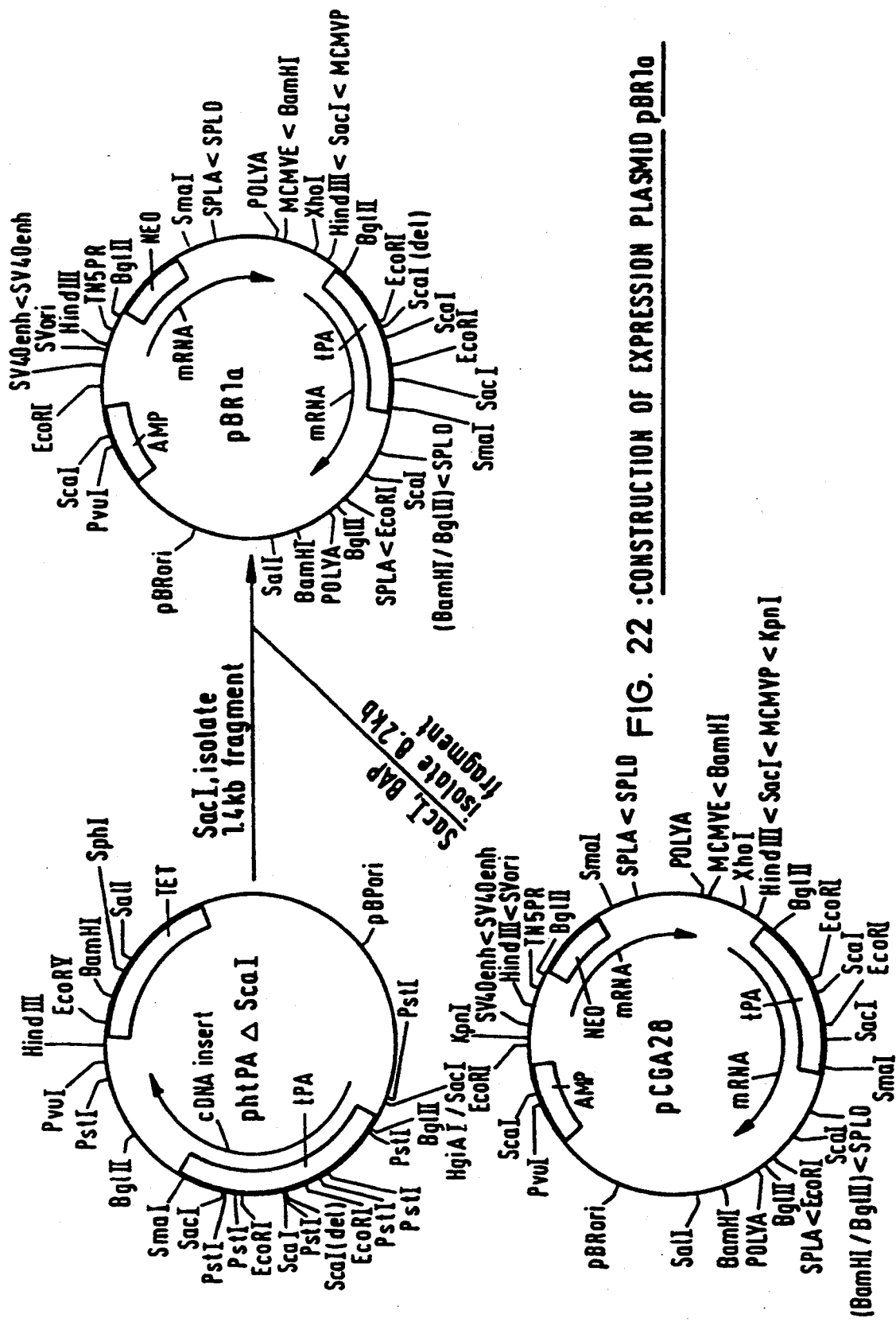
FIG. 22: CONSTRUCTION OF EXPRESSION PLASMID pBR1a

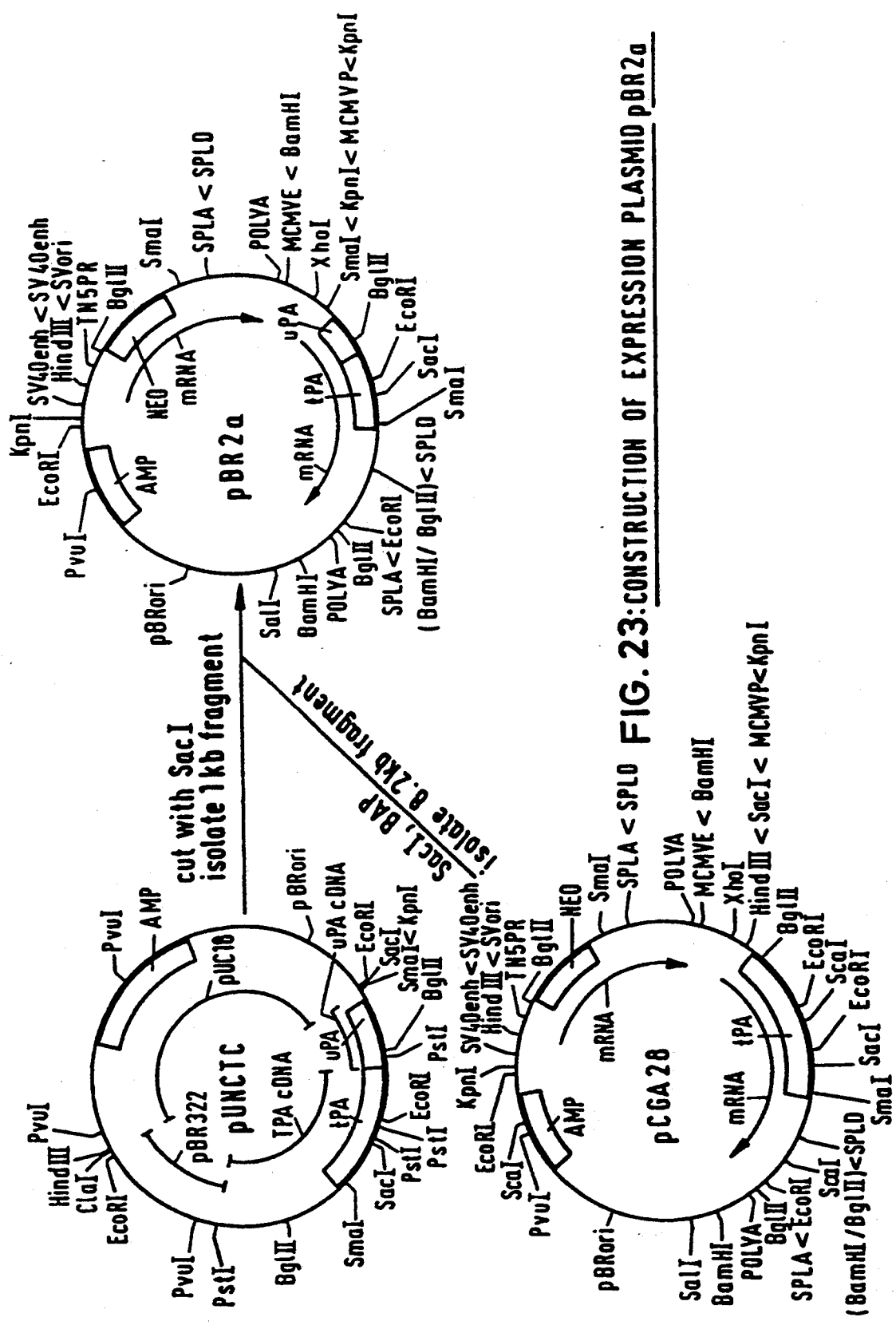

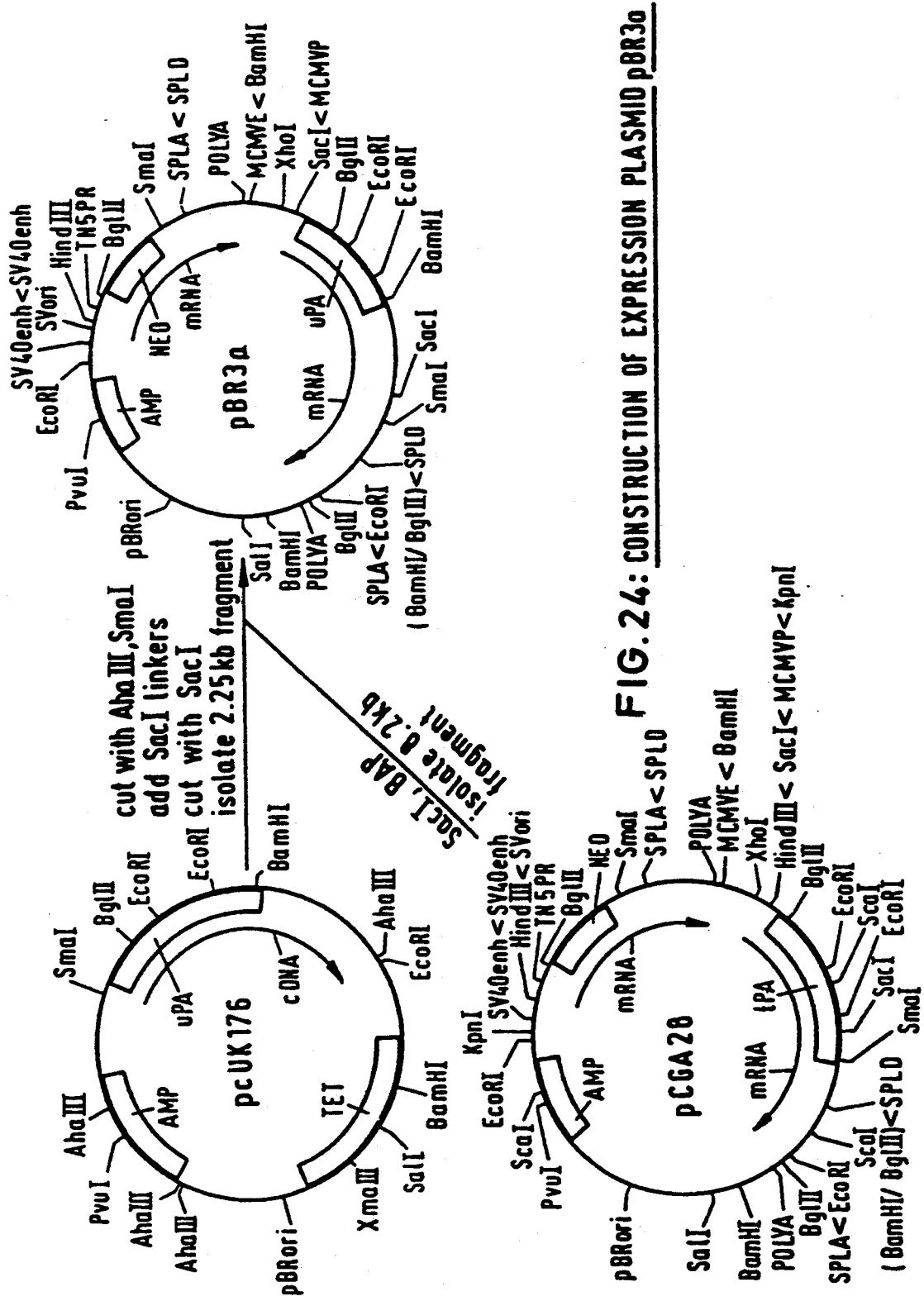
FIG. 24: CONSTRUCTION OF EXPRESSION PLASMID pBR3a

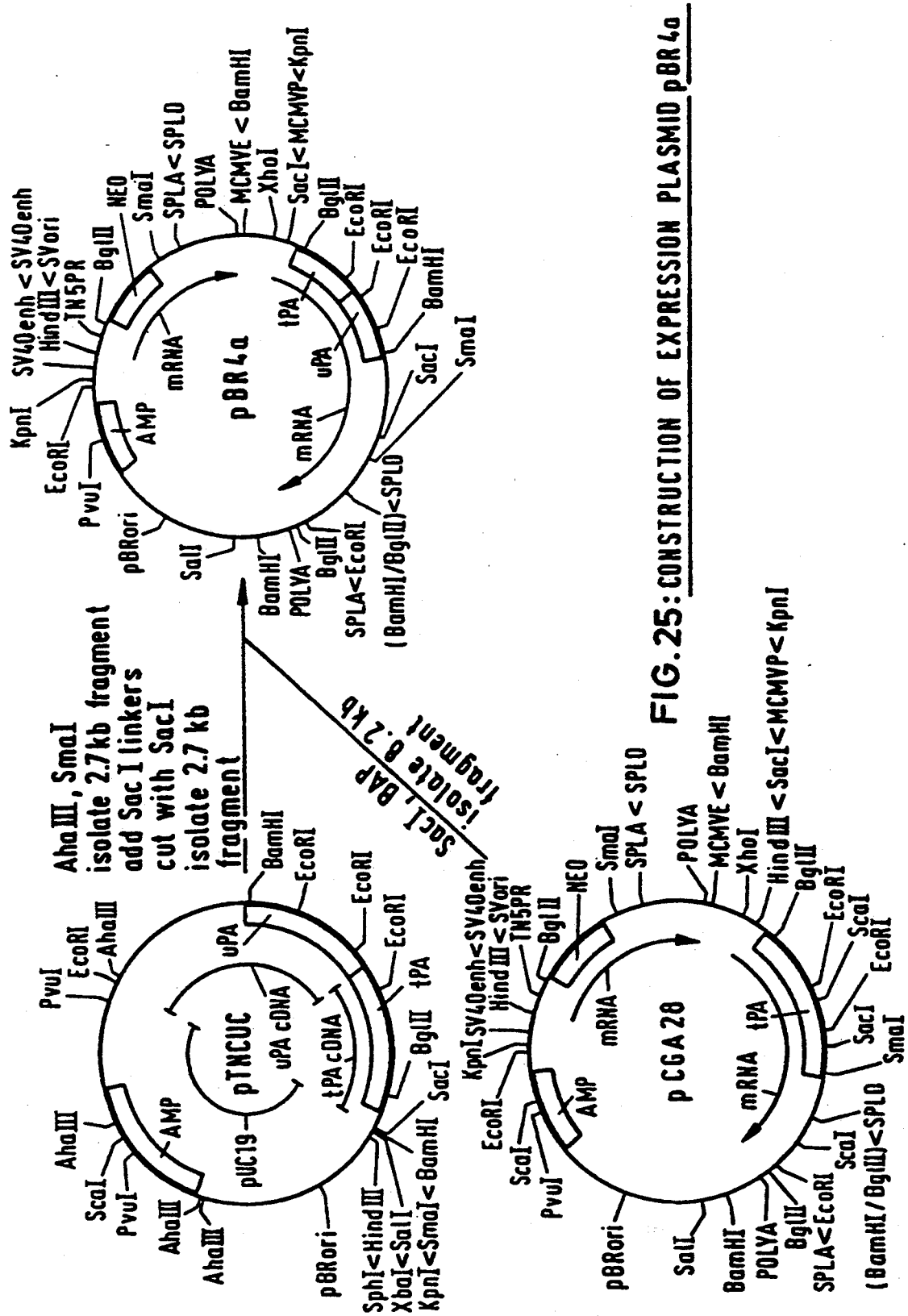
FIG. 25: CONSTRUCTION OF EXPRESSION PLASMID pBR4a

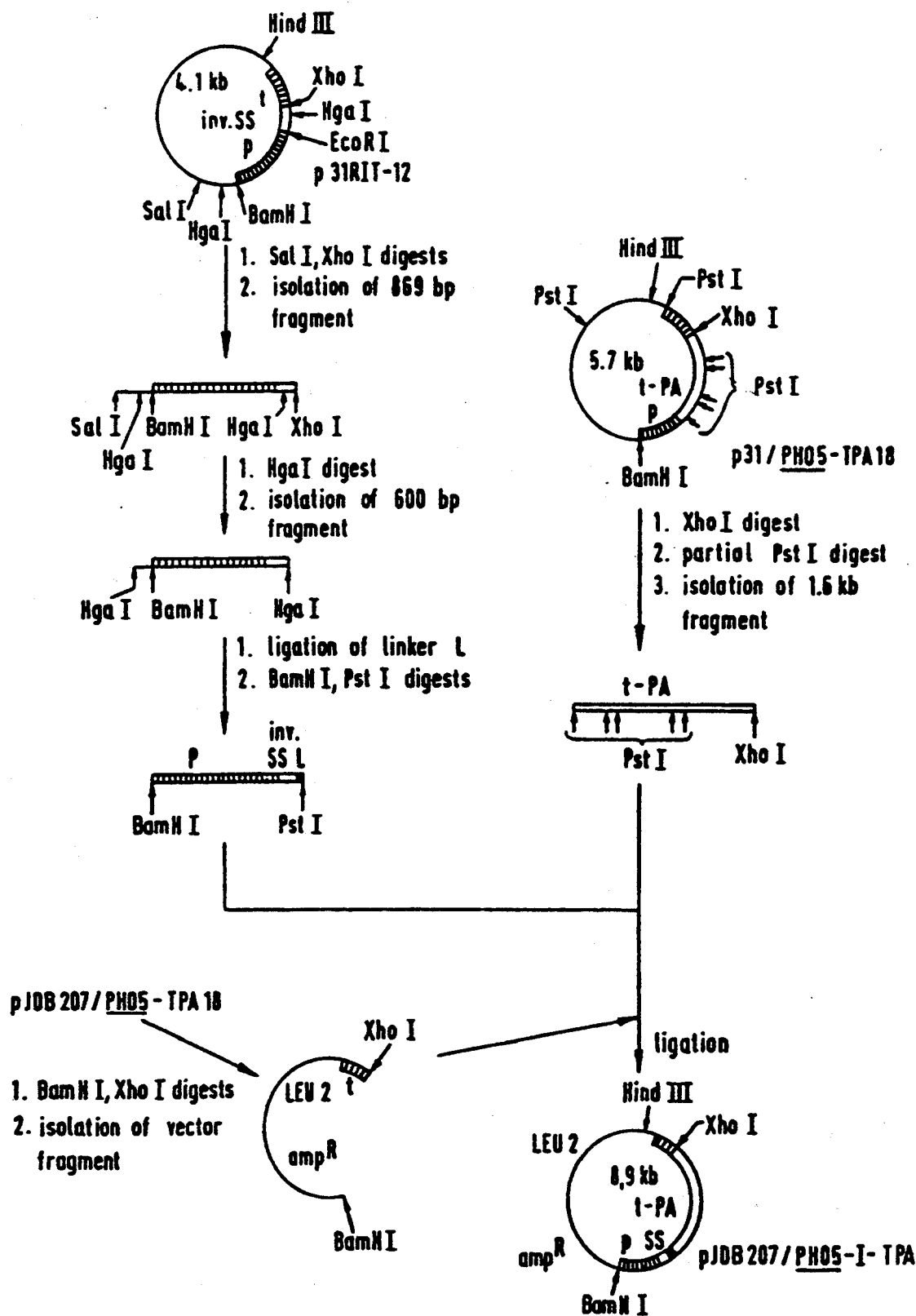
FIG. 26: CONSTRUCTION OF pJDB207/PHO5-I-TPA

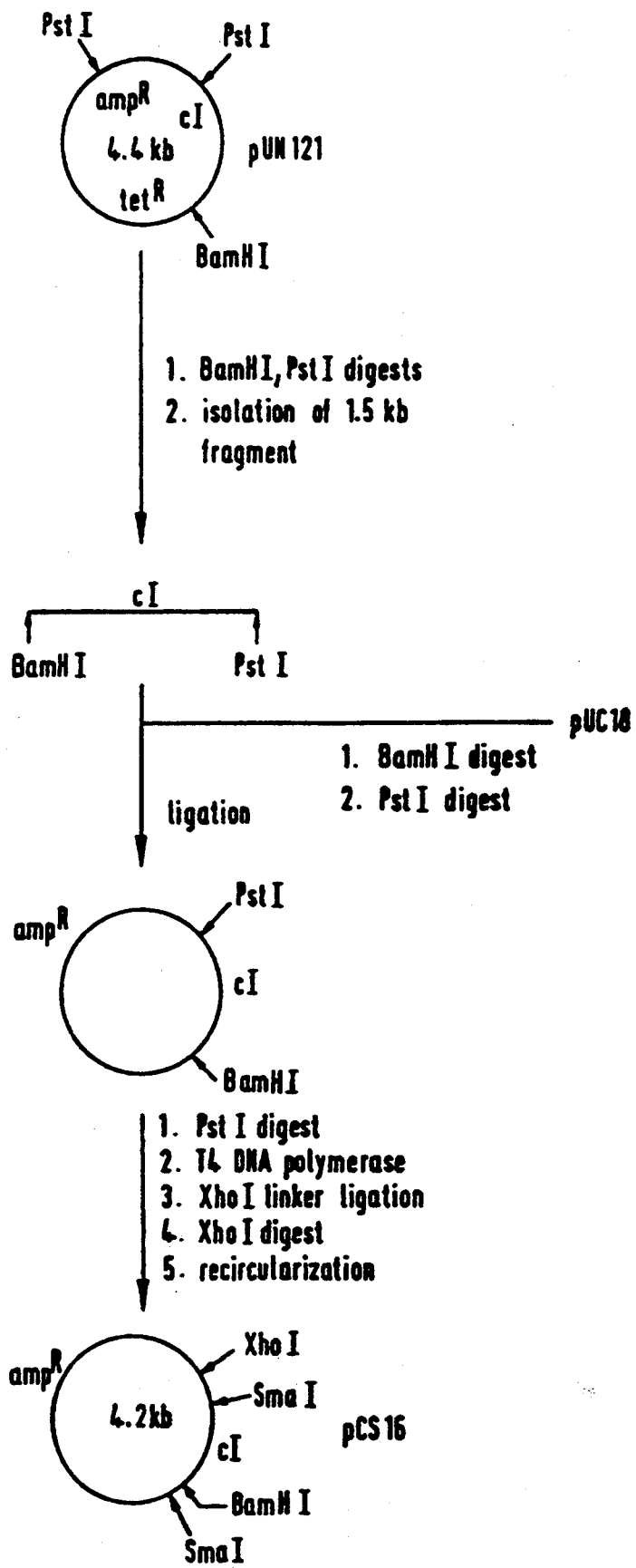
FIG. 27: CONSTRUCTION OF PLASMID pCS16

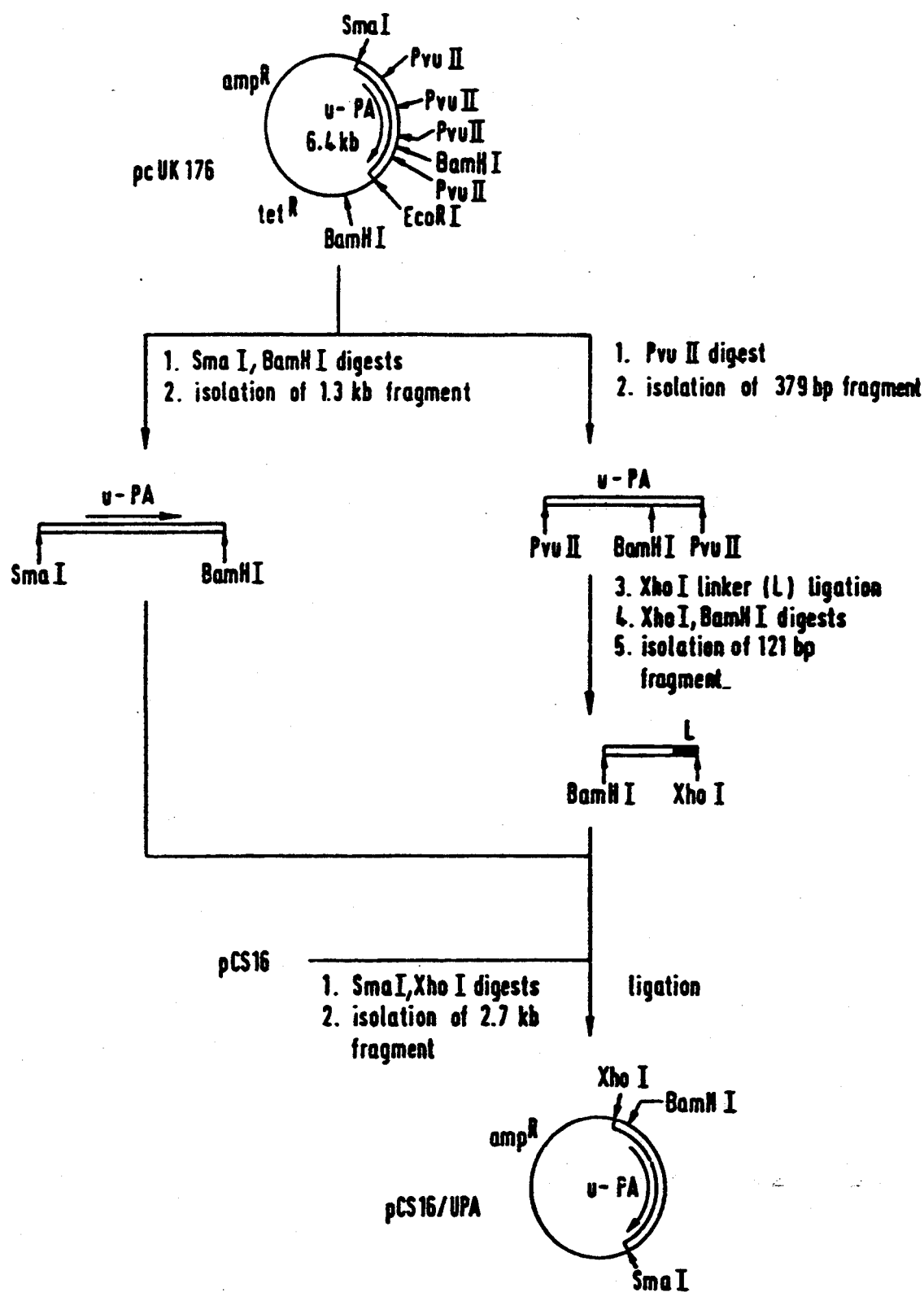
FIG. 28: CONSTRUCTION OF PLASMID pCS16/UPA

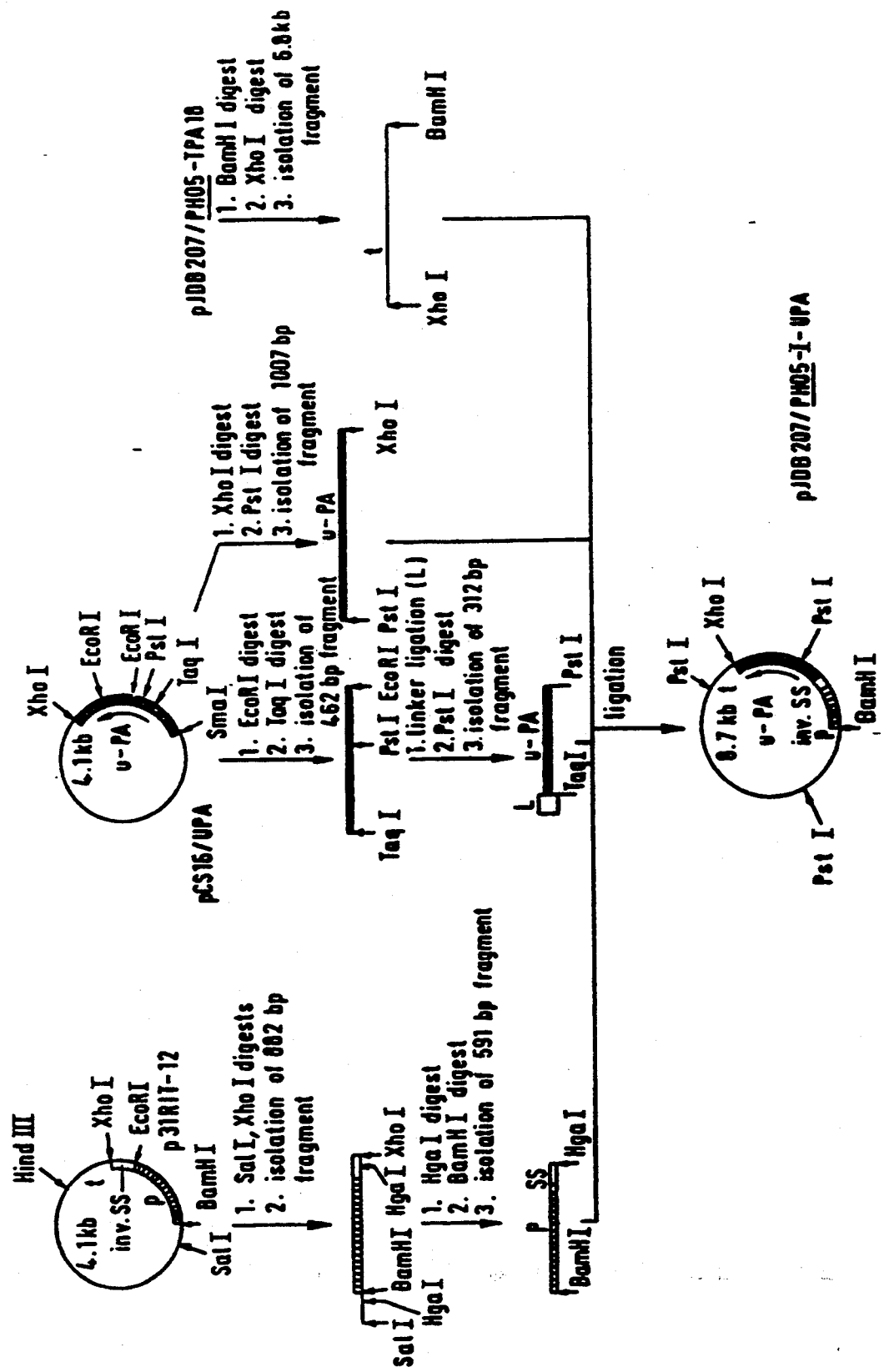

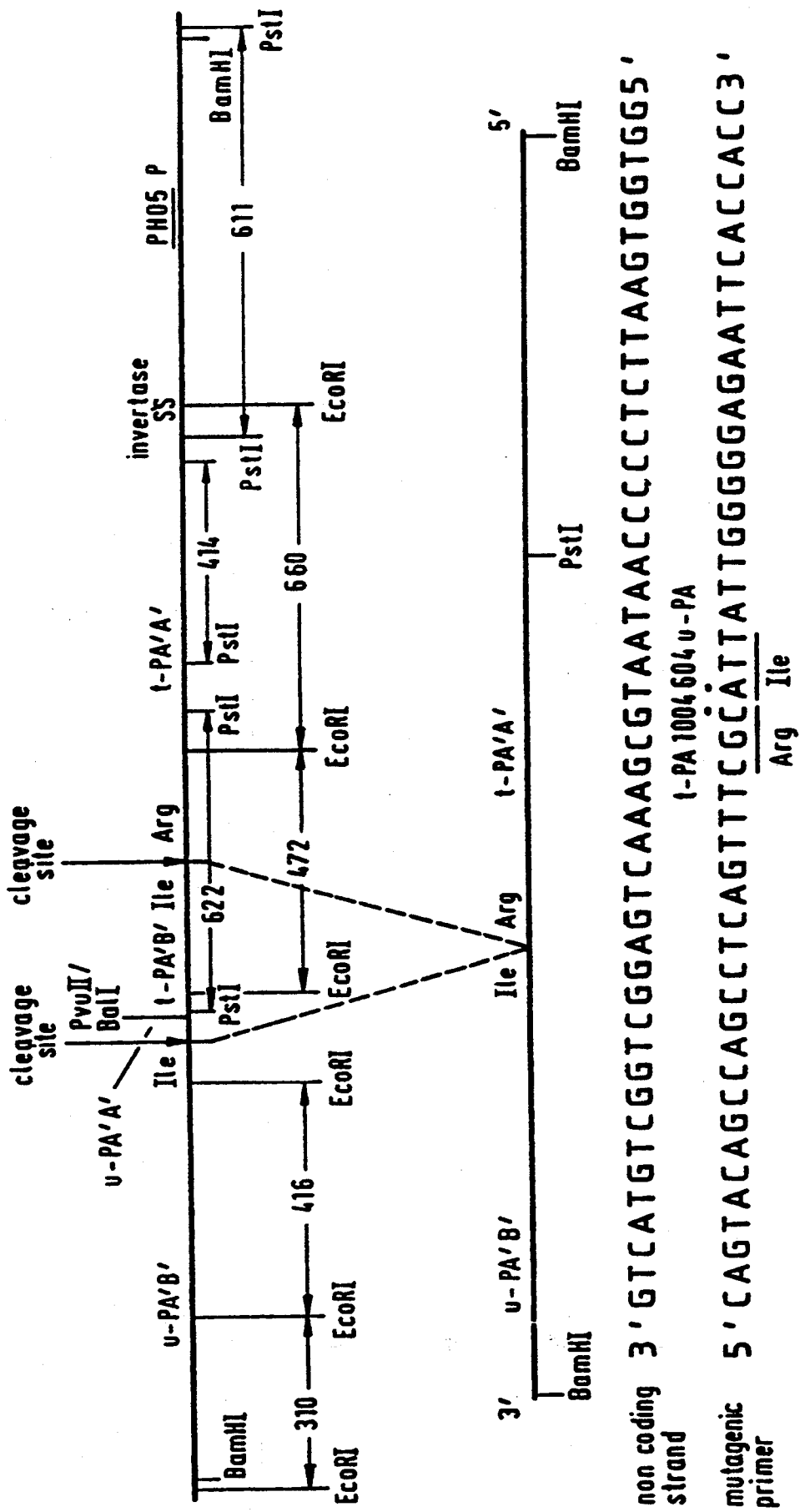
FIG. 30. DELETION MUTAGENESIS ON mp18/BamHI/TPA^A UPA^B

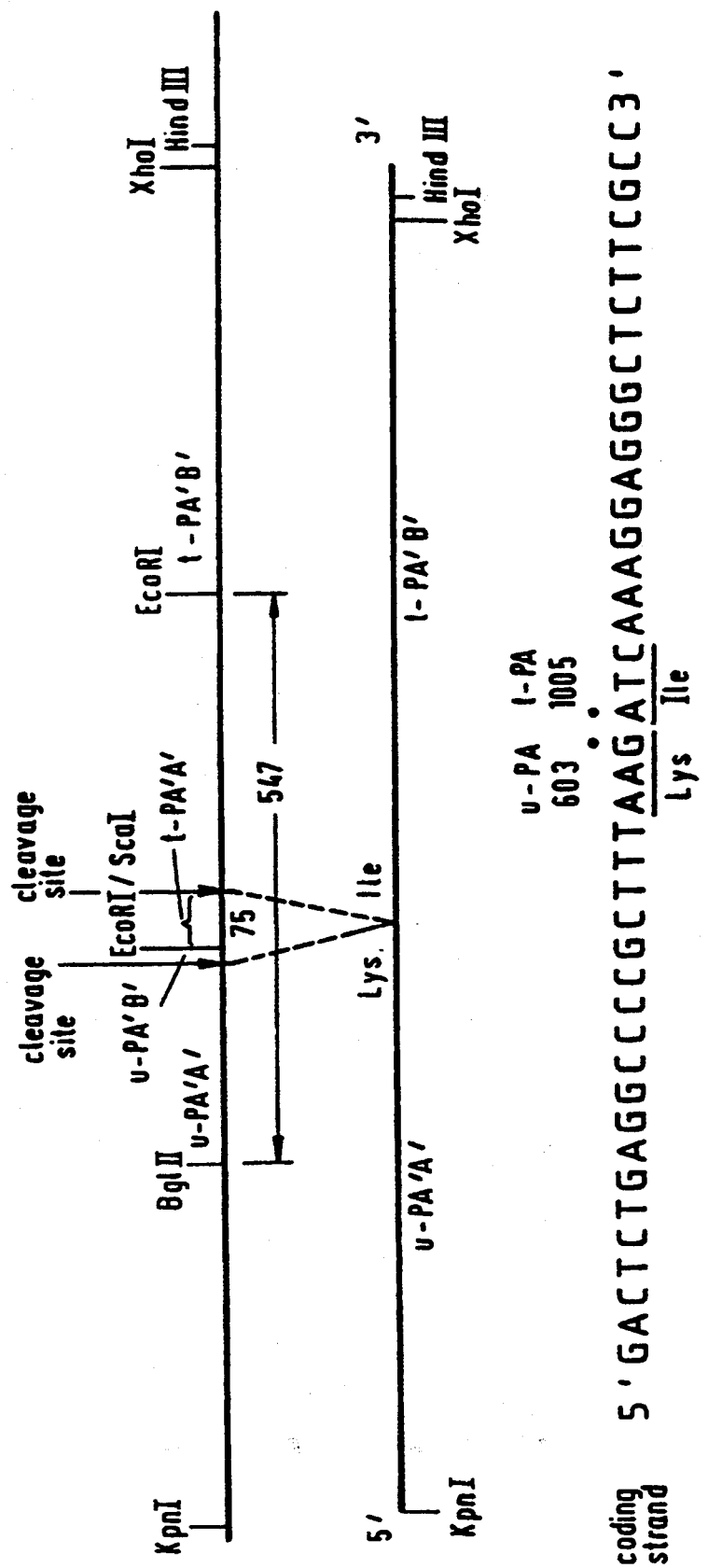
FIG.31: DELETION MUTAGENESIS ON mp18/KpnI-HindIII/UPA$^A$ TPA$^B$

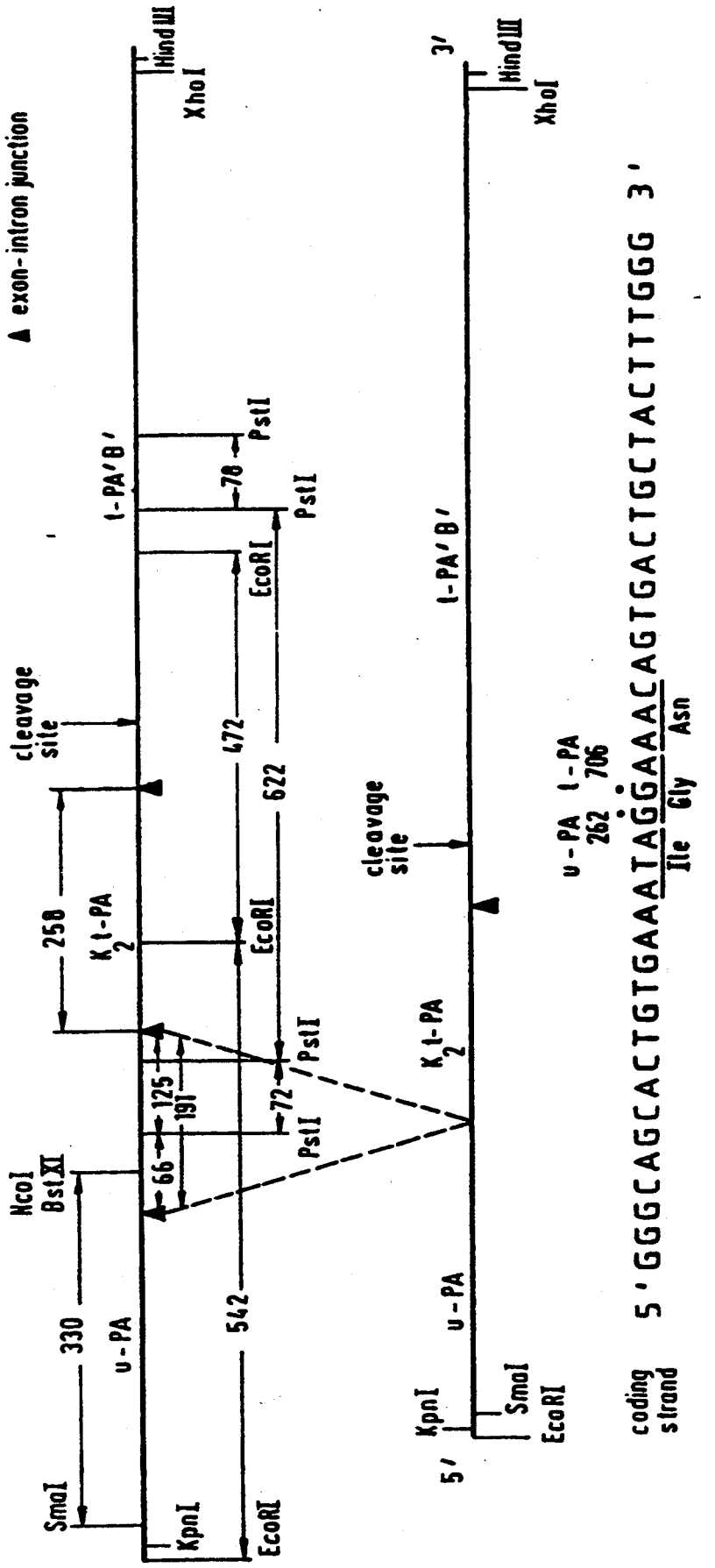

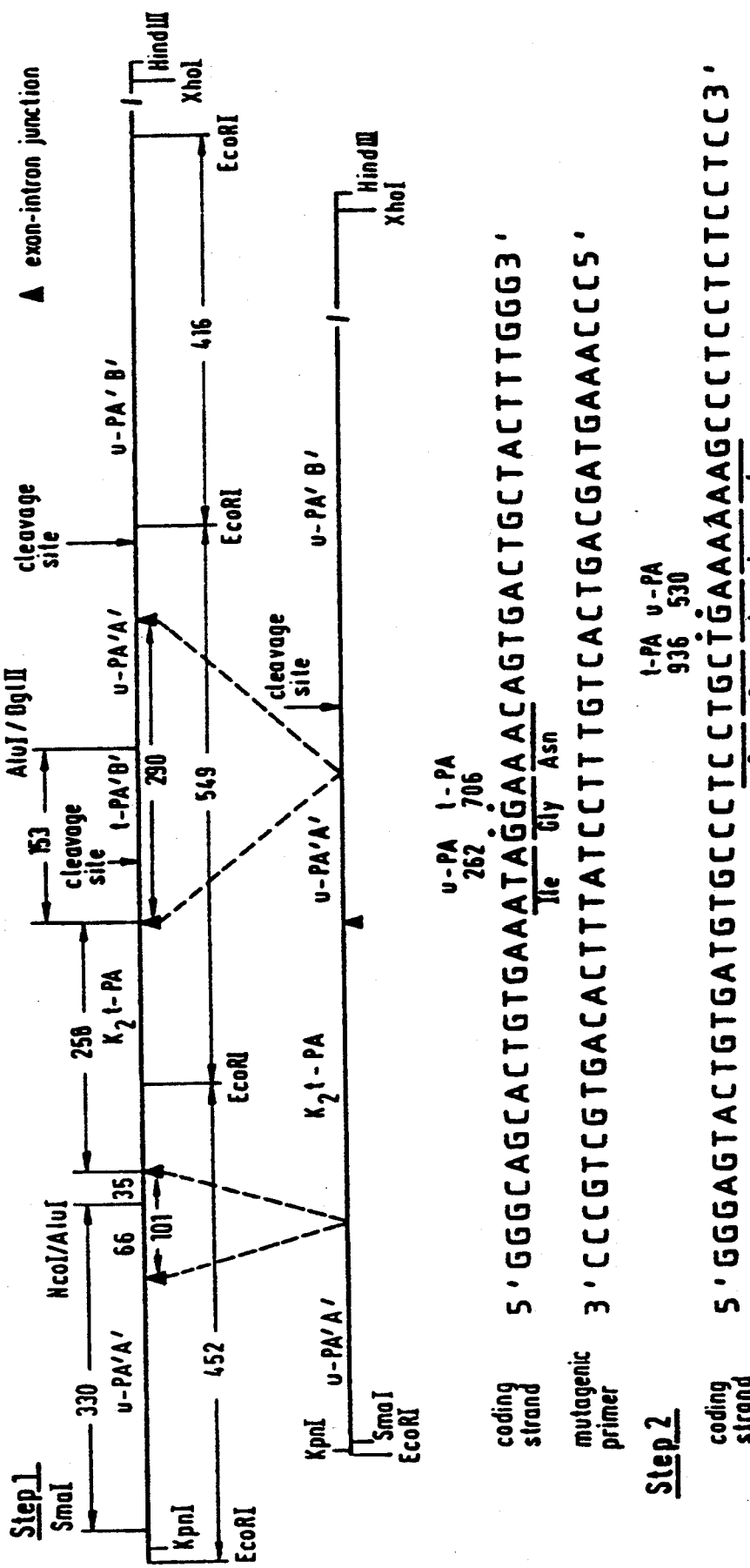

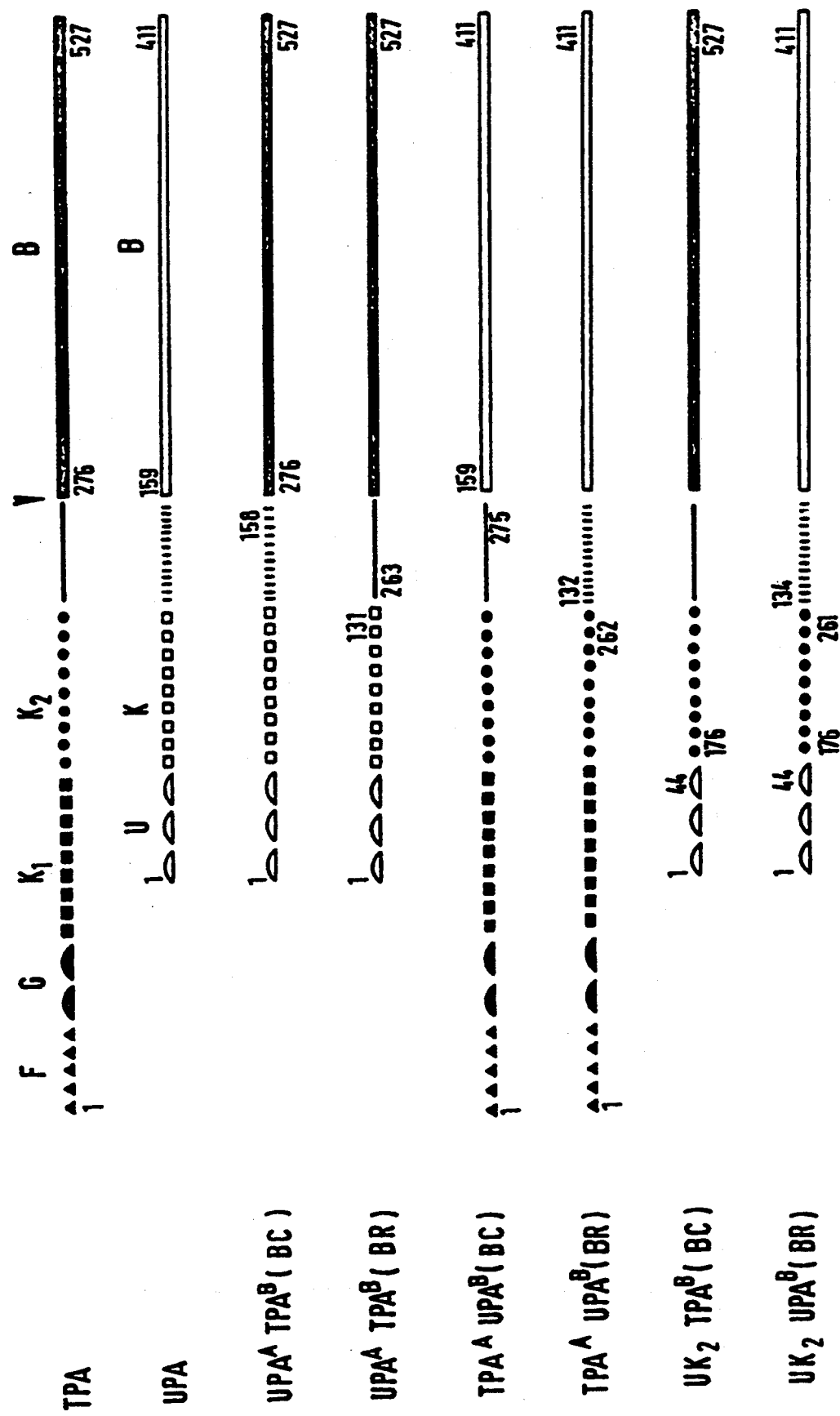

FIG.34:(CONTINUED)

FIG.34:(CONTINUED)
FUPA^B (Gln 302)(BC)
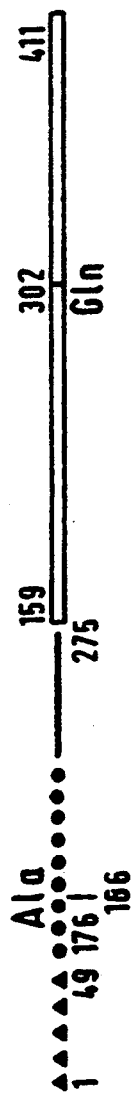
FK_2(Ala186) UPA^B(Gln 302)(BC)
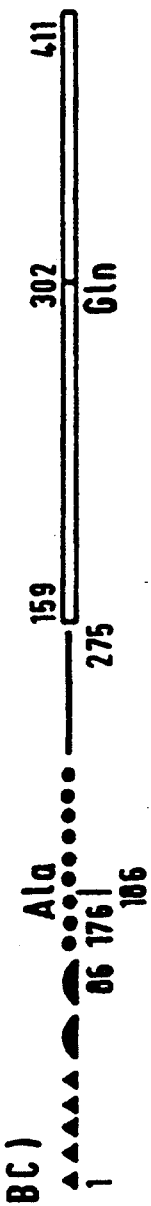
FGK_2(Ala186) UPA^B (Gln 302)(BC)
UK_2 (Ala 186) TPA^B (Ala 450)(BC)

PHARMACEUTICAL COMPOSITIONS COMPRISING MODIFIED AND UNMODIFIED PLASMINOGEN ACTIVATORS

This application is a continuation of application Ser. No. 07/573,434, filed Aug. 27, 1990, now abandoned.

The present invention relates to pharmaceutical compositions comprising a combination of two plasminogen activators differing in their amino acid sequence and to the use of said compositions for the prophylaxis or therapy of blood clotting disorders.

BACKGROUND OF THE INVENTION

Blood clots are one of the main causes of morbidity and of mortality of humans in the developed world. The network of blood clots consists of fibrin which is formed from its soluble precursor fibrinogen by the action of the enzyme thrombin. An array of enzymes and other substances ensure that clots normally form only when and where they are required to prevent loss of blood.

Mammalian plasma contains an enzymatic system, the fibrinolytic system, capable of dissolving blood clots. One component of the fibrinolytic system is a group of enzymes named plasminogen activators, which convert plasminogen (an inactive proenzyme form of plasmin) to the proteolytic enzyme plasmin. Plasmin then degrades the fibrin network of the clots to form soluble products. In cases where the thrombolytic capacity of the body is insufficient to remove intravascular thrombi, for example in patients suffering from thromboembolisms or post-surgical complications, it may be indispensable to use exogenously administered thrombolytic agents.

Two types of plasminogen activators (hereinafter referred to as "PAs") can be isolated from human body fluids or cells: urokinase or urokinase-type plasminogen activator (hereinafter referred to as "uPA"), a serine protease occurring e.g. in urine and kidney cells, and tissue-type plasminogen activator (hereinafter referred to as "tPA") which is produced by endothelial cells and found in a number of endocrine tissues.

Both tPA and uPA exist in two molecular forms. The single-chain (sc) or proenzyme form is specifically bound to components of the blood clot, such as fibrin, and is subsequently cleaved into the mature two-chain (tc) form by the action of plasmin. In the processed tcPA, the non-catalytic aminoterminal A-chain is connected via S-S bridges to the catalytic carboxyterminal B-chain.

Although ultimately cleaving the same peptide bond in the plasminogen molecule, tPA, scuPA and tcuPA exhibit unique properties, largely affecting the rate and the specificity of this reaction. Although being immunologically unrelated and having a different activation mechanism, both tPA and scuPA exhibit a high fibrin-affinity and therefore mainly activate fibrin-bound plasminogen. Free plasma plasminogen is only unsignificantly affected by tPA or scuPA. On the other hand, tcuPA, due to its lack of clot-specificity, activates both fibrin-bound and plasma plasminogen to the same extent, resulting in a systemic activation of the fibrinolytic system. The catalytic rate constant of tcuPA, however, is significantly higher than that of tPA.

Recently, a large number of hybrid PAs have been constructed by genetic engineering techniques. In these hybrids, sequences coding for parts of the tPA and parts of the uPA molecule were recombined into single chimeric molecules.

Simple hybrids are composed of the non-catalytic A-chain of one PA linked to the catalytic B-chain of the other PA (e.g. European Patent Applications Nos. 155 387 and 277 313). More complex hybrids have been constructed by recombining DNA sequences coding for discrete domains of the A-chain of tPA (which contains a "finger", a "growth factor" and two "kringle" domains) or uPA (which contains a "growth factor" and one "kringle" domain) with sequences encoding the B-chain of tPA or uPA (e.g. European Patent Applications Nos. 231 883 and 277 313 or PCT-Application No. 88/5822). "Polykringle" PAs combining in their A-chain multiple kringle structures of tPA and uPA have been described in European Patent Application No. 213 794.

The therapeutic value of tPA, uPA (especially scuPA with its high fibrin-specificity) and some of the hybrid PAs is of utmost importance in the treatment of blood clotting disorders such as thrombosis. However, often the thrombolytic action is not fast enough resulting in for example cardiac arrest in the case of myocardial infarction or incomplete leading to very rapid reocclusion of the opened vessel.

The simultaneous administration of tPA and scuPA or tPA and tcuPA as has been described in European Patent Application No. 223 192 results in a synergistic effect of the two components, i.e. a higher thrombolytic activity in vivo. Significant synergism between tPA and scuPA as well as between tPA and tcuPA has also been demonstrated in vivo by Collen and coworkers in a quantitative animal model system of thrombolysis (rabbit jugular vein with $^{125}$J-labelled fibrin clot; e.g. Collen et al. (1986) Circulation 74, 838–842; Collen et al. (1987) Thrombosis and Haemostasis 58, 943–946) and in human patients suffering from acute myocardial infarction (Collen and Van de Werf (1987) Amer. J. of Cardiology 60, 431–434; Collen (1988) Circulation 77, 731–735).

In vitro data were raised by other authors (Gurewich and Pannell (1986) Thrombosis Research 44, 217–228; Pannell et al. (1988) J. Clin. Invest. 81, 853–859) indicating that small amounts of tPA potentiate clot lysis by scuPA by attenuating the lag phase which is characteristic of scuPA and cause a much earlier transition to the rapid phase of lysis.

Because of their different mechanisms of plasminogen activation a potential synergistic or complementary mode of action between tPA and scuPA would be of significant clinical value since it would allow a reduction of the required total amount of these expensive drugs and, provided the toxic side-effects (such as allergic reactions, anaphylactic shock, intracranial hemorrhages or pyrogenic effects) would not be additive, the systemic fibrinolytic activation could be eliminated. Although a reduction of the total concentration of the PAs administered can be achieved while preserving an equivalent thrombolytic activity as described in the references cited, the applied doses, especially the one for uPA, are still too high to reliably exclude the possibility of negative side effects such as bleeding complications.

There is clearly a clinical need to overcome the problem of side effects arising in conventional thrombosis therapy. Superior fibrinolytic agents are required which are effective at relatively low doses thus minimizing possible side effects as well as saving expenses in therapy.

OBJECT OF THE INVENTION

It is the object of the present invention to provide superior fibrinolytic agents for the therapy and prophylaxis of blood clotting disorders such as thrombosis. This object is achieved by the provision of novel pharmaceutical compositions which comprise a combination of two plasminogen activators differing in their amino acid sequence. It has surprisingly been found that the combined administration of said two plasminogen activators leads even at low doses to a considerable enhancement of the fibrinolytic activity and that said two plasminogen activators act together in a manner so that one PA enhances the activity of the other (complementary mode of action).

DETAILED DESCRIPTION OF THE INVENTION

The present invention concerns a pharmaceutical combination composition comprising as component A a plasminogen activator comprising the tPA B-chain and as component B a single-chain plasminogen activator comprising the uPA B-chain, wherein component A cannot be tPA if component B is scuPA.

More specifically, the invention concerns a pharmaceutical combination composition comprising as component A a plasminogen activator of the formula $$NH_2-X_1-L_1-Y_1-COOH \qquad (I),$$

in which $X_1$ is a direct bond or an amino acid sequence comprising all or discrete A-chain domains of human tPA and/or all or discrete A-chain domains of human uPA, $L_1$ represents a direct bond or an amino acid sequence joining $X_1$ to $Y_1$ and $Y_1$ is the catalytic domain of human tPA, and as component B a single-chain plasminogen activator of the formula $$NH_2-X_2-L_2-Y_2-COOH \qquad (II),$$

in which $X_2$ is a direct bond or an amino acid sequence comprising all or discrete A-chain domains of human tPA or discrete A-chain domains of human tPA and of human uPA or all or discrete A-chain domains of human uPA, $L_2$ represents a direct body or an amino acid sequence joining $X_2$ to $Y_2$ and $Y_2$ is the catalytic domain of human uPA, together with a pharmaceutically acceptable carrier, wherein component A cannot be tPA if component B is scuPA.

A protein domain is a structural and/or functional entity within the overall structure of the entire protein. Both tPA and uPA consist in their mature form of a non-catalytic A-chain comprising 4 and 3 different domains, respectively, which are aligned in series, and a catalytic B-chain (catalytic domain) which contains the active center comprising the amino acid residues His, Asp and Ser at positions 322, 371 and 478 (tPA) and 204, 255 and 356 (uPA), respectively, and which is essential for enzymatic activity. The individual domains are on the genomic level separated by non-coding junction regions, so called introns, leading at their boundaries to exon-intron junctions.

Single-chain tPA can be represented by the following formula:

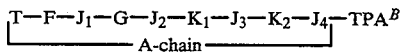

in which T represents the N-terminal part comprising amino acids 1 to 5, F is the finger domain comprising amino acids 6 to 43, G is the growth factor domain comprising amino acids 51 to 84, $K_1$ is the kringle 1 domain comprising amino acids 92 to 173, $K_2$ is the kringle 2 domain comprising amino acids 180 to 262, $TPA^B$ is the catalytic serine protease region (B-chain) comprising amino acids 276 to 527 and $J_1$ (amino acids 44 to 50), $J_2$ (amino acids 85 to 91), $J_3$ (amino acids 174 to 179) and $J_4$ (amino acids 263 to 275) are junction sequences joining the domain segments.

Single-chain uPA can be represented by the following formula:

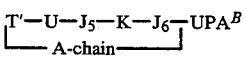

in which T' represents the N-terminal part comprising amino acids 1 to 12, U is the growth factor domain comprising amino acids 13 to 42, K is the kringle domain comprising amino acids 50 to 131, $UPA^B$ is the catalytic serine protease region (B-chain) comprising amino acids 159 to 411 and $J_5$ (amino acids 43 to 49), and $J_6$ (amino acids 132 to 158) are junction sequences joining the domain segments. The processing site is located between amino acids 275 and 276 (tPA) and 158 and 159 (uPA), respectively. N-terminal thereto, a cysteine residue is present which is involved in a sulphur-sulphur bridge to the catalytic (B-chain) region.

Suitable plasminogen activators for use as component A are those ones according to formula (I), in which $X_1$, $L_1$ and $Y_1$ have the following meanings:

$X_1$ is, for example, an amino acid sequence essentially consisting of discrete A-chain domains of human tPA or all A-chain domains of human tPA and the kringle domain of human uPA or the finger, the kringle 1 and the kringle 2 domains of human tPA and the growth factor and/or the kringle domain of human uPA or the kringle 2 domain of human tPA and the growth factor and/or the kringle domain of human uPA, $L_1$ is, for example, an amino acid sequence which, when linked to the N-terminal amino acid residue of $Y_1$, generates a plasmin processing site and which contains at least one Cys residue and $Y_1$ is the catalytic domain of human tPA consisting of amino acids 276 to 527 of human tPA or a fragment thereof retaining the catalytic activity.

The term essentially is intended to demonstrate that the amino acid sequences listed hereinbefore and hereinafter might additionally contain further sequences which are not essential for and which do not have any influence on the enzymatic activity. Non-essential sequences include sequences derived from other polypeptides which might have been fused during the synthesis of the respective plasminogen activator to the essential sequences. Non-essential sequences are, for example, amino acids 1 to 12 of mature acid phosphatase (PH05).

In a preferred embodiment of the present invention, $X_1$ is a direct bond or an amino acid sequence essentially consisting of all A-chain domains of human tPA or the kringle 2 domain of human tPA and the growth factor domain of human uPA; Especially $X_1$ is a direct bond or an amino acid sequence consisting of amino acids 1 to 262 of human tPA or of amino acids 1 to 44 of human uPA linked in series to amino acids 176 to 262 of human tPA.

Also preferred are plasminogen activators according to formula (I), in which $L_1$ represents an amino acid sequence which comprises an amino acid sequence consisting of 11 to 40 amino acids derived from tPA and/or uPA and/or any other polypeptide like e.g. mature acid phosphatase (PH05) and which contains at least one Cys residue. Especially, $L_1$ represents an amino acid sequence in which the Cys residue is at a remove of 11 or 12 amino acids away from the N-terminal amino acid residue of $Y_1$.

In the most preferred aspect, $L_1$ represents an amino acid sequence selected from the group consisting of amino acids 263 to 275 of human tPA, amino acids 147 to 158 of human uPA and amino acids 1 to 12 of mature acid phosphatase (PH05) linked in series to amino acids 256 to 275 of human tPA.

Preferred plasminogen activators are those of the formula (I), in which $X_1$ is a direct bond or an amino acid sequence selected from the group consisting of amino acids 1 to 262 of human tPA and amino acids 1 to 44 of human uPA linked in series to amino acids 176 to 262 of human tPA, $L_1$ represents an amino acid sequence consisting of amino acids 263 to 275 of human tPA and $Y_1$ is the catalytic domain of human tPA consisting of amino acids 276 to 527 of human tPA.

The most preferred plasminogen activators for use as component A are tPA or those of the formula (I), in which $X_1$ is a direct bond, $L_1$ represents an amino acid sequence consisting of amino acids 263 to 275 of human tPA and $Y_1$ is the catalytic domain of human tPA consisting of amino acids 276 to 527 of human tPA (designated as tPA B-chain, extended), or in which $X_1$ is an amino acid sequence consisting of amino acids 1 to 44 of human uPA linked in series to amino.acids 176 to 262 of human tPA and $L_1$ and $Y_1$ are as defined above (designated as uK$_2$tPA), or in which $X_1$ is a direct bond, $L_1$ represents an amino acid sequence consisting of amino acids 1 to 12 of mature acid phosphatase (PH05) linked in series to amino acids 256 to 275 of human tPA and $Y_1$ is as defined above (designated as tPA B-chain, fused).

Suitable plasminogen activators for use as component B are those ones according to formula (II), in which $X_2$, $L_2$ and $Y_2$ have the following meanings:

$X_2$ is, for example an amino acid sequence essentially consisting of the finger and/or the kringle 2 domain of human tPA or the finger, the growth factor and the kringle 2 domains of human tPA or the growth factor, the kringle 1 and the kringle 2 domains of human tPA or the growth factor and/or the kringle domain of human uPA and the kringle 2 domain of human tPA, $L_2$ is, for example, an amino acid sequence which, when linked to the N-terminal amino acid residue of $Y_2$, generates a plasmin processing site and which contains one Cys residue and $Y_2$ is the catalytic domain of human uPA consisting of amino acids 159 to 411 of human uPA or a fragment thereof retaining the catalytic activity.

In a preferred embodiment of the present invention, $X_2$ is an amino acid sequence essentially consisting of the finger and the kringle 2 domain of human tPA or the kringle 2 domain of human tPA. Especially $X_2$ is a direct bond or an amino acid sequence consisting of amino acids 1 to 49 and 176 to 262 or amino acids 1 to 3 and 176 to 262 of human tPA.

Also preferred are plasminogen activators according to formula (II), in which $L_2$ represents an amino acid sequence consisting of 11 to 28 amino acids and including one Cys residue, especially, $L_2$ represents an amino acid sequence in which the a Cys residue is at a remove of 11 or 12 amino acids away from the N-terminal amino acid residue of $Y_2$.

In the most preferred aspect, $L_2$ represents an amino acid sequence selected from the group consisting of amino acids 263 to 275 of human tPA, amino acids 147 to 158 of human uPA and amino acids 144 to 158 of human uPA.

Preferred single-chain plasminogen activators are those of the formula (II), in which $X_2$ is a direct bond or an amino acid sequence consisting of amino acids 1 to 49 and 176 to 262 or amino acids 1 to 3 and 176 to 262 of human tPA, $L_2$ represents an amino acid sequence selected from the group consisting of amino acids 263 to 275 of human tPA, amino acids 147 to 158 of human uPA and amino acids 144 to 158 of human uPA and $Y_2$ is the catalytic domain of human uPA consisting of amino acids 159 to 411 of human uPA.

The most preferred single-chain plasminogen activators for use as component B are those of the formula (II), in which $X_2$ is an amino acid sequence consisting of amino acids 1 to 49 and 176 to 262 of human tPA, $L_2$ represents an amino acid sequence consisting of amino acids 263 to 275 of human tPA and $Y_2$ is the catalytic domain of human uPA consisting of amino acids 159 to 411 of human uPA (designated as FK$_2$tuPA), or in which $X_2$ is an amino acid sequence consisting of amino acids 1 to 3 and 176 to 262 of human tPA, and $L_2$ and $Y_2$ are as defined above (designated as K$_2$tuPA).

A preferred pharmaceutical composition comprises as component A a plasminogen activator of the formula (I), in which $X_1$ is a direct bond, $L_1$ represents an amino acid sequence consisting of amino acids 263 to 275 of human tPA and $Y_1$ is the catalytic domain of human tPA consisting of amino acids 276 to 527 of human tPA (designated as tPA B-chain, extended) and as component B scuPA or a plasminogen activator of the formula (II), in which $X_2$ is an amino acid sequence consisting of amino acids 1 to 49 and 176 to 262 of human tPA, $L_2$ represents an amino acid sequence consisting of amino acids 263 to 275 of human tPA and $Y_2$ is the catalytic domain of human uPA consisting of amino acids 159 to 411 of human uPA (designated as FK$_2$tuPA) or as component B a plasminogen activator of the formula (II), in which $X_2$ is an amino acid sequence consisting of amino acids 1 to 3 and 176 to 262 of human tPA, $L_2$ represents an amino acid sequence consisting of amino acids 263 to 275 of human tPA and $Y_2$ is the catalytic domain of human uPA consisting of amino acids 158 to 411 of human uPA (designated as K$_2$tuPA).

Another preferred pharmaceutical composition comprises as component A tPA and as component B a plasminogen activator of the formula (II), in which $X_2$ is an amino acid sequence consisting of amino acids 1 to 49 and 176 to 262 of human tPA, $L_2$ represents an amino acid sequence consisting of amino acids 263 to 275 of human tPA and $Y_2$ is the catalytic domain of human uPA consisting of amino acids 159 to 411 of human uPA (designated as FK$_2$tuPA) or as component B a plasminogen activator of the formula (II), in which $X_2$ is an amino acid sequence consisting of amino acids 1 to 3 and 176 to 262 of human tPA, $L_2$ represents an amino acid sequence consisting of amino acids 263 to 275 of human tPA and $Y_2$ is the catalytic domain of human uPA consisting of amino acids 159 to 411 of human uPA (designated as $K_2$tuPA).

Equally preferred is a pharmaceutical composition comprising as component A a plasminogen activator of the formula (I), in which $X_1$ is an amino acid sequence consisting of amino acids 1 to 44 of human uPA linked in series to amino acids 176 to 262 of human tPA, $L_1$ represents an amino acid sequence consisting of amino acids 263 to 275 of human tPA and $Y_1$ is the catalytic domain of human tPA consisting of amino acids 276 to 527 of human tPA (designated as u$K_2$tPA) and as component B scuPA or a plasminogen activator of the formula (II), in which $X_2$ is an amino acid sequence consisting of amino acids 1 to 49 and 176 to 262 of human tPA, $L_2$ represents an amino acid sequence consisting of amino acids 263 to 275 of human tPA and $Y_2$ is the catalytic domain of human uPA consisting of amino acids 159 to 411 of human uPA (designated as F$K_2$tuPA) or as component B a plasminogen activator of the formula (II), in which $X_2$ is an amino acid sequence consisting of amino acids 1 to 3 and 176 to 262 of human tPA, $L_2$ represents an amino acid sequence consisting of amino acids 263 to 275 of human tPA and $Y_2$ is the catalytic domain of human uPA consisting of amino acids 159 to 411 of human uPA (designated as $K_2$tuPA).

Further pharmaceutical compositions comprise as component A a plasminogen activator of the formula (I), in which $X_1$ is a direct bond, $L_1$ is an amino acid sequence consisting of amino acids 1 to 12 of mature acid phosphatase (PH05) linked in series to amino acids 256 to 275 of human tPA and $Y_1$ is the catalytic domain of human tPA consisting of amino acids 276 to 527 of human tPA (designated as tPA B-chain, fused) and as component B scuPA or a plasminogen activator of the formula (II), in which $X_2$ is an amino acid sequence consisting of amino acids 1 to 49 and 176 to 262 of human tPA, $L_2$ represents an amino acid sequence consisting of amino acids 263 to 275 of human tPA and $Y_2$ is the catalytic domain of human uPA consisting of amino acids 159 to 411 of human uPA (designated as F$K_2$tuPA) or as component B a plasminogen activator of the formula (II), in which $X_2$ is an amino acid sequence consisting of amino acids 1 to 3 and 176 to 262 of human tPA, $L_2$ represents an amino acid sequence consisting of amino acids 263 to 275 of human tPA and $Y_2$ is the catalytic domain of human uPA consisting of amino acids 159 to 411 of human uPA (designated as $K_2$tuPA).

The plasminogen activators contained in the pharmaceutical combination composition are known compounds or can be prepared by methods well known in the art. Especially preferred are those PAs which have been prepared by recombinant DNA techniques such as described in EP 277 313, EP 231 885, EP 275 856, WO 88/8451, EP 275 606, EP 273 774, EP 213 794, WO 88/5822, EP 143 081, EP 225 286, EP 288 435 and in Lijnen et al. (J. Biol. Chem 263, 5594–5598 (1988).

The novel combination composition according to the invention can be used in humans for the prevention or treatment of thrombosis or diseases caused by thrombosis, arteriosclerosis, myocardial and cerebral infarction, venous thrombosis, thromboembolism, post-surgical thrombosis, thrombophlebitis, etc.

The pharmaceutical compositions according to the invention can be used for the treatment of the above-mentioned indications when they are administered parenterally, such as intravenously.

The combination composition may either contain components A and B in a manner which necessitates administering them at the same time and by the same route or may comprise components A and B separately (kit of parts) allowing for administration at different times and/or by different routes.

There are suitable infusion or injection solutions, preferably aqueous isotonic solutions or suspensions, it being possible to prepare these before use, for example from lyophilised preparations that contain the active ingredient(s) alone or together with a pharmaceutically acceptable carrier, such as mannitol, lactose, dextrose, human serum albumin and the like. The pharmaceutical compositions are sterilized and, if desired, mixed with adjuncts, for example preservatives, stabilisers, emulsifiers, solubilisers, buffers and/or salts (such as 0.9% sodium chloride) for adjusting the isotonicity. Sterilization can be achieved by sterile filtration through filters of small pore size (0.45 μm diameter or smaller) after which the composition can be lyophilised, if desired. Antibiotics may also be added in order to assist in preserving sterility. For example, standard formulation techniques developed for the administration of PAs (i.e. European Patent Applications No. 93 619, 41 766, 122 940 and others) or novel compositions confering sufficient solubility to the PA in low pH buffered media (examples are in European Patent Application No. 211 592, German Offenlegungsschrift No. 3 617 752, 3 617 753, 3 642 960) may be used. For stability reasons it is recommended to reconstitute lyophylized samples in 5% dextrose or 5% mannitol or 0.9% sodium chloride and the like.

Depending upon the type of the disease and the age and the condition of the patient, the daily dose to be administered once for the treatment of a patient weighing approximately 70 kg is in the range from 5 to 100 mg, especially 10 to 40 mg, component A and 5 to 100 mg, especially 10 to 40 mg, component B. Accordingly, the weight ratio between component A and component B in the composition may vary, in general between 1:1 and 1:20. A weight ratio between 1:2 and 1:10 is preferably used.

The pharmaceutical compositions according to the present invention are dispensed in unit dosage forms, for example in ampoules comprising therapeutically effective amounts of both components A and B or, preferably, in double ampoules comprising therapeutically effective amounts of components A and B separately, together with a pharmaceutically acceptable carrier.

The present pharmaceutical compositions are produced in a manner known per se, applying a conventional lyophilising or dissolving procedures, for example by mixing components A and B and optionally the pharmaceutically acceptable carrier, and, for the preparation of a lyophilisate, freeze-drying an aqueous solution obtained. The compositions contain from approximately 0.1% to 20%, especially from approximately 1% to 10%, and in the case of lyophilisates up to 100% of the active ingredients.

The invention relates also to the use of the combination compositions according to the invention for the prophylactic and therapeutic treatment of the human body, especially for the above-mentioned clinical syndromes, in particular for the prophylaxis and therapy of thrombosis or diseases caused by thrombosis in the human body.

A further object of the present invention is founded on the surprising observation that the combined administration of components A and B leads to an enhancement of the fibrinolytic activity. Accordingly, the invention concerns a method for preventing or treating thrombosis or a disease caused by thrombosis in a human comprising administering to said human a pharmaceutical combination composition comprising a fibrinolytically effective amount of components A and B.

BRIEF DESCRIPTION OF THE DRAWINGS

FIGS. 1 to 7 are diagrams showing the clot lysis activity of different combinations of plasminogen activators.

FIG. 1 depicts the complementary mode of action of tPA and $K_2$tuPA.

FIG. 2 depicts the complementary mode of action of tPA and $FK_2$tuPA.

FIG. 3 depicts the complementary mode of action of $uK_2$tPA and scuPA.

FIG. 4 depicts the complementary mode of action of $uK_2$tPA and $K_2$tuPA.

FIG. 5 depicts the complementary mode of action of tPA B-chain (fused) and scuPA.

FIG. 6 depicts the additive mode of action of tPA and $uK_2$tPA.

FIG. 7 depicts the additive mode of action of $K_2$tuPA and $FK_2$tuPA.

FIG. 8 and FIG. 10 illustrate the nucleotide sequences and deduced amino acid sequences of human t-PA cDNA and human u-PA or cDNA, respectively. The first amino acids of the mature proteins are underlined.

FIG. 9 and FIG. 11 are restriction endonuclease maps of human t-PA cDNA and human u-PA cDNA, respectively.

FIG. 12 schematically illustrates the technique used to construct plasmid pEco0.47ΔScaI.

FIG. 13 schematically illustrates the construction of plasmid ph•tPAΔScaI containing a mutated t-PA cDNA.

FIG. 14 schematically illustrates the construction of plasmid pUNC•tc containing a cDNA insert comprising the A-chain domains of u-PA and the B-chain of t-PA.

FIG. 15 schematically depicts the construction of plasmid ptNC-UC containing a cDNA insert comprising the A-chain domains of t-PA and the B-chain of u-PA.

FIG. 16 schematically depicts the construction of plasmid pDO2.

FIG. 17 schematically illustrates the construction of plasmid pDO10 containing the t-PA cDNA combined with a beta globin fragment.

FIG. 18 schematically illustrates the construction of plasmid pCGA26 containing the t-PAc DNA under control of the MCMV IE promoter and a beta globin fragment.

FIG. 19 schematically illustrates the construction of t-PA expression plasmid pCGA28 and of universal expression plasmid pCGA44, both plasmids including the neomycin resistance gene.

FIG. 20 schematically illustrates the construction of t-PA expression plasmid pCGA42 and of universal expression plasmid pCGA42d, both plasmids including the hygromycin resistance gene.

FIG. 21 schematically illustrates the construction of t-PA expression plasmid pCGA48 including the neomycin resistance gene and the DHFR gene.

FIG. 22 schematically illustrates the construction of expression plasmid pBR1a containing the mutated t-PA cDNA insert of plasmid ph•PAΔScaI.

FIG. 23 schematically shows the construction of expression plasmid pBR2a containing a hybrid PA cDNA insert comprising the A-chain domains of u-PA and the B-chain of t-PA.

FIG. 24 schematically depicts the construction of u-PA expression plasmid pBR3a.

FIG. 25 schematically illustrates the construction of expression plasmid pBR4a containing a hybrid PA cDNA insert comprising the A-chain domains of t-PA and the B-chain of u-PA.

FIG. 26 schematically shows the construction of yeast expression vector pJDB207/PHO5-1-TPA containing the PHO5 promoter, the invertase signal sequence and t-PA cDNA.

FIG. 27 schematically illustrates the construction of plasmid pCS16.

FIG. 28 schematically illustrates the construction of plasmid pCS16/UPA comprising the u-PA cDNA.

FIG. 29 schematically shows the construction of plasmid pJDB207/PHO5-1-UPA.

FIGS. 30–33 schematically illustrate the techniques used to convert primary hybrid PA constructs including A-chain domains and the catalytic B-chain region of u-PA or t-PA into the final constructs in which the junction of the domains is at the activation site and/or at the natural exon-intron junction sites;

FIG. 30 shows the construction of a gene coding for a hybrid PA comprising the A-chain domains of t-PA and the B-chain of u-PA.

FIG. 31 shows the construction of a gene coding for a hybrid PA comprising the A-chain domains of u-PA and the B-chain of t-PA.

FIG. 32 shows the construction of a gene coding for a hybrid PA comprising the u-PA growth factor domain, the kringle 2 domain of t-PA and B-chain of t-PA.

FIG. 33 shows the construction of a gene coding for a hybrid PA comprising the u-PA growth factor domain, the kringle 2 domain of t-PA and the B-chain of u-PA.

FIG. 34 is a compilation of hybrid PAs and mutant hybrid PAs as exemplified in the Experimental Part.

Symbols used in the accompanying figures have the following meanings:

AMP, $Amp^R$ ampicillin resistance gene (beta-lactamase)
TET, $Tet^R$ tetracyclin resistance gene
NEO Tn5 neomycin phosphotransferase
TN5PR bacterial promoter of tranposon TN5
HPH hygromycin phosphotransferase
pBRori origin of replication of plasmid pBR322
POIS 'poison-sequence', pBR322 sequence which is inhibitory to SV40 replication
SV40ori origin of replication of SV40, coincides with early and late promoters.
SV40enh,SV40E 72 bp enhancer, part of SV40 early promoter
HCMVE enhancer of human cytomegalovirus (HCMV) major immediate early gene
MCMVP promoter/mRNA start site of mouse cytomegalovirus (MCMV) major immediate early gene
RSV Rous sarcoma virus LTR (promoter)
CAP position of 5' m7Gp 'cap' of eukaryotic mRNA
polyA polyadenylation site of mRNA
SPLD splice donor site, 5' end of intron
SPLA splice acceptor site, 3' end of intron BAP bacterial alkaline phosphatase
CIP calf intestinal phosphatase
(BamHl/Bgl2) Sau3a site resulting from coligating a BamHI and a BglII site
ScaI(del) mutated ScaI site
x<y restriction enzyme site x located clockwise from y
p promoter Yeast, Alfred Benzon Symposium, Munksgaard, von Wettstein et al. (eds.), Vol. 16, 383–390) cut with BamHI and HindIII.

The resulting yeast expression plasmid pJDB207/PH05-TPA B has the following in frame fusion of amino acid 1–12 of mature acid phosphatase to Cys 256 of tPA:

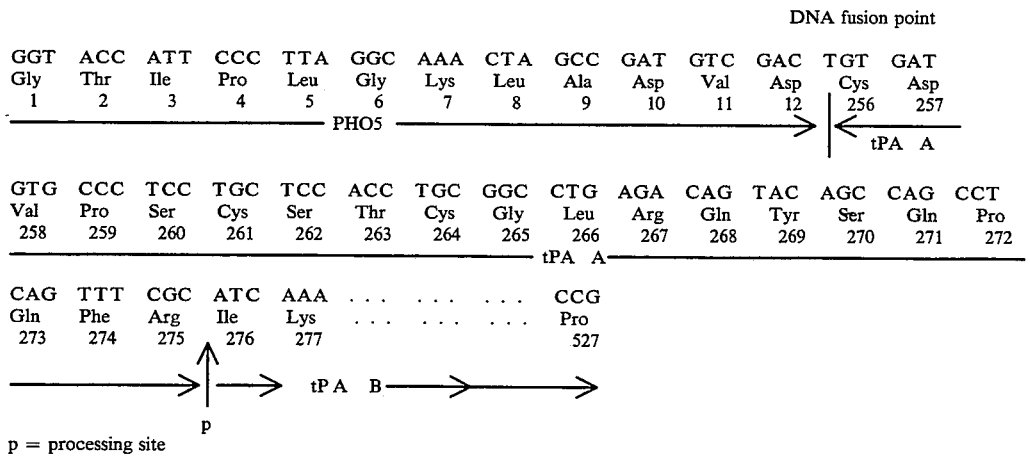

inv.SS invertase signal sequence
t transcription terminator
L linker DNA
DHFR dihydrofolate reductase
mtPA Bowes melanoma t-PA The following examples illustrate the invention without implying any limitation.

EXAMPLE 1

Construction of a Yeast Expression Plasmid Encoding the tPA B-chain (Fused)

The nucleotide sequence coding for the tPA B-chain (Ile 276-Pro 527) is isolated from plasmid p31/PH05-TPA18 (European Patent Application No. 143 081) which contains the complete coding sequence of mature tPA. p31/PH05-TPA18 is a pBR322-derived plasmid with a BamHI/HindIII insert comprising the PH05 promoter, the PH05 signal sequence, the coding sequence of tPA and the PH05 transcription termination signals in an anti-clockwise orientation. p31/PH05-TPA18 is digested with ScaI and HindIII and the resulting 1 kb fragment encodes amino acids Cys 256 to Pro 527 of tPA.

Plasmid p29 (Haguenauer-Tsapis et al. (1984), Mol. Cell. Biol. 4, 2668–2675) contains the yeast genes for the repressible and constitutive acid phosphatases (PH05 and PH03) in a tandem array on a 3,9 kb BamHI-HpaI fragment (Bajwa et al. (1984), Nucleic Acids Research 12, 7721–7739). The DNA fragment is isolated from plasmid p30 (European Patent Application No. 143 081, deposited as DSM 4297) and cloned in pBR322 between BamHI and PvuII in clockwise orientation, which results in plasmid p29. An AccI restriction digest, a fill-in reaction with Klenow DNA polymerase and a BamHI restriction digest leads to a 626 bp fragment that contains the PH05 promoter, signal sequence and a 34 nucleotide extension into the coding sequence of mature PH05.

The 1 kb ScaI/HindIII fragment of p31/PH05-TPA18 and the 626 pb fragment of p29 are ligated via their blunt ends and cloned into the yeast vector pJDB207 (Beggs (1981), in: Molecular Genetics in The corresponding protein is designated as tPA B-chain (fused).

EXAMPLE 2

Transformation of Saccharomyces Cerevisiae Strain HT246 with pJDB207/PH05-TPA B

Saccharomyces cerevisiae strain HT246 (a, leu2-3, leu2-112, prb; DSM 4084) is transformed with plasmid pJDB207/PH05-TPA B using the transformation protocol described in Hinnen et al. (Proc. Natl. Acad. Sci. USA 75, 1929 (1978)). Transformed yeast cells are selected on yeast minimal media plates deficient in leucine. Single transformed yeast colonies are isolated and referred to as Saccharomyces cerevisiae HT246/pJDB207/PH05-TPA B.

EXAMPLE 3

Fermentation of Saccharomyces cerevisiae HT246/pJDB207/PH05-TPA B

Saccharomyces cerevisiae HT246/pJDB207/PH05-TPA B contains a plasmid with the full length PH05 promoter and requires derepression of the promoter for expression of tPA B-chain. Cells of the S. cerevisiae HT246 transformants are grown in 10 ml of yeast minimal medium (Difco Yeast Nitrogen Base without amino acids to which 2% glucose and 20 mg/l L-histidine are added) in a 50 ml Erlenmeyer flask with shaking at 30° C. for 24 h until a density of $5-7\times 10^7$ cells/ml is reached. The cells of the preculture are then washed in 0.9% NaCl and 20% of the preculture cells are used to inoculate 50 ml of a low $P_i$ minimal medium prepared according to the recipe of the Difco Yeast Nitrogen Base medium (without amino acids), but containing 0.03 g/l $KH_2PO_4$, 10 g/l L-aspargine instead of $(NH_4)_2SO_4$, 20 g/l glucose and 1 g/l L-histidine. The cultures are agitated at 30° C. for up to 48 h at 180 revs/min. Final densities of $5\times 10^7$ cells/ml ($=OD_{600}=4-5$) are obtained.

EXAMPLE 4

Recovery of tPA B-chain (Fused) from Yeast Culture Supernatants

Yeast recombinant tPA B-chain (fused) is prepared from a 30 l fermentation of strain HT246/pJDB207/PH05-TPA B in a low phosphate medium.

To 30 l supernatant after 60 hours of fermentation DE-3 Sepharose beads (EP 112 122) are added and the suspension is stirred for 1 hour at 4° C. The beads are then transferred to a column and washed with 1M NaCl, 10 mM sodium phosphate, pH 7.0, 0.1% Tween 80. Elution of tPA B-chain (fused) from the column is achieved with 1.6M NH4SCN in a buffer consisting of 10 mM sodium phosphate pH 7.0 and 0.05% Tween 80.

Purity of yeast recombinant tPA B-chain (fused) after 2 consecutive chromatography cycles on DE-3 is greater than 90% as assessed by SDS gel electrophoresis. The molecule migrates with an apparent molecular weight >120 kD which is reduced upon treatment with endoglycosidase H (Trimble et al. (1984) Anal. Biochem. 141, 515–522) to about 33 kD. This indicates that secreted yeast recombinant tPA B-chain (fused) is highly glycosylated, glycosylation contributing 75% of the total molecular weight.

Activity of yeast recombinant tPA B-chain (fused) is measured with a fluorimetric assay (Zimmermann et al. (1978) Proc. Natl. Acad. Sci USA 75, 750). The specific activity of tPA B-chain (fused) is 150.000 FU/mg protein (for comparison: activity of yeast recombinant tPA as described in EP 100 561 is 125.000 FU/mg).

EXAMPLE 5

Recovery of scuPA from Saccharomyces Cerevisiae

Yeast recombinant scuPA is expressed as described in Europen Patent Application No. 288, 435. S. cerevisiae strain HT246/pJDB207/GAPDL-I-UPA is grown in a complex medium consisting of (g/l): peptone 5, yeast extract 10, glucose 20, sucrose 40, $(NH_4)_2SO_4$ 3, $KH_2PO_4$ 2, $MgSO_4$ 0.5, NaCl 0.1, $CaCl_2$ 0.1, biotin 10 µg/l. Approximately $1 \times 10^9$ cells/ml ($=OD_{600}$ 40–45) are obtained after 48 h of incubation at 30° C. and 200 revs/min.

The culture is centrifuged and the cells are resuspended in lysis buffer consisting of 66 mM potassium phosphate pH 7.4, 4 mM Zwittergent (Calbiochem) and broken in a Dyno-Mill (Braun-Melsungen). The supernatant of the broken cell suspension is adjusted to 500 ml with 25 mM potassium phosphate pH 7.4, 0.5% Tween 80. 50 g of preswollen anione exchanger DE52 (Whatman, Springfield, England) are added and the suspension is shaken for 30 min at 4° C. The beads are separated from the solution using a Buchner funnel and the solution adjusted to pH 4 with 1N HCl. Conductivity should ideally be 10–11 mS (milliSiemens). 50 g (wet weight) of the cation exchange S-Sepharose Fast Flow (Pharmacia, Uppsala, Sweden) are added and the suspension is shaken for 1 h at 4° C. After washing, the beads are transferred to a column of diameter 10 mm and scuPA is eluted with 100 mM Tris-HCl pH 8.5, 0.05% Tween 80. The fractions containing scuPA are immediately applied to an anti-urokinase IgG-sepharose 4 B column [purified polyclonal rabbit antibody (IgG fraction) raised against human urinary urokinase], washed with 2 volumes of the same buffer and then eluted with 0.5M NaCl, 0.2M glycine-HCl, pH 2.5. ScuPA produced in yeast is eluted in a pure form as judged by SDS polyacyrlamide gel electrophoresis. Yeast scuPA migrates as a single band of about 54–55 KD molecular weight under reducing conditions.

EXAMPLE 6

Recovery of Hybrid Plasminogen Activators from CHO Cell Culture Supernatants

Hybrid plasminogen activators are expressed in CHO cells as disclosed in European Patent Application No. 277 313. The hybrid plasminogen activators designated as $UK_2TPA^B$(BC), $K_2UPA^B$(BC) and $FK_2UPA^B$(BC) in EP 277 313 are identical to the hybrids $uK_2tPA$, $K_2tuPA$ and $FK_2tuPA$, respectively.

EXAMPLE 6.1

Introduction of a ScaI Site at the Junction Between the Kringle Structures and the Enzyme Domain in Human t-PA cDNA One approach used to construct chimeric or hybrid molecules containing domains of both t-PA and u-PA consists in preparing desired restriction fragments derived from the respective clones, reassembling them in solution, then cloning the resulting constructs. After cloning the structure of the chimeric molecules is verified by restriction mapping and DNA sequence analysis.

To obtain the hybrid molecules both t-PA and u-PA cDNAs are cleaved at the junctions between the respective kringle structures and enzyme domains. This is accomplished with u-PA by performing a partial digest with the restriction endonuclease MstI, which separates the non-catalytic domain from the enzyme domain and associated sequences at its 3'end. No comparably useful potential cleavage site is present in t-PA, and one is accordingly introduced as described below.

A) Construction of Plasmid pEco0.47ΔScaI (see FIG. 12)

In this construct, the unique ScaI site (AGTACT) at nucleotide position 940–945 of the t-PA cDNA is destroyed (AGTACT→AGTATT) and another ScaI site introduced at nucleotide positions 963–968 (TCCACC-→AGTACT) at the 3'end of kringle 2 (cf. FIGS. 8 and 9). The coding of none of the amino acids is affected by these changes.

All restriction digests are carried out according to the manufacturer's (New England Biolabs. Bethesda Research Labs) instructions and the resulting digests are analyzed by electrophoresis on 3.5% polyacrylamide gel. The gel is stained with ethidium bromide (1.0 µg/ml) and visualized with ultraviolet light. The appropriate band is excised and electroeluted in 0.5×TBE (1×TBE=90 mM Tris-borate, pH 8.3, 2.5 mM EDTA). The electroeluted material is applied to Elutipd column (Schleicher and Schuell), the bound DNA eluted in high salt and precipitated by the addition of ethanol. The pellet is washed with ethanol, dried and dissolved in water.

Plasmid pW349F (European Patent Application No. 143,081) containing human t-PA cDNA (synthesized from mRNA isolated from HeLaS3 cells and cloned into the PstI site of plasmid pBR322) is digested with EcoRI and the 470 base pair (bp) fragment (cf. FIG. 9) is isolated. The 150 bp EcoRI, ScaI and the 290 bp EcoRI, HaeIII fragments are obtained by digesting the 470 bp EcoRI fragment with ScaI and HaeIII, respectively. The two strands of the 470 bp EcoRI fragment are separated by denaturing the DNA in DMSO buffer (30% DMSO, 1 mM EDTA, 0.5% xylene, cyanole, 0.05% bromphenol blue) and electrophoresing on a 5% polyacrylamide gel in 0.5×TBE at 8 volts per centimeter [Maniatis et al., Molecular Cloning, A Laboratory Manual, Cold Spring Harbor Laboratory; 1982]. The separated strands are recovered by electroelution followed by ethanol precipitation. A 31-mer deoxyoligonucleotide (incorporating the 5 desired nucleotide changes, cf. FIG. 5) is synthesized using the phosphotriester method. Fifty pmoles of the 31-mer are $^{32}$P-labelled at the 5'end in a 20 µl reaction containing 1×kinase buffer (10×kinase buffer=0.5M Tris.HCl, pH 7.5, 0.1M MgCl$_2$, 50 mM DTT, 1 mM spermidine, 1 mM EDTA), 30 µCi[α$^{32}$]ATP (Amersham, ~3000 Ci/mmol) and 10 units T$_4$ polynucleotide kinase (Bethesda Research Labs.). The reaction is incubated at 37° C. for 30 minutes followed by the addition of 1 µl of 10 mM ATP, 10 units T$_4$ kinase and a further 30 minutes incubation at 37° C. The reaction is terminated at heating at 68° C. for 10 min. The labelled 31-mer, whose sequence is that of the non transcribed strand, is used as the probe in a dot blot analysis [performed according to Zoller and Smith, Nucl. Acids. Res., 10, 6487–6500 (1982); except that prehybridization and hybridization are done at 50° C. and washing at 60° C.] to determine which of the two strands hybridizes to it, i.e. represents the transcribed strand. The four DNAs are mixed together in a 20 µl EcoRl, Scal and 290 bp EcoRl, HaeIII fragments, 25 pmoles of the phosphorylated 31-mer and 1×annealing buffer (5×annealing buffer=0.5M NaCl, 32.5 mM Tris.HCl pH 7.5, 40 mM MgCl$_2$ and 5 mM β-mercaptoethanol). The mixture is incubated at 100° C. for 3 min, 30° C. for 30 min, 4° C. for 30 min and then on ice for 10 min following which 400 units of T$_4$ DNA ligase (New England Biolabs) are added and the reaction incubated at 12.5° C. overnight. The 470 bp anneealed fragment is recovered from a 3.5% polyacrylamide gel as described above and ligated to EcoRl digested and dephosphorylated pBR322 DNA (New England Biolabs) in 50 mM Tris.HCl pH 7.5, 10 mM MgCl$_2$, 10 mM DTT, 1 mM ATP, 1 mM spermidine, 0.1 mg/ml bovine serum albumin by overnight incubation at 12° C. The ligation mix is used to transform competent E. coli strain HB101 (Maniatis et al., supra). Ampicillin-resistant colonies are selected on L-agar containing 50 µg/ml ampicillin and colonies containing the 470 bp fragment are identified by colony hybridization using the 31-mer as the probe [D. Woods, Focus 1, 1–3 (1984)]. Plasmid DNA is isolated from several positively hybridizing colonies on a small scale [Holmes et al., Analyt. Biochem. 114, 193–197 (1981)] and the generation of the new Scal site is verified by combined EcoRl, Scal digestion. To ensure purity, plasmid DNA from the positive colonies is used for a second round of transformation of E. coli HB101. Large scale plasmid preparation is made from one such second generation positive colony [Katz et al., J. Bacteriol. 114, 577–591 (1973); Biochemistry 16, 1677–1683 (1977)] and the destruction of the original Scal site and the generation of the new Scal site are verified by DNA sequence analysis using the method of Maxam and Gilbert [Methods Enzym. 65, 499–560 (1980)]. This plasmid is designated pEco0.47ΔScal.

B) Reconstruction of Human t-PA with Mutant Scal site (see FIG. 13)

In this construct the 470 bp EcoRl fragment present on the wild type human t-PA is exchanged for the 470 bp EcoRl fragment containing the mutant Scal site. Plasmid pW349F containing human t-PA cDNA (see above) is digested with Clal and the resulting sticky ends are made blunt by the addition of 50 µm each of dCTP, dGTP and 10 units of DNA polymerase I, Klenow fragment (Boehringer, Mannheim). The reaction is incubated at room temperature for 30 min followed by phenol and ether extraction and ethanol precipition. The pellet is dissolved in water, digested with EcoRl and Scal, and 1.5 kb EcoRl, Scal and 4.3 kb Clal (blunt ended). EcoRl fragments are isolated. These two fragments are mixed with the 470 bp fragment recovered from plasmid pEco0.47ΔScal after EcoRl digestion and ligated as described above at 12° C. overnight. Competent E. coli HB101 cells are transformed with the ligation mix and tetracycline resistant colonies selected on L-agar containing 12.5 µg/ml tetracycline. Colonies containing the 470 bp mutant fragment are identified by colony hybridization using the previously described 31-mer as the probe. DNA from minilysates of several of the positively hybridizing colonies is prepared and the exact nature of the construct is verified by performing appropriate restriction digests. One such plasmid with the desired changes is termed ph•tPAΔScal.

EXAMPLE 6.2

Construction of a u-PA/t-PA Hybrid Molecule; plasmid pUNC•tc (see FIG. 14)

This construct is a hybrid between the noncatalytic region of u-PA (containing the 5' noncoding region, signal, growth factor and the kringle sequences) and the catalytic or enzyme domain of human t-PA.

Urokinase cDNA is prepared from mRNA obtained from human Hep3 cells [cf. T. Maniatis et al., Molecular Cloning (1982), p. 188–246]. A 1.3 kb Smal-BamHl fragment and a 1 kb BamHl-EcoRl fragment of the u-PA cDNA is cloned into the Smal, Ecorl sites of pUN121 [B. Nilsson et al., Nucl Acids. Res. 11, 8019–8030 (1983)] to yield plasmid pcUK176. The restriction endonuclease map of the human u-PA cDNA insert is shown in FIG. The nucleotide sequence and deduced amino acid sequence of the u-PA insert is given in FIG. 3.

Plasmid pcUK176 is digested with Xmal (cf. FIG. 11; Xmal is an isoschizomer of Smal) and Mstl and the 521 bp fragment is isolated. Restriction enzyme Mstl recognizes the DNA sequence TGC GCA (arrows indicate site of cleavage) and produces blunt ends upon digestion; this enzyme therefore cuts u-PA cDNA at nucleotides 520-525, i.e., right after the last cysteine residue (amino acid 131) comprising the kringle [Holmes et al., Biotechnology 3, 923–929 (1985)], and thus cleanly separates the coding sequences for noncatalytic and catalytic regions.

Plasmid ph•tPAΔScal is digested by Scal and Hindlll (Hind lll is present in the vector) and the 1.8 kb fragment recovered. Restriction enzyme Scal recognizes the DNA sequence AGT ACT (arrows indicate site of cleavage) and also yields blunt ends upon digestion. Scal will but ph•tPAΔScal DNA after the serine residue 262 [1 amino acid past the last cysteine of kringle 2; Pennica et al., Nature 301, 214–221 (1983)], hence separating the noncatalytic and the catalytic domains.

The two fragments are mixed and ligated to Xmal, Hindlll cleaved pUC18 vector DNA. After transformation of E. coli HB 101, colonies having the correct insert are identified by colony hybridization using the 2.0 kb BglI fragment of human tPA (cf. FIG. 9) as the probe [the probe is labelled by the random priming method: Feinberg et al., Analyt. Biochem. 132, 6–13 (1983)]. The DNA sequence at the junction of ligation of the u-PA and t-PA fragments is verified by DNA sequence analysis. One correct clone is designated pUNC•tc.

EXAMPLE 6.3

Construction of a t-PA/u-PA Hybrid Molecule; Plasmid ptNC•UC (cf FIG. 15)

This construct is just the reverse of pUNC•tc in that the non-catalytic region of ph•tPAΔScaI (containing 5' noncoding region, leader, finger, growth factor, kringle 1 and kringle 2 domains) is fused to the catalytic domain of human u-PA. Plasmid ph•tPAΔScaI is digested with ScaI and ScaI (cf FIG. 15) and an about 1.0 kb fragment is isolated. Plasid pcUK176 is first digested with BamHI and then partially cleaved with MstI and the about 800 bp fragment recovered. Next, the BamHI digest is cut with EcoRI and the about 1.0 kb fragment is isolated. These three fragments are mixed with pUC19 vector digested with SacI, EcoRI, and ligated. E. coli HB101 is transformed with the ligation mix and colonies having the correct insert are identified by colony hybridization using the same 2.0 kg BglII probe as described above. DNA sequence at the junction of t-PA and u-PA and DNA is verified by DNA sequence analysis. One correct clone is termed ptNC•UC.

EXAMPLE 6.4

Construction of an Expression Vector for use in Mamallian Cells

A) Conversion of the HgiAl site in t-PA cDNA to a HindIII Site

This is achieved in five steps (FIG. 16)

Plasmid pW349 (European Patent Application No. 143,081) is partially cleaved with the restriction enzyme HgiAl by incubation of 20 μg/ml DNA for 1 h at 37° C. with 2 U/ml of the enzyme in the buffer recommended by the manufacturer (Bethesda Research Laboratories) except that it is supplemented with 10 μg/ml ethidium bromide to supprocess secondary cutting of the plasmid. Linearized plasmid DNA is then applied to a 0.8% agarose gel in TBE buffer (TBE: 89 mM Tris-borate pH 6.9 containing 1 mM EDTA), electrophoretically eluted in the same buffer, twice extracted with phenol, twice with chloroform and finally precipitated with alcohol at −20° C. after addition of 0.1 vol. 3M sodium acetate ph 5.2. Pelleted DNA is dissolved at 0.2 mg/ml in Te(TE: 10 mM Tris-HCl pH 7.2 with 01 mM EDTA).

63 μl of linearized DNA is then incubated for 30 min at 37° C. with 15 U of T4 DNA polymerase in ligase buffer [33 mM Tris-acetate (pH 7.9) 66 mM potassium acetate, 10 mM magnesium acetate, 0.5 mM dithiothreitol and 0.1 mg/ml bovine serum albumin] followed by heating 10 min at 60° C. to inactivate the enzyme. The purpose of this incubation is to use the exonucleolytic activity of the T4 polymerase to remove the protruding four nucleotides left after digestion with HgiAl to obtain blunt-ended DNA molecules.

In order to ligate HindIII linkers (CAAGCTTG) to the blunt-ended DNA 6 μl (300 ng) kinased linkers are added to the above solution with 4 μl 10 mM ATP and 3 μl T4 DNA ligase (New England Biolabs, 400 u/μl) followed by a 16 h incubation at 16° C. The ligation is terminated by heating the mixture 10 min. at 68° C., after which the DNA is digested with HindIII and BglII, i.e. 15 μl (135 U) HindIII is added with 1.5 μl 4M NaCl 0.2 μl 1M MgCl₂ and 11 μl 1 mg/ml bovine serum albumin, incubated at 37° C. for 1 h followed by addition of 40 U BglII followed by another 1 h incubation at 37° C. The resulting 177 base pair fragment is purified on a 6% polyacrylamide gel run in TBE, eluted in TNE (TNE: 10 mM Tris-HCl pH 8.8 containing 100 mM NaCl and 1 mM EDTA), absorbed to DEAE cellulose (Whatman DE52), eluted with 1M NaCl in TNE, diluted with 4 volumes of water, precipitated at −20° C. after addition of 2.5 volumes of ethanol and finally dissolved in 17 μl TE (TE: 10 mM Tris-HCl pH 8.0 containing 1 mM EDTA).

Plasmit pRSVneo is a derivative of plasmid pSV2neo [P. J. Southern and P. Berg, J. Mol. Appl. Genet. 1, 327–341 (1982)] in which the SV40 derived PvuII-HindIII fragment has been replaced with a PvuII-HindIII fragment containing the LTR promotor from Rous sarcoma virus in the same manner as pRSVcat was constructed from pSV2cat [C. M. Gorman et al., Proc. Natl. Acad. Sci. USA 79, 6777–6781 (1982)]. 5 μg of this plasmid is cut in a 50 μl volume with 24 U BglII according to the manufacturer's instructions. After a 1 h incubation at 37° C. 40 U HindIII are added and the incubation continued for 1.5 hour after which the large 5.4 kb fragment is purified as described above.

17 μl of the purified 177 bp fragment are ligated for 18 hours at 16° C. to 2 μl (20 ng) of the pRSVneo fragment using 0.25 μl (100 U) T4 ligase in a total volume 22 μl ligase buffer, after which the plasmid DNA is used to transform E. coli according to D. Hanahal [J. Mol. Biol. 166, 557–580 (1983)]. From the resultant ampicillin-resistant strains one is selected containing a plasmid designated ptPA1 with the 177 bp HindIII-BglII fragment as evidence by restriction analysis. 0.1 μg of this plasmid is cut in 60 μl with 16 U BglI as recommended by the manufacturer for 1.5 h at 37° C. To this solution is then added 20 U calf intestinal alkaline phosphatase (Boehringer Mannheim) and the incubation continued for 30 min. after which the DNA is extracted twice with phenol, twice with chloroform and precipitated after adding 0.1 volume 3.0M sodium acetate pH 5.2 and 0.6 volume of isopropanol, dissolved in TE, further purified by agarose gel electrophoresis as described above, twice extracted with phenol, twice with chloroform, precipitated at −20° C. after addition of 2.5 volumes ethanol and 0.1 vol 3M sodium acetate pH 5.2 and finally dissolved in 30 μl TE. The 2.1 kb tPA BglII fragment is then cut out of 5 μg pW349F in a 25 μl reaction using 20 U BglII for 2 h at 37° C., purified on a 0.8% agarose gel, electrophoretically eluted as described above, twice extracted with phenol, twice with chloroform, precipitated at −20° C. after addition of 2.5 volumes ethanol and 0.1 vol. 3M sodium acetate pH 5.2 and dissolved at a concentration of 8 ng/μl in TE. 1 μl of the t-PA fragment is then ligated in a 10 μl reaction to 7.5 ng BglII cut vector DNA using 100 U T4 ligase (Biolabs) for 17 h at 16° C. and subsequently transformed into E. coli. One of the resultant clones, designated pD02, contains the t-PA BglII fragment inserted in such as way that the plasmid contains a continuous open reading frame for human t-PA.

B) Combination of the t-PA cDNA with the Beta Globin Fragment

Plasmid pDO10 (FIG. 10) is constructed by coligating three DNA fragments: (i) a 2.1 kb fragment starting with a HindIII site and terminating with a BglII site containing the whole t-PA coding sequence is isolated from an agarose gel on which is loaded 10 μg of pD02 DNA cut partially with BglII and completely with HindIII. (ii) pUB is a plamid containing the rabbit beta globin gene [A. Van Ooyen et al., Science 206, 337 (1979)] subcloned as a BglII partial digest into the BamHl site of plasmid pUC9 [J. Vieira and J. Messing, containing the second intron and the polyadenylation site is excised and purified by agarose gel electrophoresis. (iii) Vector pD01 is built up, in anticlockwise order from the HimdIII site (FIG. 10) of the HindIII-AccI fragment of pBR322 with includes the origin of replication, a 0.3 kb fragment containing the enhancer of human cytomegalovirus (HCMV) terminating in a synthetic XbaI site followed by a second copy of this enhancer attached to the homologous promoter terminating at a synthetic HindIII site. This vector DNA is cut with HindIII and the 6.3 kb linear plasmid is purified by agarose gel electrophoresis.

C) Inserging the tPA/Globin Combination into pSP62Pst33 (see FIG. 18)

pSP62Pst33 (FIG. 18) is a plasmid containing a 2.1 kb PstI fragment of the mouse cytomegalovirus (MCMV) DNA, which includes the viral immediate early (IE) promoter, inserted into the PstI site of plasmid pSP62 (Boehringer Mannheim) as indicated in the figure. Into the HindIII site of pSP62Pst33 is inserted the HindIII fragment from pD010. A plasmid, pCGA26, is selected in which the t-PA coding sequence is inserted such that is can be transcribed in "sense" orientation from the MCMV IE promoter.

D) Inserting the MCMV/tPA/Globin Unit into pFASV2911neo (see FIG. 19)

Plasmid pSV2911neo (F. Asselbergs at al., J. Mol. Biol. 189, 401-411 (1986)] contains the neomycin (neo) phosphotransferase gene from transposon TN5 in an SV40 expression cassette (FIG. 19). Thus it confers resistance to neomycin and kanamycin when introduced into mammalian tissure culture cells. pSV2911neo DNA is prepared for cloning by cutting with BamHl, treating with calf intestinal alkaline phosphatase, two extractions with phenol, two with chloroform, precipitation with alcohol and finally dissolved in TE. Plasmid pCGA26 is cut with restriction enzyme AccI, which cuts the sequence of GT/ACAC at position 345 in the MCMV enhancer/promoter region [K. Doersch-Haessler at al., Proc. Natl. Acad. Sci. USA 82, 8325-8329 (1985)] and the sequence GT/CGAC (can also be cut with SalI) behind the globin part. The two base overhangs resulting after cutting are filled in with E. coli (large fragment) DNA polymerase 1, the now blunt ends are ligated to BamHl liners (CGGATCCG) and these cut with HamHl enzyme. The 3.8 kb fragment carrying the MCMV/tPA/globin unit now with BamHl ends in purified via an agarose gel and then ligated to the pSV2911neo DNA prepared as described above to yield expression plasmid pCGA28.

E) Expression Vectors Derived from pCGA28 pCGA42 is a derivative of pCGA28 in which the neo coding sequence (betwee the BglII site and SmaI site) is replaced by the coding sequence of a hygromycin resistance gene. This is achieved (see FIG. 20) by cutting plasmid pSV2911neo at its unique SmaI site, ligating a BglII linker (CACATCTG) to the DNA following by cutting with BglII. The resulting large DNA fragment consisting of the vector minus the neo coding sequence is purified on an agarose gel and ligated to the small BamHl fragment from plasmid pLG89 [L. Gritz et al., Gene 25, 179-188 (1983)] equally purified on an agarose gel, leading to plasmids pCGA25C and pCGA25d, which contain the hygromycin phosphotransferase gene in the sense and antisense orientation, respectively. When transfected into CHO DUKXB1 cells on standard conditions (see Example 16), pCGA25c gives 60 colonies/μg DNA resistant to 0.2 μg/ml hygromycin B, a concentration which kills CHO cells containing a plasmid not encoding hygromycin resistance, for examply pCGAS28. In pCGA25c the sequences encoding hygromycin-B resistance are located such that in E. coli they are transcribed from the Tn5 promoter (which in transposon Tn5 transcribes the kanamycin resistance gene). Thus, a 2.5 ml culture of Luria broth (LB) containing 40 mg/l hygromycin-B inoculated with 0.05 ml of an overnight, i.e. saturated culture of E. coli DH1 bacteria (grown under 50 mg/l ampicillin selection) reaches after 3 h aerated culture at 37° C. an at least 10 times higher bacterial density, then when bacteria with plasmids not containing a hygromycin gene functional in E. coli, such as pCGA25d, pCGA28 or pAT153 [A. J. Twigg at al., Nature 283, 216-218 (1980)], are tested. The functionality of the hygromycin-B resistance gene both in animal tissue culture cells and in E. coli greatly facilitates the use of plasmid pCGA25c and its derivatives. Plasmid pCGA42 is then constructed by inserting the BamHl fragment from pCGA28 containing the MCMV/t-PA/beta-globin cassette into pCGA25c. Its use is to transfer t-PA expressing gene into cells which cannot be transformed to geneticin resistance or which are already geneticin resistant. Also pCGA42 is capable of expressing its hygromycin gene in E. coli, allowing pCGA42 containing E. coli DH1 to grow to densities a least 10 times higher than, for example, pCGA28 containing E. coli, when tested as described above.

Plasmid pCGA28 contains two SacI sites, one originally part of a linker just behind the MCMV promoter, the other in the t-PA cDNA. The sequence between the SacI sites is deleted by cutting first with the restriction enzyme, purifying the large fragment via an agarose gel and circularizing this linear DNA using T4 DNA ligase, forming plasmid pCGA44 (see FIG. 19). Any cDNA cloned into the proper orientation into the not unique SacI site of pCGA44 effectively replace the t-PA coding sequence in pCGA28 and is efficiently expressed.

pCGA42d is derived from pCGA42 by deleting the 1.4 kb SacI fragment (see FIG. 20). Into the now unique SacI site cDNAs other than t-PA cDNA can be inserted and expressed at high levels in tissue culture cells.

EXAMPLE 6.5

Insertion of u-PA, t-PA and Hybrid PA cDNAs into Expression Vector pCGA28

A) Insertion of t-PA cDNA (see FIG. 22)

In this construct, the t-PA cDNA fragment from plasmid ph.tPAΔScaI is inserted into pCGA28. This construct is deemed necessary to serve as a control for any changes that might inadvertently have occurred during the restructuring of the ScaI site. The 1.4 kb ScaI fragment is recovered from plasmid ph.tPAΔScaI after SacI digestion. The expression vector pCGA28 is also cleaved with ScaI and the 8.2 kb vector fragment is isolated and dephosphorylated in a 100 μl reaction mixture containing 0.1 mM Tris pH 8.0, 0.1% SDS and 0.02 units bacterial alkaline phosphatase. Following incubation at 60° C. for 30 min, the reaction is phenol and ether extracted twice and then ethanol precipitated. The pellet is dissolved in water and an aliquot of it used for ligation to the 1.4 kg SacI fragment from ph.tPAΔSacI. The ligation mix is used to transform E. coli HB101 and minilysate DNA prepared from ampicillin-resistant colonies is digested with appropriate restriction enzymes to verify if the SacI insert is in the desired orientation. The plasmid having the desired orientation is called pBR1A. The plasmid with the SacI fragment in the opposite orientation is termed pBR1B.

B) Insertion of Hybrid UPA$^A$TPA$^B$ cDNA (see FIG. 23)

In this construct, the hybrid UPA$^A$TPA$^B$ cDNA fragment from plasmid pUNC.tc is inserted into the expression vector pCGA28. pUNC.tc DNA is digested with SmaI (cf. FIG. 14), the 1.24 kb fragment is isolated and ligated to SacI digested, dephosphorylated 8.2 kb pCGA28 vector DNA. E. coli HB101 cells are transformed with the ligation mix and colonies containing the SacI insert in the desired orientation identified by performing restriction digests on minilysate DNA. The plasmid with the pUNC.tc DNA insert in the desired orientation is designated pBR2A and the one with the opposite orientation pBR2B.

C) Insertion of u-PA cDNA (see FIG. 24)

In this construct, human u-PA DNA is inserted into the expression vector pCGA28 and together with pBR1 this plasmid serves as the parent plasmid control and confirms the usefulness of pCGA28-type vectors. Plasmid pcUK176 is digested with SmaI, AhaIII (cf. FIG. 11), the 2.25 kb fragment isolated, and ligated to phosphorylated SacI linker as described above. Following SacI digestion, the 2.25 kb fragment is recovered and ligated to Sac 1 digested, dephosphorylated 8.2 kb pCGA28 DNA fragment. E. coli HB101 is transformed and colonies harbouring desired plasmid identified by digesting minilysate DNA with restriction enzymes. The plasmid with the human u-PA DNA in the correct orientation is designated pBR23A and that in the opposite orientation pBR3B.

D) Insertion of Hybrid TPA$^A$UPA$^B$ cDNA (FIG. 25)

Here, the hybrid TPA$^A$UPA$^B$ cDNA from plasmid ptNC.UC is inserted into the expression vector pCGA28. The 2.75 kb SmaI (present in the vector), AhaIII fragment is isolated from the ptNC.UC DNA, ligated to phosphorylated SacI linker, the linker ligated 2.75 kb fragment recovered and ligated to SacI digested, dephosphorylated vector DNA and the desired colonies identified as described above. The plasmid with the ptNC.UC DNA insert in the correct orientation is called pBR4A.

EXAMPLE 6.6

Construction of a Yeast Expression Vector Containing the PH05 Promoter, the Invertase Signal Sequence and the t-PA Coding Region A) Synthesis of Oligodeoxyribonucleotides for Invertase Signal Sequence Four oligodeoxyribonucleotides: 1-1, 1-2, 1-3, 1-4 are synthesized by DNA synthesizer (model 380B Applied Biosystems). After deblocking the synthetic fragments are purified on a 12% polyacrylamide gel containing 8M urea. Salt-free pure oligodeoxyribonucleotides are obtained using Sep. Pak (Waters Associates). These fragments constitute a duplex which encodes the invertase signal sequence with the frequently used yeast codons.

```
                               HindIII
           EcoRI    Met Leu Leu Gln Ala Phe Leu Phe Leu Leu
I-1    5'  AATTCATGCTTTTGCAAGCTTTCCTTTTCCTTTT  3'
I-2        3'  GTACGAAAACGTTCGAAAGGAAAAGGAAAACCGAC  5'

Ala Gly Phe Ala Ala Lys Ile Ser Ala
I-3    5'  GGCTGGTTTTGCAGCCAAAATATCTGCATCTTAGCGTC  3'
I-4        3'  CAAAACGTCGGTTTTATAGACGTAGAATCGCAGAGCT  5'
                                                HgaI
                                                     XhoI
```

B) Subcloning of the Invertase Signal Sequence in Plasmid p31 a) Preparation of Vector 1.5 μg of p31R/SS-TPAΔ2 (European Patent Application No. 143,081) is digested with 10 U of EcoRI (Boehringer) in 50 μl of 10 mM Tris. HCl pH 7.5, 6 mM MgCl$_2$, 100 mM NaCl, 6 mM mercaptoethanol for one hour at 37° C. After adding 1 μl of 2.5M NaCl, 10 U of XhoI (Boehringer) are added as incubated at 37° C. for one hour. The 4.2 kb vector is isolated on a 0.8% preparative agarose gel. The gel slice is transferred to a Micro Colloidor tube (Sartorius GmbH), covered with 200 μl of TE and electroeluted (electrophoresed at 90 mA for 50 min). The TE solution is collected at precipitated in 2.5 volumes of absolute ethanol after the addition of 0.1 volume 10×TNE. The DNA pellet is washed with cold 80% ethanol and dried in vacuum. The DNA is resuspended in 6 μl TE (40 pmoles/μl).

b) Annealing Oligodeoxyribonucleotides (l-1, 1-2, 1-3, 1-4,), Kination and Ligation with Vector A solution containing 10 pmoles of each of the four deoxyribonucleotides in 10 μl of 0.5M Tris.HCl pH 8 is incubated at 95° C. for 5 minutes on a water bath. The water bath is slowly cooled to 30° C. over a period of 5 hours. To this annealed mixture is added 2 μl each of 0.1M MgCl$_2$, 0.1M NaCl, 30 mM DTT, 4 mM ATP and 8 U (1 μl) of polynucleotide kinase (Boehringer). Kination is carried out at 37° C. for one hour. The anealed, kinased oligodeoxyribonucleotides and 60 pmoles of p31R/SS-TPAΔ2 cut vector (1.5 μl) are ligated with 400 U (1 μl) of T4 DNA ligase (Biolabs) at 14° C. for 17 hours. The reaction is stopped by incubation at 65° C. for 10 min. 10 μl of this ligation mixture is used for transformation of E. coli HB101 Ca$^{++}$ cells [M. Dagert and S. D. Ehrlich, Gene 56, 23–28 (1979)]. 20 amp-$^R$colonies are picked. DNA is prepared by the quick isolation procedure (D. S. Holmes and M. Quigley. Anal Biochem. 114 193–197 (1981)]. DNA is digested with EcoRI and XhoI, radiolabelled at the EcoRI end and analysed on a 6% polyacrylamide gel containing 8M urea using radiolabelled pBR322 HaeIII cut DNA as marker. Correct size bands are observed for DNA obtained from all the 20 clones. One clone is grown in 100 ml LB medium containing 100 μg/ml of ampicillin. Plasmid DNA is isolated and is referred to as p31RIT-12.

C) Construction of pJDB207/PH05-1-TPA (see FIG. 26)

a) Preparation of Vector

Three μg of pJDB207/PH05-TPA18 (European Patent Application No. 143,081) is incubated at 37° C. for one hour with 10 U of BamHI in 50 μl of 10 mM Tris.Hcl pH 7.5, 6 mM MgCl₂, 100 mM NaCl, 6 mM mercapthoethanol. An aliquot is checked on a 1% agarose gel in TBE buffer to confirm complete digestion. The digest is incubated at 65° C. for 10 min. Then 0.5 μl of 5M NaCl is added followed by 15 U of XhoI (Boehringer). This is incubated at 37° C. for one hour. The 6.8 kb vector is isolated on a 0.8% preparative agarose gel. The DNA is extracted by electroelution and after precipitation dissolved in TE.

b) XhoI Digest of p31/PH05-TPA18

Thirty μg of p31/PH05-TPA18 (European Patent Application No. 143,081) are incubated at 37° C. for one hour with 60 U of XhoI (15 U/μl) in 200 μl of 10 mM Tris.HCl pH 8, mM MgCl₂ 150 mM NaCl, 6 mM mercaptoethanol, extracted with an equal volume of phenol-chloroform, and precipitated in ethanol.

c) Partial PstI Digest of XhoI Cut p31/PH05-TPA18

The precipitated XhoI cut p31/PH05-TPA18 DNA is resuspended in 250 μl of 10 mM Tris•HCl pH 7.5, 6 mM MgCl₂, 50 mM NaCl, 6 mM mercaptoethanol, 2.5 mg ethidium bromide, incubated at 37° C. for 35 minutes with 22.5 U of PstI, and extracted with an equal volume of phenol, followed by an equal volume of chloroform-isoamylalcohol (50:1). The 1.6 kb fragment is isolated on a 1% preparative agarose gel. The DNA is extracted by electroelution and precipitated [insert 1].

d) SalI-XhII Digest of p31/RIT-12

Thirty μg p31RIT-12 are incubated at 37° C. for one hour with 60 U of SalI (Boehringer 12 U/μl) and 60 U of XhoI (15 U/μl) in 200 μl of 10 mM Tris.HCl pH 8.6 mM MgCl₂, 150 mM NaCl, 6 mM mercaptoethanol, extracted with an equal volume of phenol-chloroform and precipitated in ethanol. The 869 bp fragment is isolated on a 1.2% preparative agarose gel. The DNA is extracted by electroelution desalted over DE-52, and precipitated in ethanol.

e) HgaI Digest of SalI-XhoI Cut 331RIT-12

SalI-XhoI cut p31RIT-12 is resuspended in 100 μl of 6 mM Tris.Hcl pH 7.5, 10 mM MgCl₂, 50 mM NaCl, 1 mM dithiothreitol, 10 mg bovine serum albumin and is incubated at 37° C. for one hour with 6 U of HgaI (Biolabs, 0.5 U/μl). The 600 bp fragment is isolated on a 1.2% agarose gel. The DNA is extracted by electroelution and precipitated in ethanol.

f) Annealing of Linker Oligonucleotides 90 pmoles of two oligodeoxyribonucleotides having the sequences

```
    HgaI                          PstI
5'  CTGCATCTTACCAAGTGATCTGCA  3'
3'       AGAATGGTTCACTAG      5'
``` are suspended in 10 μl of 0.5 mM Tris.HCl pH 8 in a siliconized Eppendorf tube. The solution is incubated at 95° C. for 5 min and then slowly cooled to room temperature overnight.

g) Kination of Linker

To the above solution is added 2 μl of 0.1M KCl, 2 μl of 0.1M MgCl₂, 3 μl of 30 mM DTT, 1 μl of 200 mM ATP, 8 U of polynucleotide (8 U/μl). This is incubated at 37° C. for one hour.

h) Ligation of the HgaI Fragment from p31RIT-12 with the Kinased Linker

The kinased linker solution is transferred to a tube containing the dry HgaI fragment, and 400 U of T₄ DNA ligase is then added. The solution is incubated at room temperature (21°-22° C.) for 90 minutes, diluted to 100 μl with TE and extracted with an equal volume of phenol-chloroform. The fragment is precipitated by adding 0.6 volume is isopropanol and 0.1 volume of 3M sodium acetate at room temperature to the aqueous solution.

i) BamHI-PstI Digest of Above

The above dry DNA is digested with 10 U of BamHI and 10 U of PstI in 20 μl of 10 mM Tris.HCl. pH 7.5, 100 mM MgCl₂, 6 mM mercaptoethanol for one hour at 37° C. After dilution to 100 μl the solution is extracted with an equal volume of phenol-chloroform, and the aqueous layer is precipitated in isopropanol [insert 2].

j) Ligation of the Three Fragments 100 fmoles of pJdB207/PH05-TPA18 BamHI-XhoI cut vector fragment, 200 fmoles of each of the other two insert fragments [1 and 2] are ligated in 10 82 1 of 50 mM Tris.HCl pH 7.5, 10 mM MgCl₂, 10 mM DTT, 2 mM ATP, 0.5 μg gelatin with 400 U of T₄ DNA ligase for 16 hours at 15° C. The reaction is stopped by incubation at 65° C. for 10 min. 5 μl of this ligation mixture is used for transformation of E. coli HB101 Ca⁺⁺ cells. 10 amp$^R$ colonies are picked and DNA is prepared by the quick isolation procedure. On analysis with EcoRI, PstI and BamhI-HindIII correct size fragments are observed. One clone is grown in 100 ml of LB medium containing 100 μg/ml of ampicillin. Plasmid DNA is isolated and is referred to as pJDB 207/PH05-1-TPA.

EXAMPLE 6.7

Construction of Plasmid pCS16/UPa Comprising the u-PA Coding Region

A) Construction of Plasmid pCS16 (see FIG. 27)

A 1.5 kb PstI-BamHI fragment of plasmid pUN121 [B. Nilsson et al., Nucl. Acids Res. 11, 8019-8030 (1983)] comprising the cI gene of phage lambda and part of the tetracyclin resistance gene is cloned into pUC18 [J. Norrander et al., Gene 26, 101-106 (1983)], cut with PstI and BamHI. The resulting clone is digested with PstI. The 3' overhanging ends are removed in a reaction with T₄ DNA polymerase and XhoI linkers are ligated to the blunt ends. After digestion with XhoI the molecule is recircularised by ligation. An aliquot of the ligation mixture is used to transform Ca⁺⁺ treated E. coli HB101 cells. The DNA of individual ampicillin resistant, transformed colonies is analysed. One of several correct clones is chosen and referred to as pCS16.

B) Construction of Plasmid pCS16/UPA (see FIG. 28)

The urokinase cDNA as comprised in plasmid pcUK176 (see Example 6.2 is subcloned in plasmid pCS16. The subcloned cDNA extends from the SmaI site in the 5' nontranslated region (FIG. 11) to the PvuII site at nucleotide positions 1439-1444 in the 3' nontranslated region (numbering according to FIG. 10).

15 μg of plasmid pcUK176 are digested with PvuII. The 379 bp PvuII fragment is isolated from other fragments on a 1.5% agarose gel in Tris-borate-EDTA buffer pH 8.3. The DNA is electroeluted, purified by DE52 (Whatman) ion exchange chromatography and precipitated by ethanol. 1.2 μg of single stranded XhoI linkers (5'-CCTCGAGG-3') are phosphorylated at their 5' ends, heated for 10 min at 75° C., self annealed during cooling to room temperature and stored at −20° C. 0.9 μg of the kinased, double stranded XhoI linkers are ligated at an 80-fold molar excess to the blunt ends of the 379 bp PvuII fragment of pcUK176 (see above) in 20 μl of 60 mM Tris-HCl pH 7.5, 10 mM MgCl2, 5 mM DTT, 3.5 mM ATP and 400 units of T4 DNA ligase (Biolabs) at 15° C. for 16 hours. The mixture is heated for 10 min at 85° C. Excess linker molecules are removed by precipitation with 0.54 volumes of isopropanol in the presence of 10 mM EDTA and 300 mM sodium acetate pH 6.0 for 30 min at room temperature. The DNA is digested with XhoI and BamHI. A 121 bp Bam-HI-XhoI fragment is isolated on a 1.5% agarose gel in Tris-borate-EDTA buffer pH 8.3 6 μg of plasmid pcUK176 are digested with SmaI and BamHI. A 1.3 kb SmaI-BamHI fragment comprising most of the u-PA coding sequence is isolated. 6 μg of plasmid pCS16 are digested with SmaI and XhoI. The 2.7 kb vector fragment is isolated. The DNA fragments are electroeluted from the gel and ethanol precipitated. 0.2 pmoles of the 1.3 kb SmaI-BamHI fragment, 0.2 pmoles of the 121 bp BamHI-XhoI fragment (both fragments together comprise the full u-PA coding sequence) and 0.1 pmoles of the 2.7 kb vector fragment are ligated in 10 μl of 60 mM Tris.HCl pH 7.5, 10 mM MgCl2, 5 mM DTT, 3.5 mM ATP and 400 units of T4 DNA ligase at 15° C. One and 3 μl aliquots of the ligation mixture are added to 100 μl of Ca++ treated E. coli HB101 cells. Transformation is carried out as described [A. Hinnen et. al., Proc. Natl. Acad. Sci. USA 75, 1929 (1978)]. 12 ampicillin resistant colonies are grown in LB medium containing 100 mg/1 ampicillin. DNA is isolated according to Holmes et al. ]Anal. Biochem. 114, 193 (1981)] and analysed by EcoRI, PvuII and XhoI restriction digests. One clone with the expected restriction fragments is referred to as pCS16/UPA.

EXAMPLE 6.8

Construction of Plasmid pJDB207/PH05-l-UPA (FIG. 29)

pJDB207/PO05-l-UPA contains the PH05 promoter, the invertase signal sequence, the coding sequence of mature urokinase and the PH05 transcription terminator in tandem array clones into the pJDB207 yeast expression vector.

20 μg of plasmid pCS16/UPA are digested to completion with 40 units of EcoRI. After phenol extraction and ethanol precipitation the EcoRI digested DNA is further cut by TaqI at 65° C. The resulting fragments are separated on a preparative 1.2% agarose gel. The 462 bp TaqI-EcoRI fragment is isolated by electroelution from the gel and ethanol precipitation.

An oligodesocyribonucleotide linker of the formula

5'-CTGCAAGCAATGAACTTCATCAAGTT-
CCAT-3' (I)

3'-TCGTTACTTGAAGTAGTTCAAGGTAGC-
5' (II)

is ligated to the TaqI site of the DNA fragment. The linker restores the 5' terminus of the coding sequence of mature u-PA (nucleo-tides 130–154. FIG. 10) and establishes the in frame fusion to the invertase signal sequence. The 5'-CTGCA sequence of the linker fits the corresponding 3' recessed end of the invertase signal sequence created by HgaI cleavage.

300 pmoles each of the oligodesoxynucleotides I and II are phosphorylated and annealed. 5.25 μg (600 pmoles) of phosphorylated, double-stranded linker DNA are ligated to 1.7 μg (5.6 pmoles) of the 482 bp TaqI-EcoRI fragment (see above) in 175 μl of 60 mM Tris-HCl pH 7.5, 10 mM MgCl2, 1 mM ATP, 5 mM DTT and 800 units of T4 DNA ligase at 15° C. for 16 hours. T4 DNA ligase is inactivated for 10 min at 85° C. The excess of linkers is removed by precipitation in the presence of 10 mM EDTA, 300 mM sodium acetate pH 6.0 and 0.54 volumes of isopropanol. The DNA is digested with PstI. An unique 312 bp fragment is isolated containing the linker attached to DNA sequences coding for u-PA up to nucleotide 436 (PstI site, see FIG. 3). The DNA fragment is purified by electroelution and precipitation with ethanol.

Plasmid pCS16/UPA is digested with XhoI and PstI. A 1007 bp PstI-XhoI fragment is isolated and purified. This fragment contains most of the coding sequence for urokinase.

Plasmid p31RIT-12 (see Example 6B) is digested with SalI and XhoI. An 822 bp SalI-XhoI fragment is isolated from the gel by electroelution and ethanol precipitation. The fragment is further digested with BamHI and HgaI. A 591 bp BamHI-HgaI fragment is isolated which contains the PH05 promoter region and the invertase signal sequence.

Plasmid pJDB207/PH05-TPA18 (see European Patent Application No. 143,081) is digested with BamHI and XhoI. The 6.8 kb vector fragment is isolated on a preparative 0.6% agarose gel in Triacetate buffer pH 8.2. The DNA is electroeluted and precipitated with ethanol.

All DNA fragments are resuspended in H2O at a concentration of 0.1 pmoles/μl 0.2 pmoles of the 591 bp BamHI-HgaI fragment, 0.2 pmoles of the 312 pb HgaI-PstI fragment, 0.2 pmoles of the 1007 pb PstI-XhoI fragment and 0.1 pmoles of the 6.8 kb BamHI-XhoI vector fragment are ligated for 15 h at 15° C. in 10 μl of 50 mM Tris•HCl pH 7.5, 10 mM MgCl2, 5 mM DTT, 1 mM ATP and 400 units of T4 DNA ligase. One μl of the ligation mixture is used to transform E. coli HB101 Ca++ cells. 12 amp$^R$ colonies are picked and grown in LB medium containing 100 mg/1 of ampicillin. DNA is prepared by the quick isolation procedure [D. S. Holmes et al., Anal. Biochem. 144, 193 (1981)]. On restriction digests of the plasmid DNA with HindIII and EcoRI the expected restrictuion fragments are observed. Plasmid DNA of a single clone is selected and referred to as pJDB207/PH05-l-UPA.

EXAMPLE 6.9

A t-PA/u-PA Hybrid Plasminogen Activator with the t-PA A-chain domains and u-PA B-chain (Primary DNA Construct)

Another approach for the construction of an in frame fusion of DNA sequences coding for the A-chain of t-PA and the B-chain of u-PA at a predetermined position consists in two steps: Firstly, convenient restriction fragments with the coding sequences are ligated. DNA is prepared in E. coli and subcloned in M13 to obtain signle-stranded templates. In a second step excess necleotide sequences are removed by in vitro mutagenesis. The exact in frame junction between the t-PA A-chain and the u-PA B-chain is at the activation site. The mutant DNA is subcloned in a suitable expression vector for yeast and mammalian cell lines.

a) Isolation of a DNA Fragment Coding for the t-PA A-chain

10 μg of plasmid pJDB207/PH05-l-TPA (see Example 6.6) are digested with BamHI and PvuII. The 1.7 kb BamHI-PvuII fragment is separated on a 0.8% agarose gel in Tris-borate-EDTA buffer pH 8.3. The DNA fragment contains the PH05 promoter, the invertase signal sequence and the coding sequence of mature t-PA up to the PvuII restriction site [cf. FIG. 8; nucleotide positions 1305-1310]. The DNA is electroeluted, precipitation with ethanol and resuspended in $H_2O$ at a concentration of 0.1 pmoles/μl.

b) Isolation of a DNA Fragment Coding for the u-PA B-chain

Plasmid pCS16/UPA (see Example 6.7) is digested with BalI (cf. FIGS. 11 and 10) nucleotide positions 573-578) and XhoI. The 868 bp BalI-XhoI fragment is isolated as above and resuspended in $H_2O$ at a concentration of 0.1 pmole/μl.

c) Ligation of Fragments to Vector Fragment

Plasmid pJDB207/PH05-TPA18 (European Patent Application No. 143,081) is digested with BamHI and XhoI. The 6.7 kb vector fragment is isolated on a 0.8% agarose gel in Tris-acetate pH 8.2. The DNA is electroeluted, ethanol precipitated and resuspended in $H_2O$ at a concentration of 0.1 pmole/μl.

0.2 pmoles of the 1.7 kb BamHI-PvuII fragment, 0.2 pmoles of the 868 bp BalI-XhoI fragment and 0.1 pmoles of the 6.7 kb BamHI-XhoI vector fragment are ligated in 10 μl of 60 mM Tris-HCl pH 7.5, 10 mM $MgCl_2$, 5 mM-DTT, 3.5 mM ATP and 400 units of $T_4$ DNA ligase (Biolabs) at 15° C. for 16 hours. One and 3 μl aliquots of the ligation mixture are added to 100 μl of $Ca^{++}$ treated E. Coli HB101 cells. Transformation is carried out as usual.

Six transformed, ampicillin resistant colonies are grown in LB medium containing 100 mg/l ampicillin. Plasmid DNA is prepared according to the method of Holmes et al. [Analyt. Biochem. 114, 193 (1981)] and analysed by restriction digests with BamHI and PstI. One clone with the expected restriction fragments if referred to as pJDB207/PH05-l-TPA$^A$UPS$^B$.

EXAMPLE 6.10

A u-PA/t-PA Hybrid Plasminogen Activator with the u-PA A-chain Domains and t-PA B-chain (Primary DNA Construct)

The primary hybrid DNA construct comprises the u-PA nucleotide sequences from the SmaI site to the EcoRI site (see FIG. 11) joined to t-PA nucleotide sequences from the ScaI site (positions 940-945) to the XhoI site introduced at position 1800 via an XhoI linker. The resulting hybrid DNA sequence contains excess nucleotides which are removed by in vitro mutagenesis. The exact, in frame junction between the u-PA A-chain and the t-PA B-chain is at the activation site.

a) Isolation of a DNA Fragment Coding for the u-PA A-chain

7 μg of plasmid pCS16/UPA are digested with EcoRI. The sticky ends of the resulting 3 fragments are converted to blunt ends by a fill-in reaction with 7.5 units of Klenow DNA polymerase (BRL) in the presence of 60 mM Tris.HCl pH 7.5, 10 mM $MgCl_2$, 0.1 mM dATP and 0.1 mM dTTP for 30 min at 25° C. The reaction is stopped by the addition of EDTA to a final concentration of 12.5 mM. The DNA is further digested with KpnI. A 619 kpnI-blunt [EcoRI] end fragment is isolated on a 1.5% agarose gel in Tris-borate-EDTA buffer pH 8.3, electroeluted and ethanol precipitated.

b) Isolation of a DNA Fragment Coding for the t-PA B-chain

6 μg of plasmid pJDB207/PH05-TPA18 are digested with ScaI and XhoI. A 860 bp fragment is isolated on a 1.2% agarose gel in Tris-borate EDTA buffer pH 8.3, electroeluted and ethanol precipitated.

c) Ligation of the DNA Fragments to a pUC18 Derived Vector

5 μg of plasmid pCS16/UPA (see Example 6.7) are digested with KpnI and XhoI. The resulting 2.7 kb fragment is isolated on a 0.8% agarose gel in Tris-borate-EDTA buffer pH 8.3. The DNA is electroeluted and ethanol precipitated. All DNA fragments are resuspended in $H_2O$ at a concentration of 0.1 pmoles/μl. 0.2 pmoles of the 619 bp Kpn-blunt end u-PA fragment, 0.2 pmoles of the 860 bp ScaI-XhoI t-PA fragment and 0.1 pmoles of the 2.7 kb KpnI-XhoI vector fragment are ligated as described above (Example 6.9), $Ca^{++}$ treated E. coli HB101 cells are transformed. 12 transformed, ampicillin resistant colonies are grown in LB medium supplemented with ampicillin (100 mg/l). DNA is prepared according to Holmes et al. (supra) and analysed by restriction digests with EcoRI and PstI. A single clone with the expected restriction fragments is referred to as pCS16/UPA$^A$TPA$^B$.

EXAMPLE 6.11

A u-PA/t-PA Hybrid Plasminogen Activator with the Second Kringle and the Catalytic B-chain of t-PA (Primary Construct)

A hybrid plasminogen activator gene comprising the DNA sequences of the urokinase "growth factor like" (U)-domain, the second kringle domain ($K_2$) of t-PA and the catalytic B-chain of t-PA is constructed in the following way: Two DNA restriction fragments coding for the u-PA growth factor domain and the t-PA $K_2$ kringle and B-chain, respectively, are ligated and inserted into plasmid pCS16. The resulting clone is called pCS16/UK$_2$TPA$^B$. A fragment containing the u-PA and t-PA coding sequences in subcloned in M13. In vitro mutagenesis is performed on single strand DNA to remove excess DNA sequences at the junction between u-PA and t-PA sequences.

5 μg of plasmid pCS16/UPA are digested with NcoI (nucleotide positions 326-331, see FIG. 11). The sticky ends of the restriction fragments are filled in a reaction with 5 units of Klenow DNA polymerase 1 (BRL) in the presence of 0.1 mM each of dATP, dTTP, dCTP, dGTP, 60 mM Tris.HCl pH 7.5 10 mM MgCli2 in 50 μl for 30 min at room temperature. The reaction is stopped by the addition of EDTA to a final concentration of 12.5 mM. The DNA is ethanol precipitated and further digested with XhoI. The 3 kb XhoI-blunt end [NcoI] fragment is isolated on a 0.8% agarose gel in Tris-borate-EDTA pH 8.3, electroeluted and ethanol precipitated. This fragment contains the pCS16 vector and coding sequence for the u-PA growth factor domain. 10 μg of plasmid pJDB207/PH05-TPA18 (European patent application No. 143,081) are digested with BsXI

[nucleotide positions 577–588]. The linear DNA fragment with 3' overhanging ends is incubated with 10 units of T4 DNA polymerase (BRL) in 100 μl of 33 mM Tris-acetate pH 7.9, 66 mM potassium acetate, 10 mM magnesium acetate, 0.5 mM DTT and 0.1 mg/ml of bovine serum albunim for 2. min at 37° C. Then incubation is continued for 35 min at 37° C. in the presence of 0.1 mM each of dATP, dCTP, dTTP, dGTP in a total volume of 200 μl. The DNA is ethanol precipitated and further digested with XhoI. The 1.2 kb blunt end [BsXI]-XhoI fragment is separated on a 0.8% agarose gel, electroeluted and ethanol precipitated. This fragment contains the coding sequence for K2 and the B-chain of t-PA.

0.2 pmoles of the 1.2 kb t-PA fragment and 0.1 pmoles of the 3 kb u-PA/vector fragment (see above) are ligated as described. Aliquots of the ligation mixture are used to transform competent E-coli HB101 cells. Ampicillin-resistant colonies are selected on LB agar plates containing 100 mg/l ampicillin. DNA is prepared from individual transformants and analysed by ScaI and SmaI restriction digests. A clone containing the 0.5 kb ScaI and the 1.55 kb SmaI junction fragments is selected and referred to as pCS16/UK$_2$TPA$^B$.

EXAMPLE 6.12

A t-PA/u-PA Hybrid Plasminogen Activator with the Second Kringle of t-PA and the Catalytic B-chain of u-PA (Primary Construct)

A hybrid plasminogen activator gene comprising the DNA sequences of the urokinase "growth factor like" (U) domain, the second kringle (K2) of t-PA and the catalytic B-chain of u-PA is constructed by a method analogous to the one described in Example 6.11.

Construction of Plasmid pCS16/UK$_2$UPA$^B$

5 μg of plasmid pCS16/UPA are digested with BglII and NcoI (nucleotide positions 391–396 and 326–331, respectively, see FIG. 11). The sticky ends of the restriction fragments are filled in a reaction with Klenow DNA polymerase 1 (BRL) as described above. The 4.2 kb DNA fragment which blunt ends is isolated on a 0.8% agarose gel in Tris-acetate buffer pH 8.2. The DNA is electroeluted and ethanol precipitated. This fragment contains the u-PA G-domain and the u-PA B-chain connected to the vector molecule.

10 μg of plasmid p31/PH05-TPA18 (European patent application No. 143,081) are digested with AluI. A 447 bp AluI fragment containing the whole K2 domain of t-PA is isolated on a 1.5% agarose gel in Tris-borate-EDTA buffer pH 8.3. The DNA fragment is electroeluted and ethanol precipitated.

0.2 pmoles of the 447 bp fragment and 0.1 pmoles of the 4.2 kb fragment are ligated. Aliquots of the ligation mixture are used to transform competent E. coli BH101 cells. Transformed cells are selected on LB agar plates with 100 mg/l ampicillin. DNA is prepared from ampicillin-resistant cells and analysed by EcoRI and ScaI digests. A single clone showing a 551 bp EcoRI fragment and a 403 bp ScaI fragment has the AluI fragment inserted in the correct orientation. This clone is referred to as pCS16/UK$_2$UPA$^B$.

EXAMPLE 6.13

Cloning of Primary Hybrid DNA Constructs in M13mp18

A) Cloning of a pJDB207/PH05-l-TPA$^A$UPA$^B$ BamHI Fragment in M13mp18

1.5 μg of pJDB201/PH05-l-TPA$^A$UPA$^B$ (cf. Example 6.9) obtained from a quick DNA preparation is digested with 9 U of BamHI (Boehringer) in 20 μl of 10 mM Tris.HCl pH 7.5, 6 mM MgCl$_2$, 100 mM NaCl, 6 mM mercaptoethanol at 37° C. for one hour. After adding 1 μl of RNase (Serva, 1 mg/ml), incubating for 15 min at 37° C. and phenolization, the 2.5 kb insert is isolated on a 0.8% preparative agarose gel. The DNA is extracted by electroelution and precipitated.

1 μg of M13mp18 (RF) is cut with BamHI, treated with calf intestinal alkaline phosphatase and the 7.3 kb vector fragment is isolated on a 0.7% preparative agarose gel. The DNA is electroeluted and precipitated.

100 pmoles of M13mp BamHI cut vector and 200 pmoles of the BamHI TPA$^A$UPA$^B$ insert are ligated in 10 μl of 50 mM Tris. HCL pH 7.5, 10 mM MgCl$_2$, 10 mM DTT, 2 mM ATP, 0.5 μg gelatin with 400 U of T$_4$ DNA ligase for 7 hours at 15° C. After incubation at 65° C. for 10 min, 5 μl of this ligation mixture is used for transformation of E. coli JM101 competent cells according to the manual "M13 Cloning and sequencing handbook" published by Amersham. 36 colourless plaques are picked, and single-stranded and replicative form (RF) DNA are prepared. On analysis of RF-DNA all clones show the correct size inserts after digestion with BamHI. Correct size fragments after digestion with EcoRI and PstI indicate that the DNA inserts in all clones are in the wrong orientation (single-stranded template DNA is the non-coding strand). One of these clones is referred to as mp18/BamHI/TPA$^A$UPA$^B$ and is used for deletion mutagenesis.

B. Cloning of a pCS16/UPA$^A$TPA$^B$ KpnI-HindIII Fragment in M13mp18

15 μg of pCS16/UPA$^A$TPA$^B$ (cf. Example 6.10) obtained from a quick DNA preparation is digested with 12 U of KpnI in 20 μl of 10 mM Tris.HCl pH 7.5, 6 mM MgCl$_2$, 6 mM mercaptoethanol at 37° C. for one hour. After adding 1 μl of 1M NaCl, DNA is digested with 12 U of HindIII at 37° C. for one hour. A 1.5 kb fragment is isolated on a 0.8% preparative agarose gel. The DNA is extracted by electroelution and precipitated.

0.5 μg of M13amp18 (RF) is digested with KpnI and HindIII. The 7.3 kb vector fragment is isolated on a 0.7% preparative agarose gel. The DNA is electroeluted and precipitated.

100 fmoles of M13mp18 KpnI-HindIII cut vector and 200 fmoles of KpnI-HindIII insert are ligated in 10 μl of 50 mM Tris.HCl pH 7.5, 10 mM MgCl$_2$, 10 mM DTT, 2 mM ATP, 0.5 μg gelatin with 400 U of T$_4$ DNA ligase for 7 hours at 15° C. The reaction is stopped by incubation at 65° C. for 10 min. 5 μl of this ligation mixture is used for transformation of E. coli JM101 competent cells. Ten colourless plaques are picked, and single-stranded and replicative form (RF) DNA are prepared. On analysis of RF-DNA, all clones show correct size inserts and correct size fragments. One of these clones is referred to as mp18/KpnI-HindIII/UPA$^A$TPA$^B$ and is used for deletion mutagenesis.

C. Cloning of a pCS16/UK$_2$TPA$^B$ KpnI-HindIII Fragment in M13mp18

1.5 μg of pCS16/UK$_2$TPA$^B$ (cf. Example 6.11) obtained from a quick DNA preparation is digested with 12 U of KpnI (Boehringer) in 20 μl of 10 mM Tris-HCl pH 7.5 6 mM MgCl$_2$, 6 mM mercaptoethanol at 37° C. for one hour. After adding 1 μl of 1M NaCl, DNA is digested with 12 U of HindIII at 37° C. for one hour. A 1.5 kb fragment is isolated on a 0.8% preparative agarose gel. The DNA is extracted by electroelution and precipitated.

0.5 μg of M13mp18 (RF) is digested with Kpn 1 and HindIII. The 7.3 vector fragment is isolated on a 0.7% preparative agarose gel. The DNA is electroeluted and precipitated.

100 fmoles of M13mp18 KpnI-HindIII cut vector and 200 fmoles of KpnI-HindIII insert are ligated in 10 μl of 50 mM Tris.HCl pH 7.5, 10 mM MgCl₂, 10 mM DTT, 2 mM ATP, μg gelatin with 400 U of T₄ DNA ligase for 7 hours at 15° C. The reaction is stopped by incubation at 65° C. for 10 min. 5 μl of this ligation mixture is used for transformation of E. coli JM101 competent cells. Seven colourless plaques are picked, and single stranded and replicative form (RF) DNA are prepared. On analysis of RF-DNA, all clones shown correct size inserts and correct size fragments. One of these clones is referred to as mp18/KnpI-HindIII/UK₂TPA$^B$ and is used for deletion mutagenesis.

D. Cloning of a pCS16/UK₂UPA$^B$ KPn 1-HindIII Fragment in M13mp18

1.5 μg of PCS16/UK₂UPA$^B$ (cf. Example 6.12) obtained from a quick DNA preparation is digested with 12 U of KpnI in 20 μl of 10 mM Tris.HCl pH 7.5, 6 mM MgCl₂, 6 mM mercaptoethanol at 37° C. for one hour. After adding 1 μl of 1M NaCl, the DNA is digested with 12 U of HindIII at 37° C. for one hour. A 1.7 kb fragment is isolated on a 0.8% preparative agarose gel. The DNA is extracted by electroelution and precipitated.

0.5 μg of M13mp18 (RF) is digested with KpnI and HindIII. The 7.3 kb vector fragment is isolated on a 0.7% preparative agarose gel. The DNA is electroeluted and precipitated.

100 fmoles of M13mp18 KpnI-HindIII cut vector and 200 fmoles of KpnI-HindIII insert are ligated in 10 μl of 50 mM Tris.HCl pH 7.5, 10 mM MgCl₂, 10 mM DTT, 2 mM ATP. 0.5 μg gelatin with 400 U of T₄ DNA ligase for 7 hours at 15° C. The reaction is stopped by incubation at 65° C. for 10 min. 5 μl of this ligation mixture is used for transformation of E. coli JM101 competent cells. Ten colourless plaques are picked, and single-stranded and replicative form (RF) DNA are prepared. On analysis of RF-DNA, all clones show correct size inserts and correct size fragments. One of these clones is referred to as mp18/KpnI-HindIII/UK₂UPA$^B$ and is used for deletion mutagenesis.

EXAMPLE 6.14

Deletion Mutagenesis of Primary Hybrid DNA Constructs

A) General Protocol for Deletion Mutagenesis a) Phosphorylation of Mutagenic Primer For mutagenesis 200 pmoles of the mutagenic primer are phosphorylated in 20 μl of 50 mM Tris-HCl pH 7.5, 10 mM MgCl₂, 5 mM DTT, 0.1 mM spermidine, 0.1 mM EDTA containing 1 μl of 10 mM ATP using 8 U of T₄ polynucleotide kinase (Boehringer, 8 U/μl). After incubation at 37° C. for one hour, the reaction is stopped by heating at 65° C. for 10 min.

For hybridization screening, 20 pmoles of mutagenic primer are phosphorylated as above using 30 μCi γ³²P-ATP (3000 ci/mmole; Amersham International) at the only source of ATP. The primer is diluted with 3.5 ml 6×SSc and used directly as a probe.

b) Annealing of Mutagenic Primer and Universal Sequencing Primer to Single-Stranded Template 0.2 pmole of single-stranded template is incubated with 20 pmoles of phosphorylated mutagenic oligodeoxyribonucleotide primer (10 pmole/μl) and 10 pmoles of universal M13 sequencing primer in 10 μl of 20 mM Tris.HCl pH 7.5, 10 mM MgCl₂, 50 mM NaCl, 1 mM DTT at 95° C. for 5 min. The solution is allowed slowly to cool to room temperature over a period of 30 min.

c) Extension-Ligation Reaction

To the above annealed mixture is added 10 μl of enzyme-dNTP (dATP, dGTP, dTTP, dCTP) solution containing 1 μl of buffer [0.2M Tris.HCl pH 7.5, 0.1 MgCl₂, 0.1M DTT], 4 μl 2.5 mM dNTP mixture, 1 μl 10 mM ATP, 0.5 μl T₄ DNA ligase (Biolabs, 400 U/μl), 0.67 μl of Klenow DNA polymerase (BRL, 2.99 U/μl). The mixture is incubated at 15° C. for one hour and then incubated at 8°–9° C. for 16 hours. The reaction is stopped by incubating at 65° C. for 10 min.

d) Transformation of Ligation Mixture

The ligation mixture is diluted 1:20 and 1:200 with TE, 1 μl and 5 μl of each of these diluted solutions are used to transform 0.2 ml of a repair-minus strain of E. coli BMH 71-18mutS [BMH71-18(Δ(lac-proAB), thi, supE, F'laci$^q$, ZΔM15, proA+B+] competent cells. Construction of E. coli BMH71-18mutS (BMH71-18, mut S215::Tnio) is described by Kramer et al. [Cell 38, 879–887 (1984)]. After transfection, lawn cells are provided by repair+strain of E. coli JM101 in order to minimize the exposure of the phage to the mutator phenotype of the repair-minus strains [P. Carter, H. Bedouelle and G. Winter, Nucl. Acids Res. 13, 4431–4443 (1985)].

e) Screening of Phages 100 plaques resulting from the transfected DNA are tooth picked on to YT plates and grown up as colonies of infected bacteria for 15–18 hours. Colony blotting was adapted from Grunstein and Hogness [Proc. Natl. Acad. Sci. USA 72, 3961–3965 (1985)]. A nitrocellulose filter (Millipore S. A., Cat. No. HAWP 090, pore size 0.45 μm) is placed on the colony plate for 10 min at room temperature. Filters are denatured with 0.5N NaOH, neutralized with 1M Tris.HCl pH 7.5 and then treated with a high-salt solution (0.5M Tris.HCl pH 7.5+1.5M NaCl). The filters are baked in vacuo for 30 minutes at 80° C., prehybridized in 100 ml of 10×Denhardt's solution (D. T. Denhardt, Biochem. Biophys. Res. Commun. 23, 641–646), 6×SSC and 0.2% SDS in a sealable plastic bag for 15 minutes.

For hybridization screening, prehybridized filters are washed in 50 ml of 6×SSC for 1 minute and then hybridized in 3.5 ml of probe containing ³²P-labelled mutagenic primer for 30 minutes. Hybridized filters are washed three times in 100 ml 6×SSC at room temperature for a total of 2 minutes and then autoradiographed. Good discrimination between wild-type and mutant phages are obtained by a brief wash (5 min) at 60° C. in 100 ml 0.1×SSC+0.1% SDS.

f) Confirmation of Deletion Mutation in Positive Clones Obtained from Hybridization These phages from the positive clones are tooth picked into 1 ml 2×YT, heated at 70° C. for 20 minutes to kill the bacteria, and then 100 μl of this phage suspension is inoculated into 1.5 ml of a freshly growing E. coli JM101 culture (OD₆₀₀~0.45). The cultures are vigorously shaken (300 rpm) at 37° C. for 4 hours. Phage-stock and replicative form DNA from the positive clones are prepared [J. Messing, Methods in Enzymology, 101, 21–78 1983)]. DNA from the mutants (after deletion mutagenesis) is analysed with suitable restriction enzymes and compared with the restriction fragments of wild type (before deletion mutagenesis) DNA. After confirmation by restriction analysis, DNA from one correct mutant is plaque purified. Mutations are further verified by restriction analysis and sequencing using the chain-terminator method [F. Sanger, S. Niclen and A. R. Coulson, Proc. Natl. Acad. Sci. USA 74, 5463–5467 (1977)].

B) Deletion Mutagenesis on mp18/BamHl/-TPA$^S$UPA$^B$ (see FIG. 30)

Deletion mutagenesis is carried out as described in the general protocol. Positive clones obtained from hybridization are confirmed by restriction analysis. 333 bp are removed by deletion mutagenesis from the BamHl fragment. Restriction analysis with BamHl confirms the 2150 bp fragment. Further restriction analysis with EcoRl yields 660, 416, 287, 230 bp fragments on the mutants instead of 660, 472, 416 and 287 fragments seen in the wild type. Analysis with Pstl shows two fragments, 611 and 414 bp in size for the mutants. Wild type DNA shows three fragments of 622, 611 and 414 bps. One mutant clone having the correct structure is referred to as mp18/BanHl/MOTPA$^A$UPA$^B$.

The DNA sequence at the junction between the t-PA A chain and u-PA B chain is verified by the chain terminator sequencing method having a sequencing primer of the sequence

5'CAGAGCCCCCCCGGTGC 3'.

This primer is complementary to the coding strand of u-PA (682–666).

C) Deletion Mutagenesis on mp18/Kpnl-Hindll-l/UPA$^A$TPA$^B$ (see FIG. 31)

Deletion mutagenesis is carried out as described in the general protocol. Prositive clones obtained from hybridization are confirmed by restriction analysis with Pstl. In the mutants a 467 bp band is observed compared to the wild type which yields a 544 bp fragment. One mutant clone having the correct structure is referred to as mp18/Kpnl-Hindlll/MOUPA$^A$TPA$^B$. The delection is verified by the chain-terminator sequencing method using a sequencing primer of the sequence

5'CAAAGATGGCAGCCTGC 3'

This primer is complementary to the coding strand of t-PA (1062–1046).

D) Deletion Mutagenesis on mp18/Knpl-Hindll-l/UK$_2$TPA$^B$ (see FIG. 32)

Deletion mutagenesis is carried out as described in the general protocol. Positive clones obtained from hybridization are confirmed by restriction analysis with Kpnl-Hindlll, Eco Rl and Pstl. The fragments obtained are

| KpnI-HindIII | | EcoRI | | PstI | |
|---|---|---|---|---|---|
| wild type | mutant | wild type | mutant | wild type | mutant |
| 1475 bp | 1284 bp | 542 bp | 351 bp | 622 bp | no 622 bp band |
| | | 472 bp | 472 bp | | |

Correct size insert and correct size fragments are observed for mutants. One mutant clone having the correct structure is referred to as mp18/Kpnl-Hindlll-/MOUK$_2$TPA$^B$. The deletion is verified by the chain-terminator sequencing method using a sequencing primer of the sequence

5'CCCAGTGCCTGG-
  GCACTGGGGTTGTGCTGTG 3'.

This primer is complementary to the coding strand of t-PA (853–821).

E) Deletion Mutagenesis on mp18/Kpnl-Hindll-l/UK$_2$UPA$^B$ (see FIG. 33)

Two separate deletion mutations are involved in the construction of UK$_2$UPA$^B$. First deletion mutagenesis is carried out as described in the general protocol. Positive clones obtained from hybridization are confirmed by restriction analysis with EcoRl. In the mutants 549, 416, 351 bp bands are observed compared to the wild type which yields 549, 452 and 416 bp fragments. One mutant clone having the correct structure is referred to as mp18/Kpnl-Hindlll/MOUK$_2$UPA$^B$-1. The deletion is verified by the chain-terminator sequencing method using a sequencing primer of the sequence

5'CCCAGTGCCTGG-
  GCACTGGGGTTCTGTGCTGTG 3'.

The primary is complementary to the coding strand of t-PA (853–821).

In the second step of deletion mutagenesis, a deletion is made simultaneously with the introduction of a point mutation. Deletion mutagenesis is carried out as described in the general protocol. Positive clones obtained from hybridization are confirmed by restriction analysis with EcoRl. In the mutants, 416, 351, 259 bp bands are observed compared to the wild type which yields 549, 416 and 351 bp fragments. One mutant clone having the correct structure is referred to as mp18/Kpnl-Hindlll-/MOUK$_2$UPA$^B$. The deletion is verified by the chain-terminator sequencing method using a sequence primer of the sequence

5'CAGAGCCCCCCCGGTGC 3'.

The primer is complementary to the coding strand of u-PA (682–666).

EXAMPLE 6.15

Cloning of the Hybrid t-PA/u-PA cDNA Constructs into Yeast Expression Vector pJDB207

A) Cloning of the TPA$^A$UPA$^B$ Hybrid Gene into pJDB207

RF-DNA is prepared for mp18/BamHl/MOT-PA$^A$UPA$^B$ by the quick DNA isolation procedure [D. S. Holmes and M. Quingley, Anal. Biochem. 114, 192–197 (1981)].

RF-DNA (~1.5 μg) is digested with 9 U of BamHl in 20 82 1 of 10 mM Tris.HCl pH 7.5 m, 6 mM MgCl$_2$, 100 mM NaCl, 6 mM mercaptoethanol for one hour at 37° C. After adding 1 μl of RNase (1 mg/ml) and incubating for 10 minutes at 37° C., the 2.1 kb insert is isolated on a 0.7% preparative agarose gel. The DNA insert is extracted by electroelution and precipitated in ethanol.

1.5 μg of pJDB207/PH05-1-TPA$^A$UPA$^B$ is cut with BamHl, treated with calf intestinal alkaline phosphatase and the 6.7 kb vector is isolated. After electroelution the vector DNA is precipitated.

100 fmoles of pJDB207/PH05-1-TPA$^A$UPA$^B$ BamHl cut vector, 200 fmoles of TPA$^A$UPA$^B$ insert are ligated in 10 μl of 50 mM Tris.HCl pH 7.5; 10 mM MgCl$_2$, 10 mM DTT, 2 mM ATP, 0.5 μg gelatin with 400 U of T$_4$ DNA ligase for 8 hours at 15° C. The reaction is stopped by incubation at 65° C. for 10 minutes. 5 μl of this ligation mixture is used for transformation of E. coli HB101 Ca$^{2+}$ cells [M. Dagert and S. D. Ehrlich, Gene 6, 23–28 (1979)]. 12 amp$^R$ colonies are picked and DNA is prepared by the quick isolation procedure. On analysis of DNA 5 clones show both correct size inserts and correct orientation. One clone is grown in 100 ml LB medium containing 100 mg/ml of ampicillin. Plasmid DNA is isolated and is referred to as pJDB207/PH05-l-MOTPA$^A$UPA$^B$.

B) Cloning of the MOUPA$^A$TPA$^B$, MOUK$_2$TPA$^B$ and MOUK$_2$UPA$^B$ Gene Inserts into Plasmid pCS16

RF-DNA is prepared for mp18/Kpnl-Hindlll-/MOUPA$^A$TPA$^B$, mp18/Kpnl-Hindlll/MOUK$_2$TPA$^B$, mp18/Kpnl-Hindlll/MOUK$_2$UPA$^B$ by the quick DNA isolation procedure.

The three RF-DNAs (~1.5 μg) are each digested with 12 U of Kpnl and 12 U of Hindlll in 20 μl of 10 mM Tris.HCl pH 7.5, 6 mM MgCl$_2$ 6 mM mercaptoethanol for one hour at 37° C. 1 μl of 1M NaCl is added and the DNAs further digested with 12 U of Hindlll. After adding 1 μl of RNase (1 mg/ml) and incubating for 10 min at 37° C. the 1.4 kb inserts are each isolated on a 0.8% preparative agarose gel. The DNA inserts are extracted by electroelution and precipitated in ethanol.

Three μg of pCS16/UPA is digested with Kpnl and Hind lll and the 2.7 kb vector fragment is isolated. After electroelution, the vector DNA is precipitated in ethanol.

100 fmoles of CS16 Kpnl-Hindlll cut vector, 200 fmoles of Kpnl-Hindlll cut insert fragments are ligated in 10 μl of 50 mM Tris.HCl pH 7.5, 10 mM MgCl$_2$, 10 mM DTT, 2 mM ATP, 0.5 μg gelatin with 400 U of T$_4$ DNA ligase for 8 hours at 15° C. The reaction is stopped by incubation at 65° C. for transformation of E. coli HB101 CA$^{2+}$ cells.

Six amp$^R$ colonies are picked from each of the three ligations. DNA is prepared by the quick isolation procedure. On analysis of DNA with Kpnl-Hindlll correct size insert bands are observed. One clone from each of the three ligations is grown in 100 ml LB medium containing 100 μg/ml of ampicillin. Plasmid DNAs derived from mp18/Kpnl-Hindlll/MOUPA$^A$TPA$^B$, mp18/Kpnl-Hindlll/MOUK$_2$TPA$^B$ and mp18/Kpnl-Hindlll/MOUK$_2$UPA$^B$ are isolated and are referred to as pCS16/MOUPA$^A$TPA$^B$, pCS16/MOUK$_2$TPA$^B$ and pCS16/MOUK$_2$UPA$^B$, respectively.

C) Cloning of the MOUPA$^A$TPA$^B$, MOUK$_2$TPA$^B$ and MOUK$_2$UPA$^B$ Gene Inserts into pJDB207

Five μg of pJDB207/PH05-l-UPA is digested with 15 U of Scal and 15 U of Xhol (Boehringer) in 50 μl of 10 mM Tris.HCl pH 7.5, 6 mM MgCl$_2$, 150 mM NaCl, 6 mM vercaptoethanol for one hour at 37° C. After adding 1 μl of RNase (1 mg/ml), the 6.7 kb vector fragment is isolated. After electroelution, the vector DNA is precipitated.

Fifteen μg of each of pCS16/MOUPA$^A$TPA$^B$, pCS16/MOUK$_2$TPA$^B$, pCS16/MOUK$_2$UPA$^B$ are incubated at 37° C. for one hour with 30 U of Khol in 200 of 10 mM Tris.HCl pH 8, 6 mM MgCl$_2$, 150 mM NaCl, 6 mM mercaptoethanol, extracted with an equal volume of phenol-chloroform and precipitated in ethanol. The precipitated Xhol cut pCS16/MOUPA$^A$TPA$^B$, pCS16/MOUK$_2$TPA$^B$ and pCS16/MOUK$_2$UPA$^B$ DNAs are each resuspended in 150 μl of 10 mM Tris.HCl pH 7.5, 6 mM MgCl$_2$, 150 mM NaCl, 6 mM mercaptoethanol, 1.5 μg ethidium bromide incubated at 37° C. for 40 minutes with 12 U of Scal (partial digest), and extracted with an equal volume of phenol, followed by an equal volume of chloroform-isoamyl alcohol (50:1). Then 1.2 kb fragments are each isolated on a 1% preparative agarose gel. The DNAs are extracted by electroelution and precipitated.

100 fmoles of pJDB207/PH05-l-UPA Scal-Xhol cut vector and 200 fmoles of Xho-Scal cut pCS16/MOUPA$^A$TPA$^B$, pCS16/MOUK$_2$TPA$^B$ or pCS16/MOUK$_2$UPA$^B$1.2 kb inserts, respectively, are ligated in 10 μg of 50 mM Tris.HCl pH 7.5 10 mM MgCl$_2$, 10 mM DTT, 2 mM ATP, 0.5 μg gelatin with 400 U of T$_4$ DNA ligase for 16 hours at 15° C. The reaction is stopped by incubation at 65° C. for 10 minutes. 5 μl of this ligation mixture is used for transformation of E. coli HB101 Ca$^{2+}$ cells.

Six amp$^R$ colonies are picked from each of the three ligations. DNA is prepared by the quick isolation procedures. Restriction analysis of DNAs show correct size insert bands. One clone from each of the three ligations is grown in 100 ml LB medium containing 100 μg/ml of ampicillin. Plasmid DNAs derived from pCS16/MOUPA$^S$TPA$^B$, pCS16/MOUK$_2$TPA$^B$, pCS16/MOUK$_2$UPA$^B$ are referred to as pJDB207/PH05-l-MOUPA$^A$TPA$^B$, pJDB207/PH05-l-MOUK$_2$TPA$^B$ and pJDB207/PH05-l-MOUK$_2$UPA$^B$, respectively.

EXAMPLE 6.16

Transformation of Saccharomyces cerevisiae GRF18 and Preparation of Yeast and Cell Extracts The plasmids pJDB207/PH05-l-MOTPA$^A$UPA$^B$, pJDB207/PH05-l-MOUPA$^A$TPA$^B$, pJDB207/PH05-l-MOUK$_2$TPA and pJDB207/PH05-l-MOUK$_2$UPA$^B$ are each introduced into Saccharomyces cerevisiae strain CRF18 using the transformation protocol described by Hinnen et al. [Proc. Natl. Acad. Sci. USA 75, 1929 (1978)]. Five μg each of plasmid DNA are added to 100 μl of a spheroplast suspension and the mixture is treated with polyethylene glycol. The spectroplasts are mixed with 10 ml regeneration agar and plated onto yeast minimal medium plates without leucine. After incubation for 3 days at 30° C. about 200 transformed cells are obtained.

One colony from each of the yeast transformations is picked.

The different colonies are referred to as

Saccharomyces cerevisiae GRF18/pJDB207/PH05-l-MOTPA$^A$UPA$^B$

Saccharomyces cerevisiae GRF18/pJDB207/PH05-l-MOUPA$^A$TPA$^B$

Saccharomyces cerevisiae GRF18/pjDB207/PH05-l-MOUK$_2$TPA$^B$

Saccharomyces cerevisiae GRF18/pJDB207/PH05-l-MOUK$_2$UPA$^B$

Yeast cells are grown at 30° C. in 20 ml of HE-17 medium (8.5 g Yeast Nitrogen Base (Difco), 10 g L-asparagine (Sigma), 1 g L-histidine (Sigma), 40 ml 50% glucose per 1 liter solution) in a 50 ml Erlenmeyer flask with shaking for 24 hours until a density of 8–10×10$^7$ cells/ml is reached. The cells are centrifuged, resuspended in 10 ml 0.9% NaCl. Two ml of the resuspended cells are used to inoculate 50 ml low-P$_1$ minimal medium (as described in European Patent Application No. 143081) to which 10 g/l L-asparagine (Sigma), and 10 g/l L-histidine (Sigma), are added in 250 ml Erlenmeyer flasks. Incubation is at 30° C. at 250 rpm.

Cells from 10 ml of low $P_i$ minimal medium are collected after 48 hours by centrifugation at 3000 rpm for 10 minutes in Falcon 2070 tubes. The cells are washed one with 10 ml low $P_i$ medium and centrifuged. The cell pellet is suspended in lysis buffer [66 mM potassium phosphate pH 7.4, 4 mM Zwittergent (Calbiochem.) . To the cell suspension are added 8 g of glass beads (0.5–0.75 mm in diameter) and a small glass rod and the suspension is shaken on a Vortex Mixer (scientific Instruments Inc., USA) at fullspeed for 4×2 min with intervals of 2 min on ice. More than 90% of the cells are broken by this procedure. Cell debris and glass beads are sedimented by centrifugation for 5 min at 3000 rpm at 4° C. The supernatant is used for the determination of PA activity and for the purification and isolation of PA.

EXAMPLE 6.17

Insertion of Hybrid PA Coding Sequences into Mammalian Cell Expression Vector

A) Insertion of a UPA$^A$TPA$^B$ 'Perfect' Hybrid Coding Sequence

RF DNA of mp18/Kpnl-Hindlll/MOUPA$^A$TPA$^B$ is cut at the Smal site located just upstream of the beginning of the coding sequence and ligated to a Scal linker (CGAGCTCG). Subsequently, the plasmid is cut with Sacl, which cuts at the position of the ligated linkers and at the natural Sacl site in the t-PA-derived portion of the hybrid PA coding sequence. The smaller of the two resulting fragments is purified via an agarose gel and ligated to Sacl-cut pCGA44 (see Example 6.4) transformed into E. coli HB101 and DNA from candidate clones is tested with EcoRl. A clone with the expected restriction pattern is referred to as pCGC1/UPA$^A$T-PA$^B$.

B) Insertion of UK$_2$TPA$^B$ Hybrid Coding Sequence

RF DNA of mp18/Kpnl-Hindlll/MOUK$_2$TPA$^B$ is cut at the Smal site located just upstream of the begin of the coding sequence and ligated to Sacl as above. After cutting with Sacl the resulting small fragment is cloned into Sacl-cut pCGA44 as described above and a clone with the expected restriction pattern is referred to as pCGC$_2$/UK$_2$TPA$^B$.

C) Insertion of a UK$_2$UPA$^B$ Hybrid Coding Sequence

RF DNA of mp18/Kpnl-Hindlll/MOUK$_2$UPA$^B$ is cut at the Smal site upstream of the u-PA coding sequence and at the Xhol site downstream of the coding sequence (in the vector DNA). The sticky end of the DNA fragment is filled in using E. coli DNA polymerase 1 (cf. Example 6.5D). Sacl linkers are ligated onto the blunt ends, the DNA is cut with Sacl, the smaller of the two resulting fragments is purified via an agarose gel and clone into Sacl-cut pCGA44. A clone with the expected EcoRl restriction pattern is referred to as pCGC3/UK$_2$UPA$^B$.

D) Insertion of a TPA$^A$UPA$^B$ 'Perfect' Coding Sequence

Step 1: RF DNA of mp18/BamHl/MOTPA$^A$UPA$^B$ is cut with BamHl and the smaller (~2.1 kb) fragment is cloned into BamHl cut pJDB207/PH05-1-TPA$^A$UPA$^B$ (cf. Example 6.9) vector. Correct orientation i chosen by digestion with Hindlll and one correct plasmid is termed pJDB207/PH05-1-MOTPA$^A$UPA$^B$.

Step 2: A ~600 bp Sacl-Narl fragment from ptNC.UC (cf. Example 6.3) and a ~1350 bp Narl-Xhol fragment from pJDB207/PH05-1-TPA$^A$UPA$^B$ is isolated and cloned into Sacl-Xhol cut pCS16 (cf. Example 6.7) vector. The ~1.9 kb insert is confirmed by digestion with Sacl-Xhol and EcoRl. One correct plasmid is termed pCS16/MOTPA$^A$UPA$^B$.

Step 3: Plasmid pCS16/MOTPA$^A$UPA$^B$ is cut at the Xhol site located downstream of the u-PA coding sequence and the sticky ends filled in using E. coli DNA polymerase 1. Sacl linkers are ligated onto the blunt ends and the DNA is cut with Sacl. The smaller of the two fragments is purified via an agarose gel and cloned into Sacl-cut pBR4a (cf. Example 6.5) vector fragment. Correct orientation and correct size inserts are confirmed by digestion with BamHl and Sacl, respectively. One correct plasmid is designated pCGC4a/TPA$^A$UPA$^B$.

EXAMPLE 6.18

Construction of Further Hybrid PA Coding Sequences and Insertion thereof into Mammalian Cell Expression Vector A) Cloning of a pCGC4a/TPA$^A$UPA$^B$ Fragment in M13mp18

3 μg of pCGC4a/TPA$^A$UPA$^B$ (cf. Example 6.17) is digested with 12 U of Sacl (Boehringer) in 20 μl of 10 mM Tris-HCl pH 7.5, 6 mM MgCl$_2$ 6 mM mercaptoethanol at 37° C. for one hour. A ~1.9 kb fragment is isolated on a 0.7% preparative agarose gel. The DNA is extracted by electroelution and precipitated.

0.5 μg of M13mp18 (RF) is digested with Sacl. The 7.3 kb vector fragment is isolated on a 0.7% preparative agarose gel. The DNA is electroeluted and precipitated.

100 fmoles of M13mp18 Sacl cut vector and 200 fmoles of Sacl insert are ligated in 10 μl of 50 mM Tris-HCl pH 7.5, 10 mM MgCl$_2$, 10 mM DTT, 2 mM ATP, 0.5 μg gelatin with 400 U of T$_4$ DNA ligase for 7 hours at 15° C. The reaction is stopped by incubation at 65° C. for 10 min. 5 μl of this ligation mixture is used for transformation of E. coli JM101 competent cells. Six colourless plaques are picked, and single stranded and replicative form (RF) DNA are prepared. On analysis of RF-DNA, four clones show correct size inserts and correct orientation. One of these clones is referred to as mp18/Sacl-TPA$^A$UPA$^B$ (BC).

B) Cloning of a pBR4a Sacl Fragment in M13mp18

A pBR4a (cf. Example 6.5) Sacl fragment is cloned in M13mp18. One of the clones which has a correct size insert and a correct orientation is referred to as mp118/Sacl/TPA$^A$UPA$^B$(BR).

C) Deletion Mutagenesis on TPA-UPA Hybrid Constructs

1) Construction of K$_2$UPA$^B$ (BC) [i.e. tPA(1-3)-tPA(176-275)-uPA(159-411)]

Deletion mutagenesis is carried out as described in the general protocol (cf. Example 6.14) on mp18/Sacl/-TPA$^A$UPA$^B$(BC). Positive clones obtained from hybridization are confirmed by restriction analysis with Sacl. In the mutants a ~1380 bp band is observed compared to the wild type which yields a ~1900 bp fragment. Mutants are further confirmed by EcoRl digest. One mutant clone having the correct structure is referred to as mp18/Sacl/K$_2$UPA$^B$(BC). The deletion is verified by the chain terminator sequencing method using a sequencing primer of the sequence

```
5'CCCAGTGCCTGG-
   GCATTGGGTTCTGTGCTGTG 3'
```

This primer is complementary of the coding strand of t-PA(853-821) with a mismatch at position 838 (t-PA).

2) Construction of FUPA$^B$(BC) [ie. tPA(262–275)-uPA(159–411)]

Deletion mutagenesis is carried out as described in the general protocol (cf. Example 6.14) on mp18/SacI/-TPA$^A$UPA$^B$(BC). Positive cloned obtained from hybridization are confirmed by restriction analysis with SacI. In the mutants a ~1200 bp band is observed compared to the wild type which yields a ~1900 bp fragment. Mutants are further confirmed by EcoRl digest. One mutant clone having the correct structure is referred to as mp18/SacI/FUPA$^B$(BC). The deletion is verified by the chain terminator sequencing method using a sequencing primer of the sequence

5′CAGAGCCCCCCCGGTGC 3′.

This primer is complementary to the coding strand of u-PA(666–682).

3) Construction of FK$_2$UPA$^B$(BC) [ie. tPA(1–49)-tPA(176–275)-uPA(159–411)]

Deletion mutagenesis is carried out as described in the general protocol (Cf. Example 6.14) on mp18/SacI/TPA$^A$UPA$^B$(BC). Positive clones obtained from hybridization are confirmed by restriction analysis with SacI. In the mutants a ~1470 bp band is observed compared to the wild type which yields a ~1900 bp fragment. Mutants are further confirmed by EcoRl digest. One mutant clone having the correct structure is referred to as mp18/SacI/KF$_2$UPA$^B$(BC). The deletion is verified by the chain terminator sequencing method using a sequencing primer of the sequence

5′CCCAGTGCCTGG-GCATTGGGGTTCTGTGCTGTG 3′.

This primer is complementary to the coding strand of t-PA9′53-821) with a mismatch at position 838 (t-PA).

4) Construction of FGK$_2$UPA$^A$(BC) [ie. tPA(1–86)-t(PA(176–275(-uPA(159–411)]

Deletion mutagenesis is carried out as described in the general protocol (cf. Example 6.14) on mp18/SacI/-TPA$^A$UPA$^B$(BC). Positive clones obtained from hybridization are confirmed by restriction analysis with SacI. In the mutants a ~1580 bp band is observed compared to the wild type with yields a ~1900 bp fragment. Mutant are further confirmed by EcoRl digest. One mutant clone having the correct structure is referred to as mp18/SacI/FGK$_1$UPA$^B$(BC). The deletion is verified by the chain terminator sequencing method using a sequencing primer of the sequence

5′CCCAGTGCCTGG-GCATTGGGGTTCTGTGCTGTG 3′.

This primer is complementary to the coding strand of t-PA(853–821) with a mismatch at position 838 (t-PA).

5) Similar deletion mutagenesis protocols are used to generate

K$_2$UPA$^B$(BR)[tPA(1-3)-tPA(176-262)-uPA(132-411)]
FUPA$^B$(BR)[tPA(1-49)-uPA(134-411)]
FK$_2$UPA$^B$(BR)[tPA(1-49)-tPA(176-262)-uPA(1-32-411)] and
FGK$_2$UPA$^B$(BR)[tPA(176-262)-uPA(132-411)].

D) Insertion of Hybrid PA Coding Sequences into Mammalian Cell Expression Vector 1. Insertion of FUPA$^B$(BC), K$_2$UPA$^B$(BC), FK$_2$UPA$^B$(BC) and FGK$_2$UPA$^B$(BC).

RF DNA from mp18/SacI/K$_2$UPA$^B$(BC), mp18/SacI-FUPA$^B$(BC), mp18/SacI/FK$_2$UPA$^B$(BC) and mp18/SacI/FGK$_2$UPA$^B$(BC) are each cut with SacI. The smaller of the two resulting fragments is isolated and is ligated to SacI cut pBR4a (cf. Example 5) vector fragment, transferred into E. coli HB101 and correct orientation and correct size inserts are confirmed by digestion with BamHI and SacI, respectively. The resultin plasmids are designated pCGC5/K$_2$UPA$^B$, pCGC6/FUPA$^B$, pCGC7/K$_2$UPA$^B$ and pCGC8/FGK$_2$UPA$^B$, respectively.

2. Similarly, K$_2$UPA$^B$(BR), FUPA$^B$(BR), FK$_2$UPA$^B$(BR) and FGK$_2$UPA$^B$(BR) DNAs (see above) are each inserted into pBR4a. The obtained plasmids are designated pBR5, pBR6, pBR7, and pBR8, respectively.

EXAMPLE 6.19

Mammalian Expression Vectors Comprising the DHFR Gene

Plasmid pSV2dhfr (ATCC 37145) is a plasmid allowing selection of transformate of DHFR-containing cells by selection using the antifolate drug methotrexate or selection of DHFR+ transformants of DHFR CHO cells [DUKXBl cells; G. Urlaub. Proc. Natl. Acad. Sci. U.S.A. 77, 4216–4220 (1980)]. Into the single BamHI site of this plasmid can be cloned the BamHI fragment of pCGA28 containing the modular t-PA gene. Plasmids containing either of the two possible orientations are designated pCGA700a/tPA. Both can be used to express t-PA in tissue culture cells but preferred is the pCGA700a/tPA, in which transcription of the t-PA gene is in the same direction as that of the DHFR gene, as this orientation frequently leads to slightly higher expression levels than with plasmids that are convergently transcribed.

In an analogous fashion the modular genes encoding hybrid plasminogen activators (below) from plasmids pBR1/tPA, pBR2a/UPA$^A$TPA$^B$, pCGC1/UPA$^A$TPA$^B$, and pCGC2/UK$_2$TPA$^B$ can be combined as BamHI fragments with the DHFR gene of pCGA700a/tPA to form plasmids pCGA701a/tPA, pCGA702a/UPA$^A$TPA$^B$, PCGA705a/UPA$^A$TPA$^B$ and pCGA707a/UK$_2$TPA$^B$, respectively, in which the modular plasminogen activator gene is transcribed in the same direction as the DHFR gene, and pCGA701b.-tPA, pCGA702b/UPA$^A$TPA$^B$, pCGA705b.UPA$^A$TPA$^B$, pCGA707b/KK$_2$TPA$^B$ in which both genes are transcribed in opposite directions. Due to the presence of a BamHI sequence in the portion encoding the u-PA B-chain the modular plasminogen activator gene can only be isolated by a partial cut (2 of the 3 BamHI sites) of the neo$^R$ plasmid followed by isolation of the appropriate fragment (cf. figures) by agarose gel electrophoresis. Thus, from pBR3a/uPA, pBR4a/TPA$^A$UPA$^B$, pBR5/K$_2$UPA$^B$, pBR6/FUPA$^B$, pBR7/FK$_2$UPA$^B$, pBR8/FGK$_2$UPA$^B$, pCGC3/UK$_2$UPA$^B$, pCGC4a/TPA$^A$UPA$^B$, pCGC5/K$_2$UPA$^B$, pCGC6/FUPA$^B$, pCGC7/FK$_2$UPA$^B$, and pCGC8/FGK$_2$UPA$^B$ can be constructed pCGA703a/uPA, pCGC704a/TPA$^A$UPA$^B$, pCGA705a/K$_2$UPA$^B$, pCGC708a/FUPA$^B$, pCGC706a/FK$_2$UPA$^B$, pCGC707a/FGK$_2$UPA$^B$, pCGC709a/UK$_2$UPA$^B$, pCGC711a/TPA$^A$UPA$^B$, pCGC712a/K$_2$UPA$^B$, pCGA713a/FUPA$^B$, pCGA714a/FK$_2$UPA$^B$ and pCGA715a/FGK$_2$UPA$^B$, respectively, in which the plasminogen activator genes all are transcribed in the same direction as the DHFR gene, and further pcGA703b/uPA, pCGA704b/TPA$^A$UPA$^B$, pCGA708b/FUPA$^B$, pCGA705b/K2UPA$^B$, pCGA706b/FK2UPA$^B$, pCGA707b/FGK2UPA$^B$, pCGA709b/UK2UPA$^B$, pCGA711b/TPA$^4$UPA$^B$, pCGA712b/K2UPA$^B$, pCGA713b/FUPA$^B$, pCGA714b/FK2UPA$^B$ and pCGA7156/FGK2UPA$^B$, in which both genes are transcribed inconvergently.

EXAMPLE 6.20

Production of Hybrid Plasminogen Activators by Transformed Mammalian Cells

A) Maintenance and DNA Transfection of Tissue Culture Cells: General Procedure

DNA constructs are expressed in DUKXB1, a mutant of Chinese hamster ovary (CHO) cells lacking the enzyme dihydrofolate reductase [G. Urlaub et al., Proc. Natl. Acad. Sci. USA 77, 4216–4220 (1980)]. DUKXB1 cells are cultured in alpha-MEM medium containing nucleosides (GIBCO) supplemented with 5% fetal calf serum.

Cells are plated at a density of 10 000/cm in 6-well multiplates (3.4 cm diameter) and transformed with 4 μg DNA: DNA is dissolved at 50 μg/ml in 10 mM Tris/HCl pH 7.0 containing 0.1 mM EDTA, cooled on ice for 5 min., 0.25 volumes 1M CaCl$_2$ is added and incubated on ice for 10 min. The mixture is then mixed with an equal volume of 2×HBS (50 mM Hepes, 280 mM NaCl. 0.75 mM Na$_2$HPO$_4$, 0.75 mM NaH$_2$PO$_4$, pH 7.12) followed by another 10 min incubation on ice. Finally this DNA-Ca-phosphate coprecipitate is added to the culture medium and cells are incubated with the DNA for 16–18 h, followed by a glycerol shock, i.e. cells are rinsed with TBS (80 g/l NaCl, 3.8 g/l KCl, 1 g/l Na$_2$HPO$_4$.2H$_2$O, 0.114 g/l CaCl$_2$.2H$_2$O, 0.11 g/l MgCl$_2$.6H$_2$O, 25 mM Tris/HCl pH 7.5), incubated 1 min with 20% (v/v) glycerol in TBS, rinsed again with TBS and cultured 24 h in tissue culture medium. Cells are then trypsinized and the cells are transferred to 8 cm diameter Petri dishes. The next day the initial culture medium without selective agent is replaced by medium with 1 mg/ml geneticin. Medium is replaced every third or fourth day. Colonies can be seen around day 14. Cells from individual colonies are isolated by scraping them off with the tip of a pipetman while simultaneously sucking then into the tip filled with trypsin solution and transferring each to a wall of a 24 well multiplate supplied with medium containing geneticin. When confluent these cultures are split into the wells of a 6 well multiplate and subsequently into 8 cm diameter Petri dishes.

B) Agarose Plate Assays for Plasminogen Activators

These sensitive assays for plasminogen activators use agarose gels to which plasminogen (stock solution prepared by dissolving plasminogen Sigma A-6877 at 1 mg/ml in and dialyzing it twice against 100 volumes 50 mM Tris-HCl pH 8.0) or either casein (added as non-fat milk) or fibrin (added as fibrinogen plus thrombin) is added. The sample containing plasminogen activator is applied into holes punched into a 4 mm thick agarose layer and the gel is subsequently incubated at 37° C. The enzymatic activity is then detected in that the plasminogen activator diffuses radially away from the sample well, converts the plasminogen in the gel to plasmin which in turn digests the casein or fibrin thus producing a clear halo in the opaque gel around the sample well. The radius of the halo (measured from the rim of the sample well) is a measure for the amount of plasminogen activated. The assay does not show a linear response to the amount of plasminogen activator added.

For assay of low amounts of plasminogen activator the incubation can be prolonged to several days. The procedure and calibration of the casein assay is as described in Tang et al. [Ann. N.Y. Acad. Sci. 434, 536–540 (1984)] except that instead of 2% (w/v) Carnation non-fat milk-powder 12.5% (v/v) sterilized (UHT) fat-free milk from Migros Corp. (Switzerland) is used. When fibrin [Granelli-Piperno and Reich, J. Exp Med. 148, 223–234 (1978)] is used as a substrate 0.2 g agarose is dissolved in 15 ml 0.9% NaCl and cooled to 42° C. At this point 5 ml 0.9% NaCl containing 80 mg bovine fibrinogen (Sigma F-8630), 0.1 ml plasminogen solution (above) and 0.1 ml 100 mg/ml sodium azide at 42° C. are added. Finally, 0.2 ml bovine thrombin (Sigma T-6634, dissolved at 16.6 MIH units/ml in 0.9% NaCl) are added and the mixture is quickly poured into a Petri dish (8 cm diameter) and allowed to cool to room temperature for one hour. The resulting gel is about 4 mm thick and can be stored at 4° C. for several days or used immediately in the same manner as the casein containing gel above.

C. Production of Hybrid PA Proteins in Hamster Cells

CHO DUKXB1 cells are transformed with DNA of plasmids pBR1A, pBR1B, pBR2A, pBR2B, pBR3A, pBR3B, pBR4A, pBR5, pBR7, pBR8, pCGC1, pCGC2, pCGC3, pCGC4, pCGC5, pCGC6, pCGC7 and pCGC8, respectively, as described above (Example 6.20A). Colonies appear around day 10, colonies are picked around day 15 ad described above and two weeks later cell number has increased sufficiently to measure PA as described above. Untransformed cells and cell line transformed with pBR1B, pBR2B, pBR3B, which contain the inserted ScaI fragment in the antisense orientation do not produce detectable amount of PA.

D. Enzyme Activity in Media Conditioned by Transformed CHO Cells

Conditioned medium from plasmid transformed and control CHO cells are prepared by cultivating 200,000–500,000 cells/ml for 24 hours in Alpha-MEM with nucleosides and 5% fetal calf cerum and 0.03 ml is incubated on agarose plates containing casein or fibrin for the time period indicated below. On the fibrin plate a minimal background activity, presumably due to endogenous hamster t-PA, is detected in the DUKXB1 conditioned medium. No halo appears on casein plates if samples of hybrid protein are mixed with 3 microfilter or rabbit anti-tPA antibodies (raised against purified Bowes melanoma t-PA) or anti-urokinase antibodies (raised against Serono urokinase).

Anti t-PA antibody does not inhibit u-PA enzyme, nor does anti-urokinase antibody inhibit t-PA to a significant extent. The results are summarized in Table 1.

TABLE 1

| | Activity of different plasminogen activators | | | |
|---|---|---|---|---|
| | | | halo diameter | |
| transforming plasmid | | casein plate | | fibrin plate |
| No. | | 18 h | 36 h | 90 min | 300 min |
| 1. | pBR1a(t-PA) | 2 mm | 5 mm | 1 mm | 2 mm |
| 2. | pBR2a (UP$^4$TPA$^B$) | 0 mm | 0 mm | 0.5 mm | 1.5 mm |
| 3. | pBR3a(u-PA) | 5 mm | 10 mm | 0.5 mm | 2.5 mm |
| 4. | pBR4a (TPA$^4$UPA$^B$) | 6 mm | 11 mm | 2 mm | 3 mm |
| 5. | pBR6/K2UPA$^B$ | 3 mm | 8 mm | not determined | |
| 6. | pBR7/ FK2UPA$^B$ | 4 mm | 9 mm | 1 mm | 2 mm |
| 7. | pBR8/ | 3.5 mm | 7 mm | 0.8 mm | 2 mm |

TABLE 1-continued

Activity of different plasminogen activators

| | | halo diameter | | |
|---|---|---|---|---|
| transforming plasmid | | casein plate | | fibrin plate |
| No. | | 18 h | 36 h | 90 min | 300 min |
| 8. | pCGC1/ FGK$_2$UPA$^B$ UPA$^4$TPA$^B$ | 0 mm | 6 mm | 0.2 mm | 2 mm |
| 9. | pCGC2/ UK$_2$UPA$^B$ | 5 mm | 10 mm | 1 mm | 2.5 mm |
| 10. | pCGC3/ UK$_2$TPA$^B$ | 3.5 mm | 5 mm | 1.5 mm | 2.5 mm |
| 11. | pCGC4a/ TPA$^4$UPA$^B$ | 2.5 mm | 5 mm | 0.5 mm | 1.5 mm |
| 12. | PCGC5/ K$_2$UPA$^B$ | 6.5 mm | 12 mm | 6 mm | >10mm |
| 13. | pCGC6/ FUPA$^B$ | 2 mm | 8 mm | 0 mm | 1 mm |
| 14. | pCGC7/ FK$_2$UPA$^B$ | 2.5 mm | 5 mm | 1 mm | 2 mm |
| 15. | pCGC8/ FGK$_2$UPA$^B$ | 2.5 mm | 6 mm | 1 mm | 2 mm |
| 16. | mtPA 1 μg/ml | 3 mm | 7 mm | 1.5 mm | 3 mm |
| 17. | DUKXB1 control | 0 mm | 0 mm | 0 mm | 0.5 mm |

The media containing uK$_2$tPA, FK$_2$tuPA or K$_2$tuPA, respectively, are harvested by microfiltration (KrosFlo II, 0.2 μm hollow fibre module from Microgen, California). The cell free media are concentrated 20–50 fold by tangential flow ultrafiltration (Pellicon cassette Typ PLCG 10'000 NMWL from Millipore). This crude material is purified by affinity chromatography in each case.

6a: uK$_2$tPA uK$_2$tPA is purified by chromatography on DE-3 coupled to cyanogen bromide activated Sepharose (Pharmacia). DE-3 is a trypsin inhibitor from *Erythrina latissima* (Ch. Heussen, University of Cape Town, Thesis 1982). DE-3 Sepharose is added to the concentrated media containing uK$_2$tPA and the suspension is stirred for 45 min at 4° C. The beads are then transferred to a column and washed with 1M NaCl, 10 mM sodium phosphate pH 7.0, 0.1% Tween 80. Elutoin of the enzyme is achieved with 1.6M NH$_4$SCN in buffer consisting of 10 mM sodium phosphate pH 7.0 and 0.05% Tween 80. The effluent from the DE-3 column is applied to a G 75 medium column (Pharmacia), equilibrated with 10 mM Tris/HCl pH 8.5, 0.05% Tween 80 and developed with the equilibration buffer. Fractions containing uK$_2$tPA are pooled and applied to a Mono Q column (1 ml bed volume; Pharmacia), equilibrated with 10 mM Tris/HCl pH 8.5, 0.05% Tween 80. After washing with equilibration buffer uK$_2$tPA is eluted with a linear gradient of the equilibration buffer and buffer B composed of 1M NaCl, 10 mM Tris/HCl pH 8.5, 0.05% Tween 80.

uK$_2$tPA produced in this manner migrates as a double band of 44 kD and 42 kD molecular weight, respectively, in SDS polyacrylamide gel electrophoresis under non reducing conditions, the low molecular weight form being about 70% of the total protein. Labelling experiments with $^{125}$J-Concanavalin A indicate that the high molecular weight form is glycosylated not only in the B-chain but also in the "kringle" region.

6b: FK$_2$tuPA and K$_2$tuPA

To the concentrated media containing FK$_2$tuPA, or K$_2$tuPA, respectively, antiurokinase IgG-Sepharose is added [purified polyclonal rabbit antibody (IgG-fraction) raised against human urinary urokinase] and the suspension is stirred for 45 min at 4° C. The beads are then transferred to a column and washed with 1M NaCl, 10 mM sodium phosphate pH 7.0, 0.05% Tween 80. The respective PA is eluted with 150 mM ε-aminocaproic acid, 50 mM glycine pH 2.2, 0.05% Tween 80. The fractions containing protein are adjusted to pH 5 with 1N NaOH. The effluent from the antibody column is applied to a Mono-S column (1 ml bed volume; Pharmacia) equilibrated with 50 mM sodium phosphate pH 5.0, 0.05% Tween 80. After washing with buffer A containing equilibrium buffer at a pH of 6.0, PA is eluted with a linear gradient of buffer A and buffer B composed of 500 mM NaCl, 50 mM sodium phosphate pH 7.0, 0.05% Tween 80. By this method, FK$_2$tuPA elutes in three peaks at 35% B, 45% B and 55% B, respectively, with the 55% B peak being the major one (about 60–70% of the total amount of FK$_2$tuPA. This third peak has the expected N-terminal sequence. Labelling experiments with $^{125}$J-Concanavalin A reveal the presence of carbohydrate in the B-chain of FK$_2$tuPA whereas in the kringle region no carbohydrate is detected. FK$_2$tuPA produced in this manner migrates as a single band of about 42 kD molecular weight in SDS polyacrylamide gel under non-reducing conditions. The FK$_2$tuPA obtained has a purity of about or more than 95% as judged by SDS polyacrylamide gel electrophoresis under reducing conditions and RP-HPLC analysis. The fraction of two chain form in the final preparation is 10–15% as judged by the direct amidolytic assay.

K$_2$tuPA produced in the same manner migrates as a diffuse band of about 40 kD molecular weight in SDS polyacrylamide gel under non-reducing conditions. Labelling experiments with $^{125}$J-Concanavalin A show carbohydrate only in the B-chain of the enzyme. The K$_2$tuPA obtained has a purity of about or more than 95% as judged by SDS polyacrylamide gel electrophoresis and RP-HPLC analysis. The fraction of two chain form in the final preparation is 10–15% as judged by the direct amidolytic assay.

EXAMPLE 7

Ex Vivo Clot Lysis in Human Plasma

Human blood is directly withdrawn into 3.8% sodium citrate solution (ratio blood/citrate solution 9:1). The mixture is centrifuged at 1,000 rpm for 10 min to yield citrated plasma.

To 1 ml of citrated human plasma 20 μl of a 1M CaCl$_2$ solution in H$_2$O, 10 μl of $^{125}$J human fibrinogen (Amersham, about 300,000 cpm) and 10 μl (=0.4 U) of human thrombin (Boehringer Mannheim) are added. The mixture is quickly poured into a disposable 1 ml syringe from which the tip has been removed by a razor blade. The mixture is allowed to clot for 20 min, is then pressed out of the syringe and allowed to age for 40 min in 50 mM phosphate buffer. The worm-like clot obtained from 1 ml of plasma is cut into 4 equal pieces, each piece is put in a 10 ml tube to which 2 ml of fresh uncoagulated citrated plasma are added.

The clot lysis reaction is started by the addition of either one plasminogen activator alone or a combination of two plasminogen activators.

Reference tPA is purchased from American Diagnostica, New York or is isolated from a human melanoma cell line as disclosed in European Patent Application No. 112 122. Yeast recombinant scuPA is either obtained from American Diagnostica or is prepared according to example 5. The tPA B-chain (fused) and the hybrid plaminogen activators uK$_2$tPA, K$_2$tuPA and FK$_2$tuPA are purified according to methods given in examples 4 and 6, respectively.

Experiments are performed with blood from different blood donors. The standard amount of PA (or combinations of two different PAs) required to achieve a certain percentage of lysis may therefore vary by a factor of 2 to 2.5 (see FIGS. 1–7).

After addition of the respective PA or PA-combination, the tubes are slightly rotated at 37° C. and 100 μl samples of the plasma are taken at different time intervals. Radioactivity in the samples, released during lysis from the clot, is measured in a γ-counter and expressed as % lysis compared to a control without plasminogen activator. The results are shown in FIGS. 1–7.

7a: Combination of tPA with K$_2$tuPA 70 ng/ml tPA or 280 ng/ml K$_2$tuPA are added either alone or in combination to the clotted plasma. The result is shown in FIG. 1. The complementary, and not simply additive mode of actin is most pronouncedly seen at early time points with tPA shortens the lag phase in the beginning of the K$_2$tuPA mediated lysis.

7b: Combination of tPA with FK$_2$tuPA 35 ng/ml tPA or 140 ng/ml FK$_2$tuPA are added either alone or in combination to the clotted plasma. The result is shown in FIG. 2.

7c: Combination of uK$_2$tPA with scuPA 140 ng/ml uK$_2$tPA or 280 ng/ml scuPA are added either alone or in combination to the clotted plasma. The result is shown in FIG. 3.

7d: Combination of uK$_2$tPA with K$_2$tuPA 70 ng/ml uK$_2$tPA or 70 ng/ml K$_2$tuPA are added either alone or in combination to the clotted plasma. The result is shown in FIG. 4.

7e: Combination of tPA B-chain (fused) with scuPA 70 ng/ml tPA B-chain (fused) or 280 ng/ml scuPA are added either alone or in combination to the clotted plasma. The result is shown in FIG. 5.

Surprisingly, as demonstrated in FIGS. 3, 4 and 5, tPA can be replaced by either uK$_2$tPA or tPA B-chain (fused) in the combination with scuPA or one of its substitutes to give the same effect.

7f: Combination of tPA with uK$_2$tPA 70 ng/ml tPA or 70 ng/ml uK$_2$tPA are added either alone or in combination to the clotted plasma. The result is shown in FIG. 6.

7g: Combination of K$_2$tuPA with FK$_2$tuPA 70 ng/ml K$_2$tuPA or 140 ng/ml FK$_2$tuPA are added either alone or in combination to the clotted plasma. The result is shown in FIG. 7.

As demonstrated in FIGS. 6 and 7, no complementary stimulation of clot lysis is observed with either tPA combined with uK$_2$tPA, or with K$_2$tuPA combined with FK$_2$tuPA. In both cases lysis is simply additive.

EXAMPLE 8

Pharmaceutical Composition for Parenteral Administration

The pharmaceutical combination composition consists of six vials each containing 5 mg lyophilized tPA as component A and 300 mg dextrose and six vials each containing 20 mg FK$_2$tuPA as component B and 300 mg dextrose.

A solution for parenteral administration of tPA or FK$_2$tuPA is prepared by dissolving the content of each of the six vials in one 10 ml ampoule of sterile pyrogene-free solvent containing 100 mM ammonium acetate buffer adjusted to pH 4.0 with acetic acid.

Instead of using tPA and FK$_2$tuPA it is also possible to use equivalent amounts of other PAs as components A and B, such as tPA B-chain (fused), tPA B-chain (extended) or uK$_2$tPA as component A and K$_2$tuPA as component B.

Deposit of Microorganisms

The following microorganisms were deposited at the Deutsche Sammlung von Mikroorganimsen (DSM), Mascheroder Weg 1b, D-3300 Braunschweig (FRG).

| microorganism | deposition date | accession number |
|---|---|---|
| Saccharomyces cerevisiae HT246 | April 15, 1987 | DSM 4084 |
| E. coli HB101/p30 | October 23, 1987 | DSM 4297 |
| E. coli HB101/p31/PH05-TPA18 | December 19, 1988 | DSM 5118 |

We claim:

1. A pharmaceutical composition comprising components A and B,
   wherein A represents tPA and B is a plasminogen activator of formula $$NH_2-X_2-L_2-Y_2-COOH \qquad (II)$$

denoted FK$_2$tuPA, in which X$_2$ represents an amino acid sequence consisting of amino acids 1 to 49 and 176 to 262 of human tPA; L$_2$ represents an amino acid sequence consisting of amino acids 263 to 275 of human tPA; and Y$_2$ is the catalytic domain of human uPA consisting of amino acids 159 to 411 of human uPA,
   wherein said components A and B are present in said composition wherein the ratio by weight of component A to component B is between 1:1 and 1:20.

2. A pharmaceutical composition according to claim 1 wherein the ratio by weight of component A to component B is between 1:1 and 1:10.

3. A pharmaceutical composition comprising components A and B,
   wherein A represents tPA and B is a plasminogen activator of formula II, denoted K$_2$tuPA, wherein X$_2$ is an amino acid sequence consisting of amino acids 1 to 3 and 176 to 262 of human tPA; L$_2$ represents an amino acid sequence consisting of amino acids 263 to 275 of human tPA; and Y$_2$ is the catalytic domain of human uPA consisting of amino acids 159 to 411 of human uPA,
   wherein said components A and B are present in said composition wherein the ratio by weight of component A to component B is between 1:1 and 1:20.

4. A pharmaceutical composition according to claim 3 wherein the ratio by weight of component A to component B is between 1:1 and 1:10.

5. A pharmaceutical composition comprising components A and B, wherein A is a plasminogen activator of the formula $$NH_2—X_1—L_1—Y_1—COOH \quad (I),$$

denoted $uK_2tPA$, wherein $X_1$ is an amino acid sequence consisting of amino acids 1 to 44 of human tPA linked in series to amino acids 176 to 262 of human tPA; $L_1$ represents an amino acid sequence consisting of amino acids 263 to 275 of human tPA; and $Y_1$ represents the catalytic domain of human tPA consisting of amino acids 276 to 527 of human tPA; and B is a plasminogen activator of formula II denoted $K_2tuPA$, wherein $X_2$ is an amino acid sequence consisting of amino acids 1 to 3 and 176 to 262 of human tPA; $L_2$ represents an amino acid sequence consisting of amino acids 263 to 275 of human tPA; and $Y_2$ is the catalytic domain of human uPA consisting of amino acids 159 to 411 of human uPA, wherein said components A and B are present in said composition wherein the ratio by weight of component A to component B is between 1:1 and 1:20.

6. A pharmaceutical composition according to claim 5 wherein the ratio by weight of component A to component B is between 1:1 and 1:10.

* * * * *